(12) United States Patent
Neamati et al.

(10) Patent No.: US 8,183,236 B2
(45) Date of Patent: May 22, 2012

(54) COMPOUNDS WITH HIV-1 INTEGRASE INHIBITORY ACTIVITY AND USE THEREOF AS ANTI-HIV/AIDS THERAPEUTICS

(75) Inventors: Nouri Neamati, Los Angeles, CA (US); Raveendra S. Dayam, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 661 days.

(21) Appl. No.: 12/102,619

(22) Filed: Apr. 14, 2008

(65) Prior Publication Data

US 2009/0088420 A1    Apr. 2, 2009

Related U.S. Application Data

(60) Provisional application No. 60/911,446, filed on Apr. 12, 2007.

(51) Int. Cl.
| | |
|---|---|
| *C07D 277/36* | (2006.01) |
| *C07D 417/06* | (2006.01) |
| *C07D 417/04* | (2006.01) |
| *C07D 403/12* | (2006.01) |
| *A61K 31/55* | (2006.01) |
| *A61K 31/452* | (2006.01) |

(52) U.S. Cl. ............... 514/217.07; 514/226.5; 514/269; 514/312; 514/253.08; 514/336; 544/319; 544/48

(58) Field of Classification Search ..................... None
See application file for complete search history.

(56) References Cited

U.S. PATENT DOCUMENTS 5,646,163 A * 7/1997 Demuth et al. ............... 514/312

OTHER PUBLICATIONS

Neamati et al. in Journal of Medicinal Chemistry 1997, 40, 942-951.*
Morissette et al. in Advanced Drug Delivery Reviews 56 (2004) 275-300.*
Vippagunta et al. in Advanced Drug Delivery Reviews, 48 (2001) 3-26.*
Tait et al. in Bioorganic & Medicinal Chemistry Letters 6(1) 93-96 (1996).*
Deng, et al., 2007, Biorgains & Medicinal Chemistry, "Discovery of structurally diverse HIV-1 integrase inhibitors based on a chalcone pharmacophore," 15: 4985-5002.
Dayam, et al., 2008, "Quinolone 3-carboxylic acid pharmacophore: design of second generaion HIV-1 integrase inhibitors," J. Med. Chem., 51: 1136-1144.

* cited by examiner

*Primary Examiner* — Timothy Thomas
*Assistant Examiner* — Dennis Heyer
(74) *Attorney, Agent, or Firm* — DLA Piper LLP (US)

(57) ABSTRACT

Pharmacophore models to be used in drug design and discovery are provided. An in silico protocol and in vitro assays are presented. Compounds and their pharmaceutically acceptable salts with HIV-1 integrase inhibitory and anti-HIV activity and use thereof in the treatment of HIV/AIDS and related infections either alone or in combination with all the known antiretroviral therapeutics are described.

5 Claims, 7 Drawing Sheets

A

B

A

B

A

B

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Synthetic oligonucleotide

<400> SEQUENCE: 1
gtgtggaaaa tctctagcag t                                                  21

<210> SEQ ID NO 2
<211> LENGTH: 21
<212> TYPE: DNA
<213> ORGANISM: Artificial

```
<220> FEATURE:
<223> OTHER INFORMATION: Synthetic oligonucleotide

<400> SEQUENCE: 2
actgctagag attttccaca c                                          21
```

COMPOUNDS WITH HIV-1 INTEGRASE INHIBITORY ACTIVITY AND USE THEREOF AS ANTI-HIV/AIDS THERAPEUTICS

RELATED APPLICATION

This application claims priority to U.S. Provisional Application Ser. No. 60/911,446, filed on Apr. 12, 2007, the content of which is incorporated herein by reference in its entirety.

FIELD OF THE INVENTION

The present invention relates to compounds with HIV-1 integrase inhibitory activity and their use in the treatment of HIV/AIDS and related infections.

BACKGROUND OF THE INVENTION

Human Immunodeficiency Virus (type-1) (HIV-1) belongs to retrovirus and a causative virus of Acquired Immunodeficiency Syndrome (AIDS). The pol gene of HIV-1 encodes three essential enzymes: reverse transcriptase (RT), protease (PR) and integrase (IN). Currently 21 FDA approved drugs targeting RT and PR are available and are administered in various combinations. The combination of highly active antiretroviral therapy (HAART) in compliant patients comes close to stopping virus evolution, however, eradication of the infection has not been achieved because of the persistence of latent HIV-1 in resting memory CD4+ T cells. Moreover, several factors including the emergence of multidrug-resistant HIV strains, drug toxicity, the patient's ability to adhere to the prescribed therapy and expensive medication have necessitated a reason to develop novel drugs, which target other viral replication processes.

HIV-1 integrase has emerged as an attractive target for antiretroviral drugs because of its crucial role in the viral replication processes. HIV-1 integrase catalyses two crucial steps required for the integration of viral DNA into the host chromosome. In the first step, while in the cytoplasm of an infected cell, integrase selectively cleaves two nucleotides (GT) from the 3' terminal of the viral cDNA in a reaction known as 3'-processing. Immediately after translocation to the nucleus as a component of the pre-integration complex, integrase randomly inserts the viral cDNA into the host genome, and this reaction is referred to as strand transfer or integration. Over the past years several integrase inhibitors have been discovered, yet none of them reached the clinic.

SUMMARY OF THE INVENTION

In view of the foregoing, the addition of integrase inhibitors to the existing combination therapy would certainly improve the outcome of the HIV/AIDS treatment.

Pharmacophore Models in Drug Design and Discovery:

Once a potential inhibitor against a known target has been identified, computational approaches such as pharmacophore-based three-dimensional (3D) database searching can play a key role in the discovery of novel leads with different chemical scaffolds.

A pharmacophore refers to the three dimensional arrangement of various functional groups (chemical features) that is essential for the molecule to bind effectively against a specific enzyme, protein, or a receptor.

Accordingly, the invention features the following:
1. Pharmacophore models that are shown in FIGS. 4-7 and pharmacophore features combination given in Tables 1-4.
2. Compounds represented by Formula 1-40 and their pharmaceutically acceptable salts with HIV-1 integrase inhibitory and anti-HIV activity and uses thereof in the treatment of HIV/AIDS and related infections alone and in combination with all the known antiretroviral therapeutics.

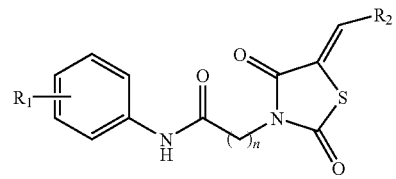

Formula 1

Representative compounds exemplified by Formula 1 with their integrase inhibitory activities are given in Table 5.

$R_1$: A variety of substitutions including (not limited to) hydrogen, halogens, hydroxyl, sulfhydryl, alkoxy, carboxyl, nitro, cyano, amino, amido, sulfonyl or any other organic functional group containing any number of carbon atoms.

$R_2$: Aliphatic or aromatic groups including alkyl, substituted alkyl, alkenyl, substituted alkenyl, alkynyl, substituted alkynyl, phenyl, substituted phenyl, aryl, substituted aryl, heteroaryl, substituted heteroaryl. Representative substitutions include (not limited to) halo, hydroxyl, sulfhydryl, alkoxy, carboxyl, carbonyl, nitro, cyano, amino, amido, sulfonyl and substituted heterocyclics.

n=C1-C4

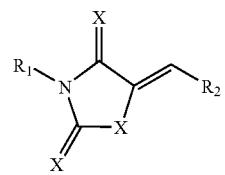

Formula 2

Representative compounds exemplified by Formula 2 with their integrase inhibitory activities are given in Table 6.

$R_1$: Aliphatic, aromatic, heterocyclic groups including alkyl, substituted alkyl, alkenyl, substituted alkenyl, alkynyl, substituted alkynyl, phenyl, substituted phenyl, aryl, substituted aryl, heteroaryl, substituted heteroaryl. Representative substitutions include (not limited to) halo, hydroxyl, sulfhydryl, alkoxy, carboxyl, carbonyl, nitro, cyano, amino, amido, sulfonyl, sulfonamide and substituted heterocyclics.

$R_2$: A variety of cyclic (3-7 member) aliphatic, aromatic, heterocyclic groups optionally substituted by functional groups including (not limited to) halogen, hydroxyl, sulfhydryl, alkoxy, carboxyl, carbonyl, nitro, cyano, amino, amido, sulfonyl, sulfonamide.

X=O or S or N

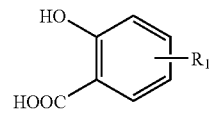

Formula 3

Representative compounds exemplified by Formula 3 with their integrase inhibitory activities are given in Table 7.

$R_1$: A variety of cyclic (1-7 member) or acyclic (1-7 member) aliphatic, aromatic, heterocyclic groups optionally substituted by functional groups including (not limited to) halogen, hydroxyl, sulfhydryl, alkoxy, carboxyl, carbonyl, nitro, cyano, amino, amido, sulfonyl, sulfonamide.

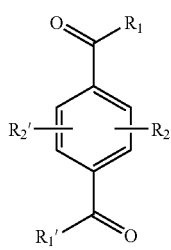

Formula 4

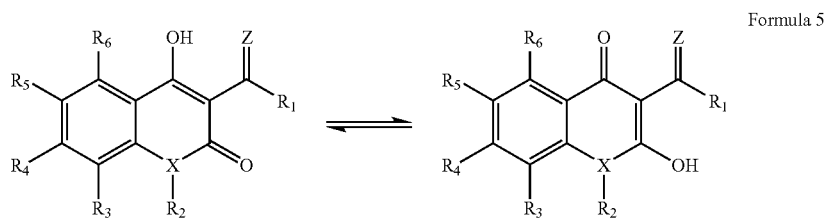

Formula 5

Representative compounds exemplified by Formula 4 with their integrase inhibitory activities are given in Table 8.

$R_1$, $R_1'$: Hydrogen, hydroxyl, sulfhydryl, alkoxy, aryloxy (Symmetric or asymmetric substitutions).

$R_2$, $R_2'$: Hydrogen, hydroxyl, sulfhydryl, alkoxy, aryloxy, and a variety of alkyl, aryl, heteroaryl groups optionally substituted with functional groups including (not limited to) halogen, hydroxyl, sulfhydryl, alkoxy, carboxyl, carbonyl, nitro, cyano, amino, amido, sulfonyl, sulfonamide.

Representative compounds exemplified by Formula 5 with their integrase inhibitory activities are given in Table 9.

$R_1$: Hydrogen, hydroxyl, sulfhydryl, alkoxy, aryloxy, NH- with optionally substituted aliphatic, heteroaliphatic, aryl, heteroaryl groups.

X—$R_2$: C—$R_2'$ N—$R_2$ $R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_3$-$R_6$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Z=O, S

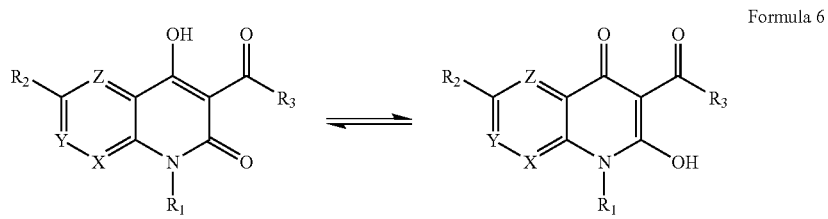

Formula 6

Representative compounds exemplified by Formula 6 are given in Table 10.

$R_1$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_3$: Hydrogen, hydroxyl, sulfhydryl, alkoxy, aryloxy.

X=C or N; γ=C or N; Z C or N

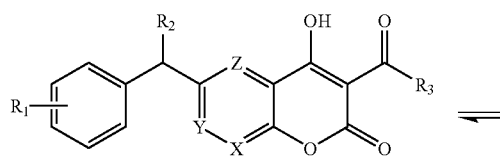

Representative compounds exemplified by Formula 7 are given in Table 11.

$R_1$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_2$: Hydrogen, halogen, hydroxyl, sulfhydryl, alkoxy, aryloxy.

$R_3$: Hydrogen, hydroxyl, sulfhydryl, alkoxy, aryloxy.

X=C or N; γ=C or N; Z=C or N

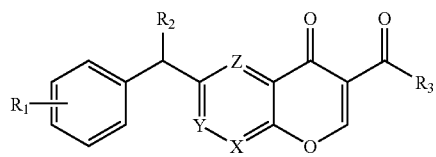

Formula 8

Representative compounds exemplified by Formula 8 are given in Table 12.

$R_1$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_2$: Hydrogen, halogen, hydroxyl, sulfhydryl, alkoxy, aryloxy $R_3$: Hydrogen, hydroxyl, sulfhydryl, alkoxy, aryloxy.

X=C or N; γ=C or N; Z=C or N

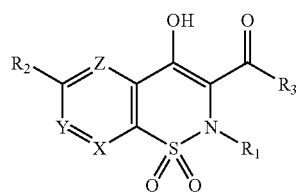

Formula 9

Representative compounds exemplified by Formula 9 are given in Table 13.

$R_1$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_3$: Hydrogen, hydroxyl, sulfhydryl, alkoxy, aryloxy,

X=C or N; Y=C or N; Z=C or N

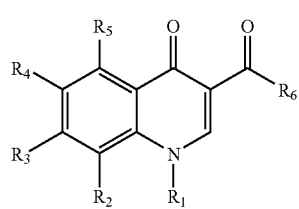

Formula 10

Representative compounds exemplified by Formula 10 are given in Table 14

$R_1$-$R_5$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

R₅: Hydrogen, hydroxyl, sulfhydryl, alkoxy, aryloxy

Formula 11

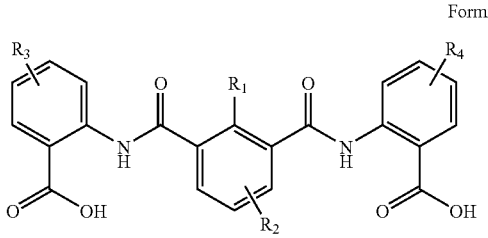

Representative compounds exemplified by Formula 11 are given in Table 15

R₁: Hydrogen, hydroxyl, sulfhydryl, alkoxy, aryloxy
R₂-R₄: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 12

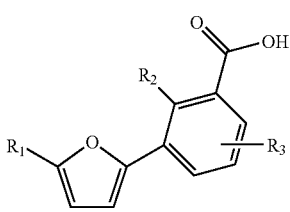

Representative compounds exemplified by Formula 12 are given in Table 16

R₁ and R₃: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.
R₂: Hydrogen, hydroxyl, sulfhydryl, alkoxy, aryloxy Formula 13

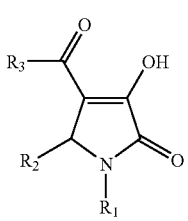

Representative compounds exemplified by Formula 13 are given in Table 17

R₁-R₃: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 14

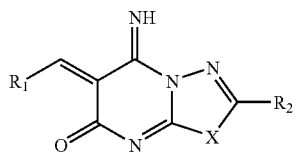

Representative compounds exemplified by Formula 14 are given in Table 18

R₁-R₂: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.
X=N or O or S Formula 15

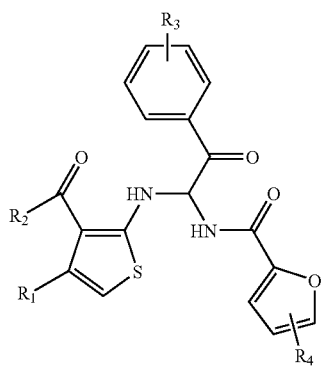

Representative compounds exemplified by Formula 15 are given in Table 19

R₂: Hydrogen, hydroxyl, sulfhydryl, alkoxy, aryloxy
R₁ and R₃-R₄: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 16

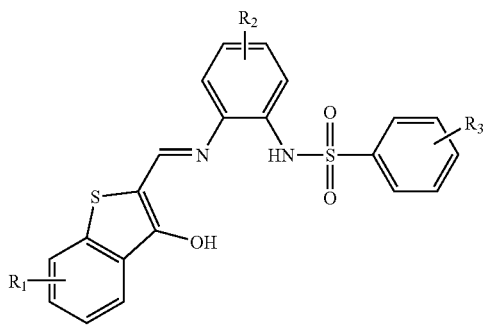

Representative compounds exemplified by Formula 16 are given in Table 20

$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 17

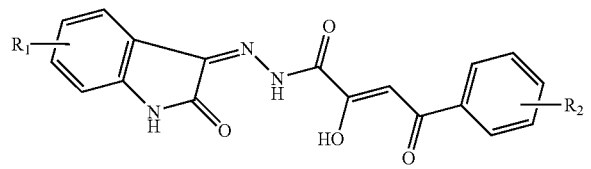

Representative compounds exemplified by Formula 17 are given in Table 21

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 18

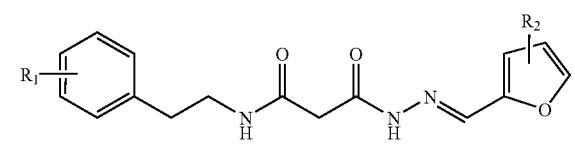

Representative compounds exemplified by Formula 18 are given in Table 22

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 19

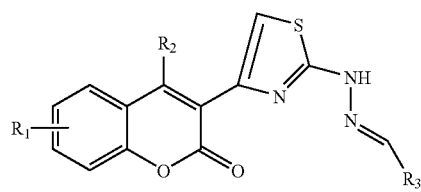

Representative compounds exemplified by Formula 19 are given in Table 23

$R_1$ and $R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_2$: Hydrogen, hydroxyl, carboxyl, carbonyl, sulfhydryl, alkoxy, aryloxy

Formula 20

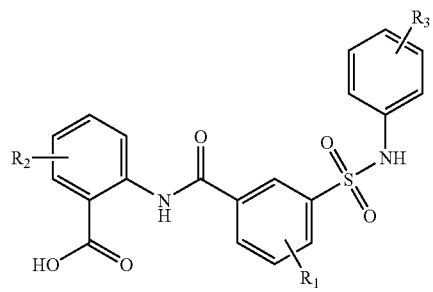

Representative compounds exemplified by Formula 20 are given in Table 24

$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 21

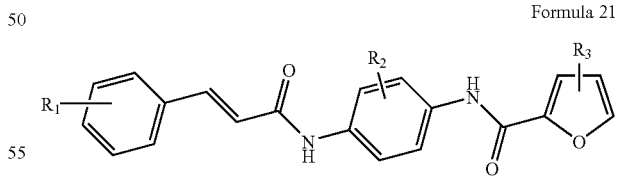

Representative compounds exemplified by Formula 21 are given in Table 25

$R_1$ and $R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

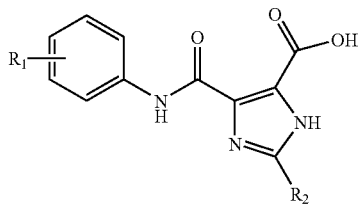

Formula 22

Representative compounds exemplified by Formula 22 are given in Table 26

$R_1$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

$R_2$: Hydrogen, hydroxyl, carboxyl, carbonyl, sulfhydryl, alkoxy, aryloxy

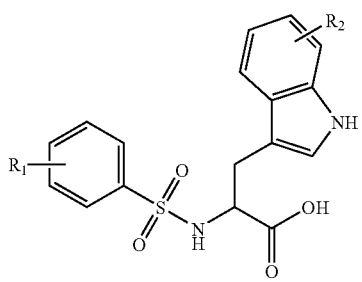

Formula 23

Representative compounds exemplified by Formula 23 are given in Table 27

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

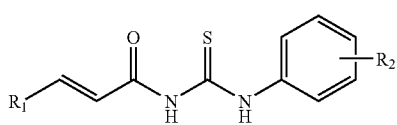

Formula 24

Representative compounds exemplified by Formula 24 are given in Table 28

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

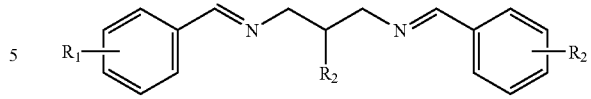

Formula 25

Representative compounds exemplified by Formula 25 are given in Table 29

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 26

Representative compounds exemplified by Formula 26 are given in Table 30

$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 27

Representative compounds exemplified by Formula 27 are given in Table 31

$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 28

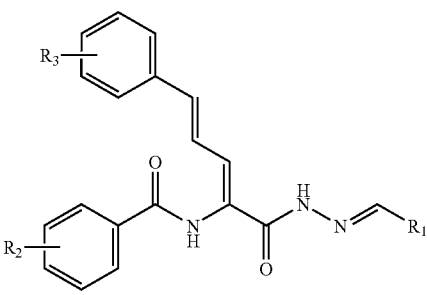

Representative compounds exemplified by Formula 28 are given in Table 32
$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 29

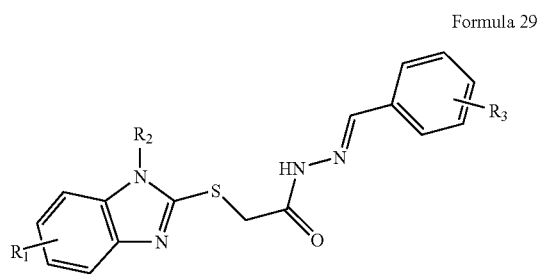

Representative compounds exemplified by Formula 29 are given in Table 33
$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 30

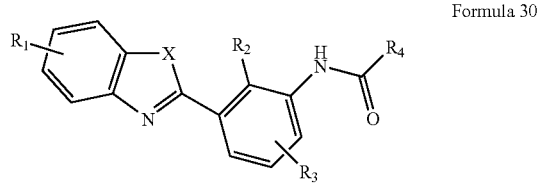

Representative compounds exemplified by Formula 30 are given in Table 34
$R_2$: Hydrogen, hydroxyl, carboxyl, carbonyl, sulfhydryl, alkoxy, aryloxy
$R_1$ and $R_2$-$R_4$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.
X=N or O or S Formula 31

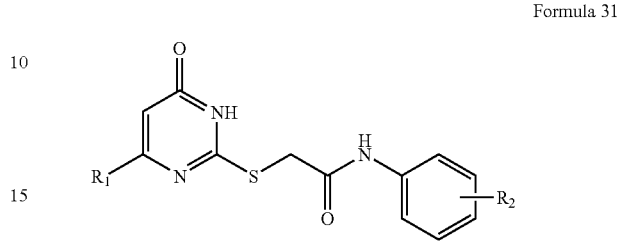

Representative compounds exemplified by Formula 31 are given in Table 35
$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

Formula 32

Representative compounds exemplified by Formula 32 are given in Table 36
$R_1$ and $R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.
$R_2$: Hydrogen, hydroxyl, carboxyl, carbonyl, sulfhydryl, alkoxy, aryloxy Formula 33

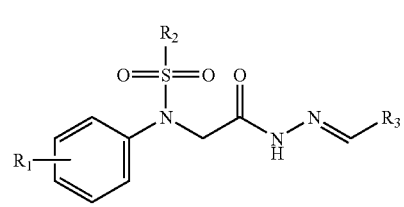

Representative compounds exemplified by Formula 33 are given in Table 37
$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

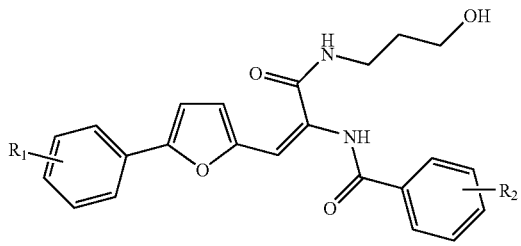

Formula 34

Representative compounds exemplified by Formula 34 are given in Table 38

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

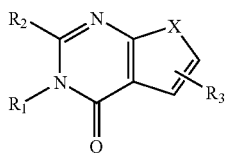

Formula 35

Representative compounds exemplified by Formula 35 are given in Table 39

$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.
X=N or O or S

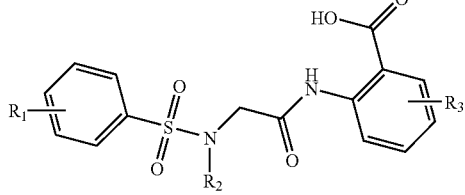

Formula 36

Representative compounds exemplified by Formula 36 are given in Table 40

$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

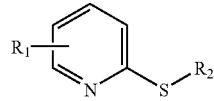

Formula 37

Representative compounds exemplified by Formula 37 are given in Table 41

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

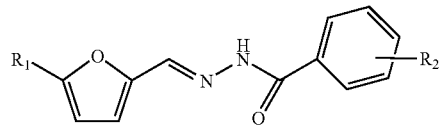

Formula 38

Representative compounds exemplified by Formula 38 are given in Table 42

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

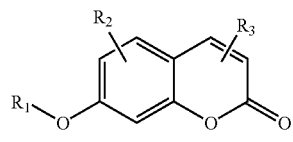

Formula 39

Representative compounds exemplified by Formula 39 are given in Table 43

$R_1$-$R_3$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.

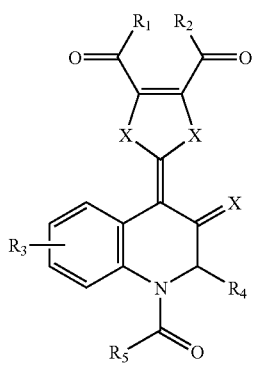

Formula 40

Representative compounds exemplified by Formula 40 are given in Table 44

$R_1$-$R_5$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.
X=O or S or N

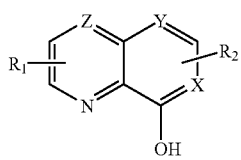

Formula 41

Representative compounds exemplified by Formula 41 are given in Table 45

$R_1$-$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatics, heterocyclics.
X=C or N; Y=C or N; Z=C or N 3. Pharmacophore features combination are given in Table 46.
4. Compounds represented by Formula 42-49 and their pharmaceutically acceptable salts with HIV-1 integrase inhibitory and anti-HIV activity and use thereof in the treatment of HIV/AIDS and related infections alone and incombination of all the known antiretroviral therapeutics.

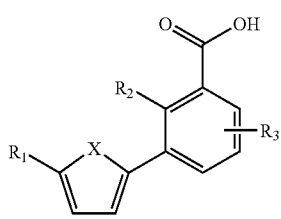

Formula 42

Representative compounds exemplified by Formula 42 are given in Tables 47 and 48

$R_1$: Hydrogen atom, cyclic or acyclic, straight or branched, saturated or unsaturated aliphatic, heteroaliphatic groups with optional substitutions, aryl or heteroaryl groups with optional substitutions. Aliphatic amides with optional substitutions. Hydrazides or hydrazines with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatic, heterocyclic groups.

$R_2$: Hydrogen, hydroxyl, sulfhydryl, alkoxy, aryloxy $R_5$: Hydrogen, halogen, hydroxyl, carboxyl, alkoxy, aryloxy, amine, amide, nitro, sulfonamide, substituted aromatics or heterocyclic groups.

X=O or S or NH

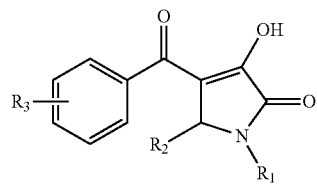

Formula 43

Representative compounds exemplified by Formula 43 are given in Table 49

$R_1$: Hydrogen atom, substituted cyclic or acyclic aliphatic or heteroaliphatic groups, substituted aromatic or heteroaromatic 4-7 member rings of carbon, nitrogen, oxygen, and sulfur atoms. Substitutions include (not limited to) hydrogen, halogen, alkoxy, aryloxy, sulfhydryl, sulfonamide, sulfone, carboxyl, amide, amine and nitro groups.

$R_2$: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatic, heterocyclic groups.

$R_3$: Hydrogen atom, hydroxyl, alkoxy, aryloxy, halogen, amine, carboxyl, amide, and nitro.

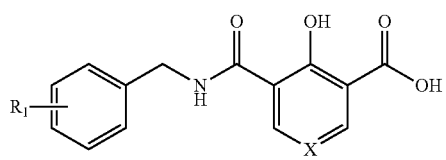

Formula 48

$R_1$: Hydrogen atom, halogen, hydroxyl, sulfhydryl, alkoxy, carboxyl, carbonyl, nitro, cyano, amino, amide, sulfonyl, sulfonamide and nitro. Substituted aliphatic, heteroaliphatic, aryl, and heteroaryl groups.

X=C or N

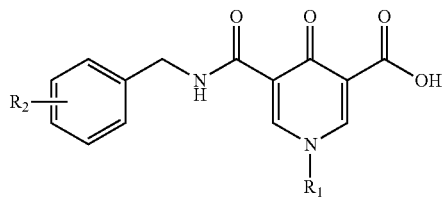

Formula 49

R₁: Hydrogen atom, optionally substituted aliphatic, heteroaliphatic, aryl and heteroaryl groups. Optional substitutions include (not limited to) hydrogen, halogen, hydroxyl, sulfhydryl, alkoxy, carboxyl, carbonyl, nitro, cyano, amino, amide, sulfonyl, sulfonamide and nitro.

R₂: Hydrogen atom, halogen, hydroxyl, sulfhydryl, alkoxy, carboxyl, carbonyl, nitro, cyano, amino, amide, sulfonyl, sulfonamide and nitro. Substituted aliphatic, heteroaliphatic, aryl and heteroaryl groups.

More specifically, the invention provides a composition comprising a compound, or a pharmaceutically acceptable salt, solvate, or hydrate thereof, wherein the compound conforms to one of the pharmacophores shown in FIGS. 4-7 and Tables 1-4 and 46. The compound may be of any of Formulas 1-49. For example, the compound is selected from the group consisting of the compounds shown in Tables 5-45 and 47-57. The composition may further comprise a pharmaceutically acceptable carrier.

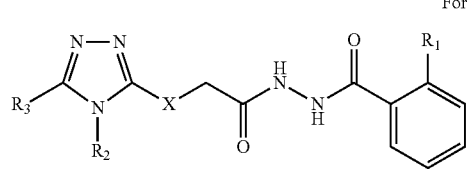

Formula 44

Representative compounds exemplified by Formula 44 are given in Table 50

R₁: Hydrogen atom, hydroxyl, sulfhydryl, carboxyl, amine, alkoxy, arloxy, and amide.

R₂-R₃: Hydrogen atom, cyclic or acyclic, straight or branched, saturated or unsaturated aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatic, heterocyclic groups X=O or S

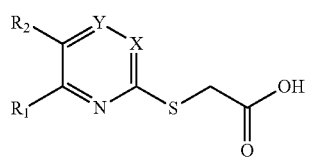

Formula 45

Representative compounds exemplified by Formula 45 are given in Table 51

R₁-R₂: Hydrogen atom, aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatic, heterocyclic groups X=C or N Y=C or N

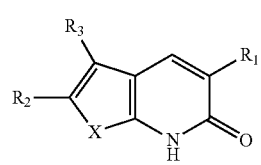

Formula 46

Representative compounds exemplified by Formula 46 are given in Table 52.

R₁: Carboxyl, or bioisosteres of carboxyl group such as triazole, tetrazole groups R₂-R₃: Hydrogen atom, aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatic, heterocyclic groups.

X=O or S

Several structurally diverse compounds retrieved by pharmacophore model 1 (HT5NODF.01) with HIV-1 integrase inhibitory activity are give in Table 53.

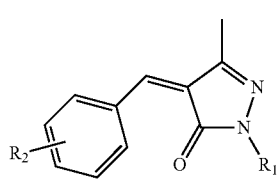

Formula 47

Representative compounds exemplified by Formula 47 are given in Table 54

R₁: Carboxyl, or bioisosteres of carboxyl group such as triazole, oxazole, and tetrazole groups.

R₂: Hydrogen atom, aliphatic, heteroaliphatic groups with optional substitutions, aryl or heteroaryl groups with optional substitutions. Representative substitutions include (not limited to) hydrogen, halogen, hydroxyl, sulfhydryl, alkoxy, carboxyl, carbonyl, nitro, cyano, amino, amido, sulfonyl, sulfonamide and substituted aromatic, heterocyclic groups.

The invention also provides a method of inhibiting HIV-1 integrase, comprising contacting a composition of claim 1 with an HIV-1 integrase, thereby inhibiting the activity of the HIV-1 integrase.

The invention further provides a computer-readable medium comprising a representation of one of the pharmacophores shown in FIGS. 4-7 and Tables 1-4 and 46.

Moreover, the invention provides a method of identifying an HIV integrase inhibitor, comprising comparing the three-dimensional structure of a compound with the three-dimensional structure of one of the pharmacophores shown in FIGS. 4-7 and Tables 1-4 and 46, and selecting the compound if the compound conforms to the features of the pharmacophore.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
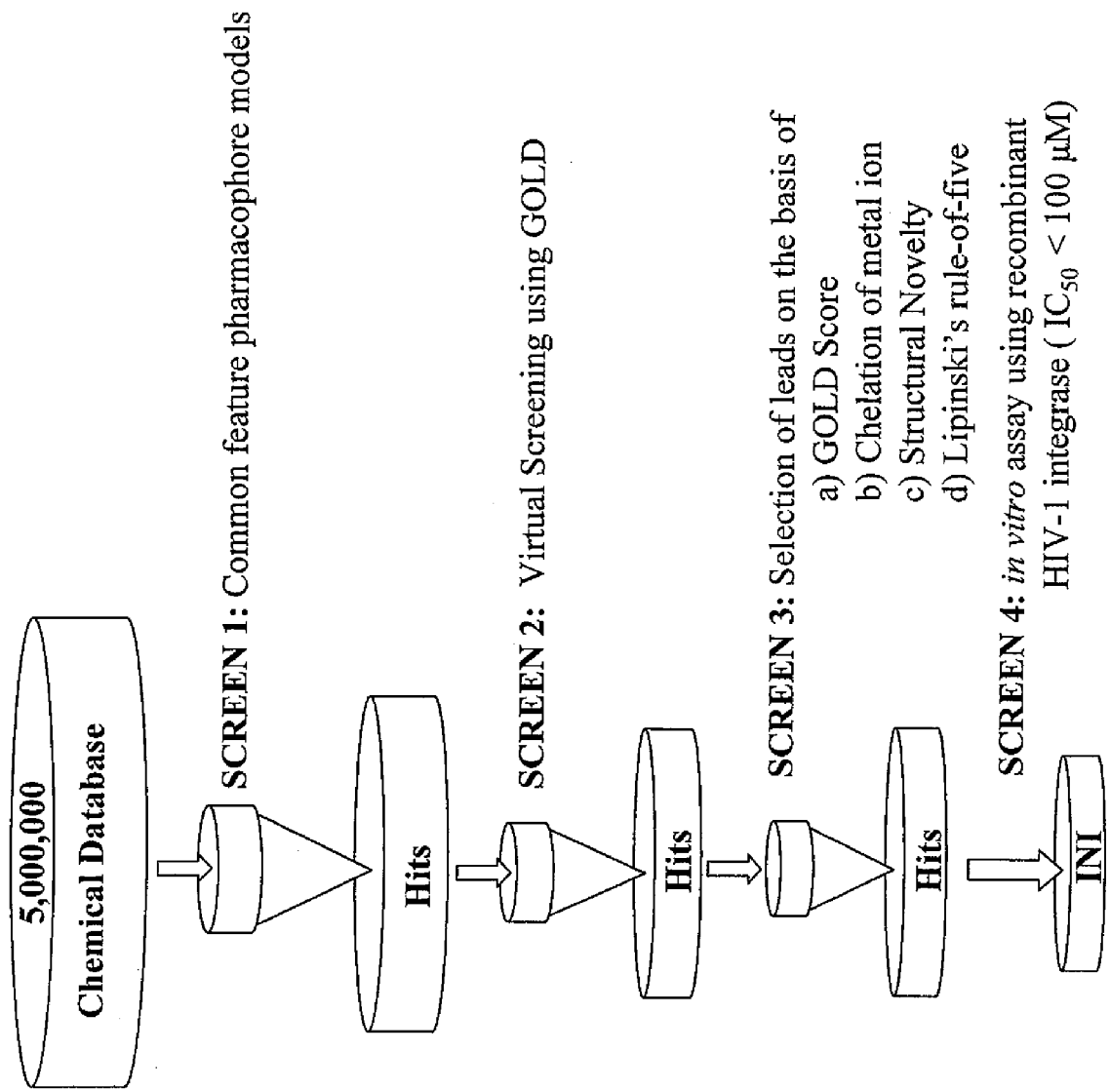
FIG. 1. In silico screening protocol implemented in the discovery of novel inhibitors for HIV-1 integrase.

This invention is based, at least in part, upon the unexpected discovery that the compounds identified as described below inhibit the activity of HIV-1 integrase. Accordingly, the invention provides a composition comprising a compound, or a pharmaceutically acceptable salt, solvate, or hydrate thereof, wherein the compound conforms to one of the pharmacophores shown in FIGS. 4-7 and Tables 1-4 and 46. The compound may be of any of Formulas 1-49. For example, the compound is selected from the group consisting of the compounds shown in Tables 5-45 and 47-57.

A composition of the invention may further comprise a pharmaceutically acceptable carrier. "Pharmaceutically acceptable carriers" include solvents, dispersion media, coatings, antibacterial and antifungal agents, isotonic and absorption delaying agents, and the like, compatible with pharmaceutical administration.

A compound of the invention may be obtained by chemical synthesis or from commercial sources. The composition of the invention is useful for inhibiting HIV-1 integrase and treating HIV-1/AIDS.

A composition of the invention is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Compositions suitable for injectable use include sterile aqueous solutions (where water soluble) or dispersions and sterile powders for the extemporaneous preparation of sterile injectable solutions or dispersion. For intravenous administration, suitable carriers include physiological saline, sterile water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the compounds in the required amounts in an appropriate solvent with one or a combination of ingredients enumerated above, as required, followed by filtered sterilization.

Generally, dispersions are prepared by incorporating the compounds into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the compounds can be incorporated with excipients and used in the form of tablets, troches, or capsules, e.g., gelatin capsules. Oral compositions can also be prepared using a fluid carrier for use as a mouthwash. Pharmaceutically or cosmeceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compositions are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The compositions of the invention can also be prepared in the form of suppositories (e.g., with conventional suppository bases such as cocoa butter and other glycerides) or retention enemas for rectal delivery.

In one embodiment, the compositions are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically or cosmeceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form," as used herein, refers to physically discrete units suited as unitary dosages for the subject to be treated; each unit containing a predetermined quantity of active compound calculated to produce the desired therapeutic or cosmeceutic effect in association with the required pharmaceutical or cosmeceutical carrier.

One object of the invention is to provide a method for inhibiting HIV-1 integrase in vitro or in vivo. The method comprises contacting a composition of the invention with an HIV-1 integrase.

Accordingly, in one embodiment, a composition of the invention is contacted with an HIV-1 integrase, e.g., in a cell, thereby inhibiting the activity of the HIV-1 integrase.

The invention further provides for both prophylactic and therapeutic methods of treating a subject in need thereof (e.g., a subject with HIV-1/AIDS) an effective amount of a composition of the invention.

"Subject," as used herein, refers to a human or animal, including all vertebrates, e.g., mammals, such as primates (particularly higher primates), sheep, dog, rodents (e.g., mouse or rat), guinea pig, goat, pig, cat, rabbit, cow; and non-mammals, such as chicken, amphibians, reptiles, etc. In a preferred embodiment, the subject is a human. In another embodiment, the subject is an animal.

A subject to be treated may be identified, e.g., using diagnostic methods known in the art, as being suffering from or at risk for developing a disease or condition. The subject may be identified in the judgment of a subject or a health care professional, and can be subjective (e.g., opinion) or objective (e.g., measurable by a test or diagnostic method).

As used herein, the term "treatment" is defined as the application or administration of a therapeutic agent to a subject, or application or administration of a therapeutic agent to an isolated tissue or cell line from a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease.

An "effective amount" is an amount of a therapeutic agent that is capable of producing a medically desirable result as delineated herein in a treated subject. The medically desirable result may be objective (i.e., measurable by some test or marker) or subjective (i.e., subject gives an indication of or feels an effect).

Toxicity and therapeutic efficacy of a compound of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of the compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of a compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of the compounds (I.e., an effective dosage) may range from, e.g., about 1 microgram per kilogram to about 500 milligrams per kilogram, about 100 micrograms per kilogram to about 5 milligrams per kilogram, or about 1 microgram per kilogram to about 50 micrograms per kilogram. The compounds can be administered, e.g., one time per week for between about 1 to 10 weeks, preferably between 2 to 8 weeks, more preferably between about 3 to 7 weeks, and even more preferably for about 4, 5, or 6 weeks. In subjects suffering from chronic diseases, such as arthritis or osteoporosis, life-long treatment may be necessary, for example, one time every day or preferably one time per week. It is furthermore understood that appropriate doses of a compound depend upon the potency of the compound. When one or more of these compounds is to be administered to a subject (e.g., an animal or a human), a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, the severity of the disease or disorder, previous treatments, and other diseases present. Moreover, treatment of a subject with a therapeutically effective amount of the compounds can include a single treatment or, preferably, can include a series of treatments.

Another object of the invention is to provide a method of identifying HIV-1 integrase inhibitors. Accordingly, the invention provides a computer-readable medium comprising a representation of one of the pharmacophores shown in FIGS. 4-7 and Tables 1-4 and 46.

As used herein, "computer readable media" refers to any medium that can be read and accessed directly by a computer. Such media include, but are not limited to, magnetic storage media, such as floppy discs, hard disc storage media, and magnetic tape; optical storage media such as CD-ROM; electrical storage media such as RAM and ROM; and hybrids of these categories such as magnetic/optical storage media. A skilled artisan can readily create a computer readable medium having recorded thereon a representation of a pharmacophore of the invention using any of the methods well known in the art.

By providing a representation of a pharmacophore of the invention in computer readable form, a skilled artisan can routinely access the pharmacophore information for a variety of purposes. For example, one skilled in the art can use a pharmacophore of the invention in computer readable form to compare with compound information stored within data storage means. Search means are used to identify compounds that match the features of the pharmacophore and therefore are candidate HIV-1 integrase inhibitors.

Accordingly, the invention provides a method of identifying an HIV-1 integrase inhibitor. The method comprises comparing the three-dimensional structure of a compound with the three-dimensional structure of a pharmacophore of the invention, and selecting the compound if the compound conforms to the features of the pharmacophore.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

The in silico protocol followed in the discovery of compounds with HIV-1 integrase inhibitory activity is schematically shown in FIG. 1.

Pharmacophore Models

Figure 2:
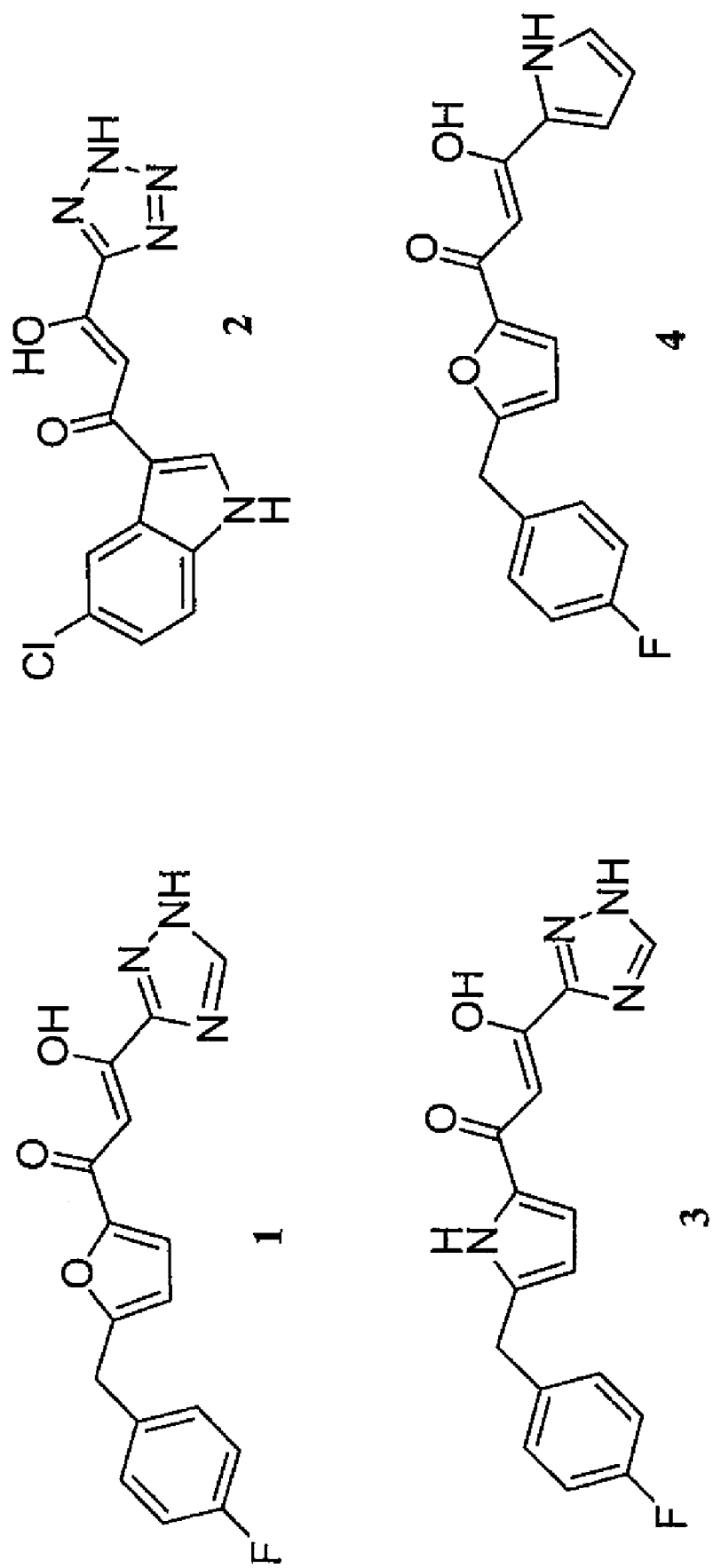
FIG. 2. Structures of the β-diketoacid bioisoteres used in the generation of common feature pharmacophore hypotheses.
Figure 3:
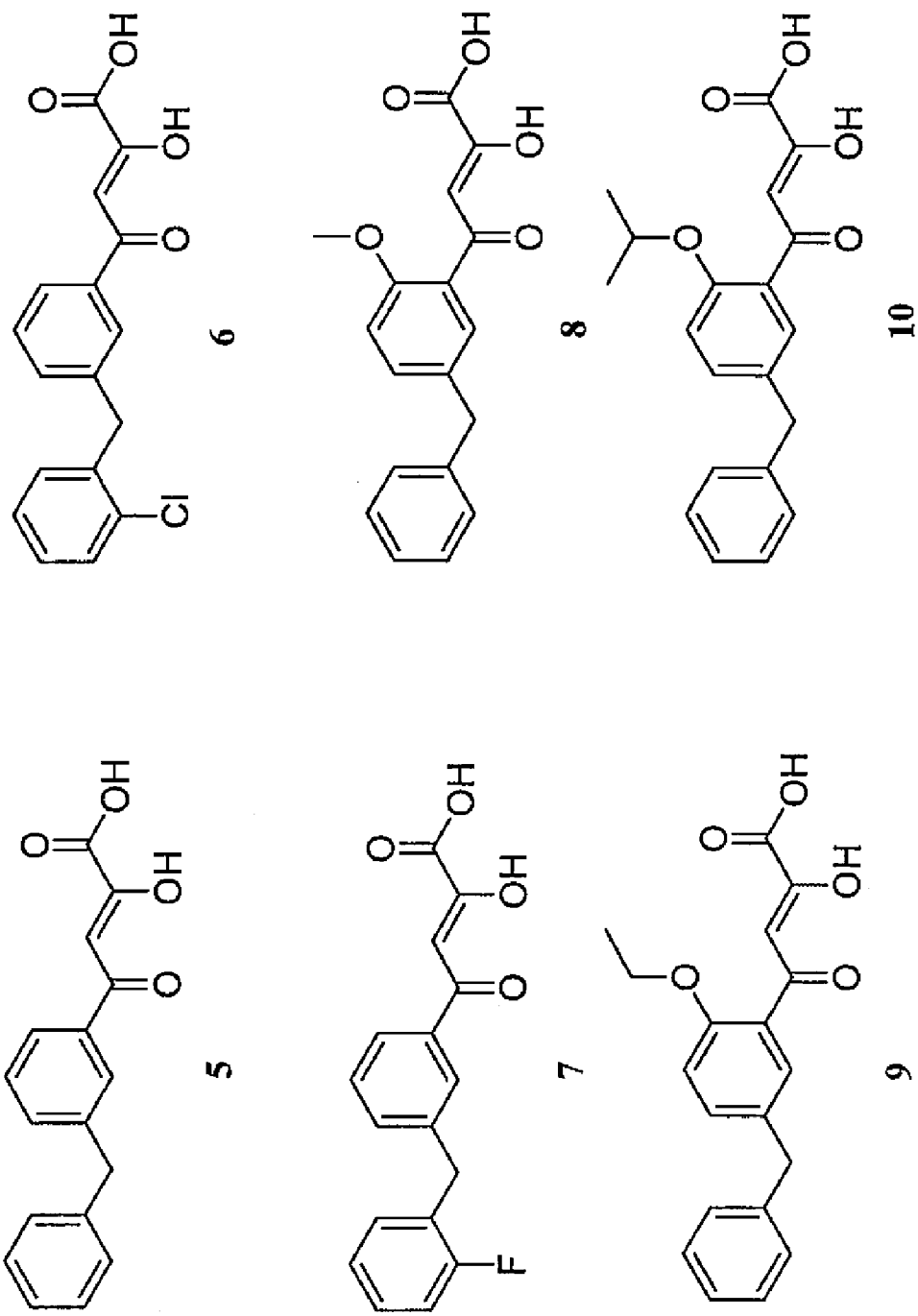
FIG. 3. Structures of the β-diketoacid inhibitors of HIV-1 Integrase used in the generation of common feature pharmacophore hypotheses.
Figure 4:
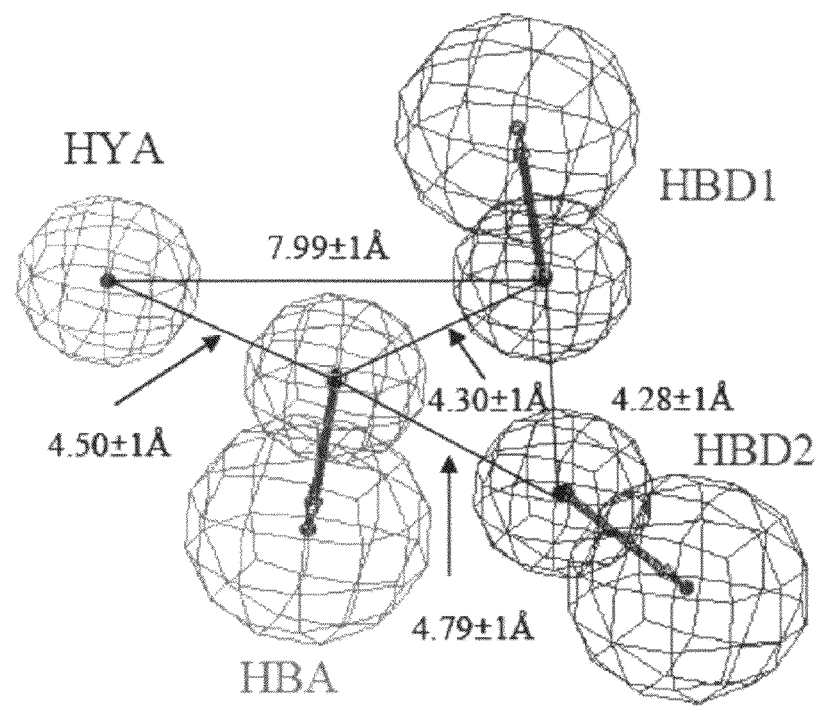
FIG. 4. (A) The best ranked four featured pharmacophore hypothesis (ECPHM4.01). ECPHM4.01 was used in the database mining to identify novel inhibitors for REV-1 integrase. (B) S-1360 is mapped on to ECPHM4.01. Pharmacopore features are color coded; Hydrophobic Aromatic (HYA)-light blue, H-Bond Acceptor (HBA)-green, H-Bond Donor (HBD)-magenta.
Figure 4:
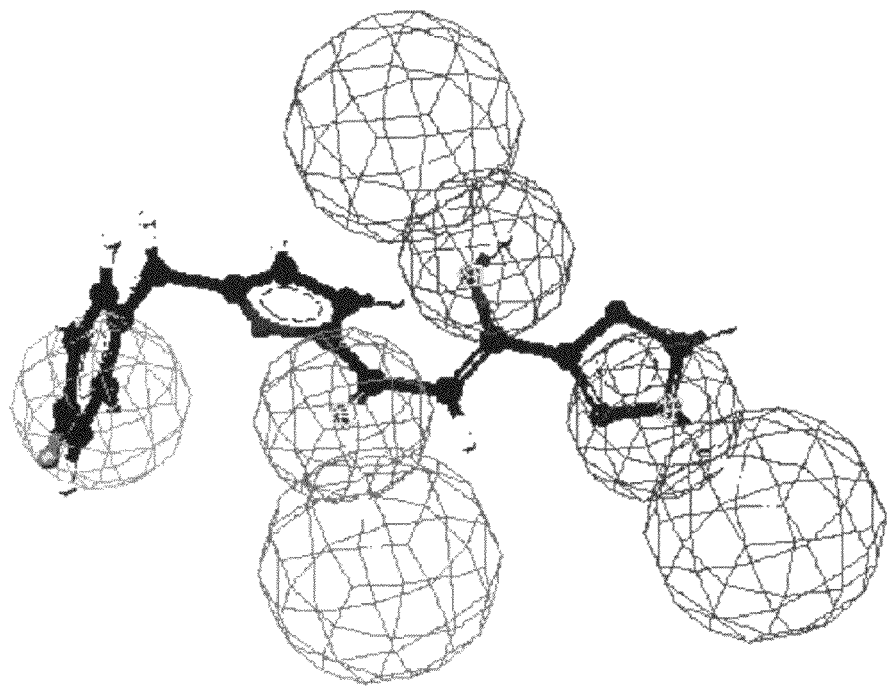
Figure 5:
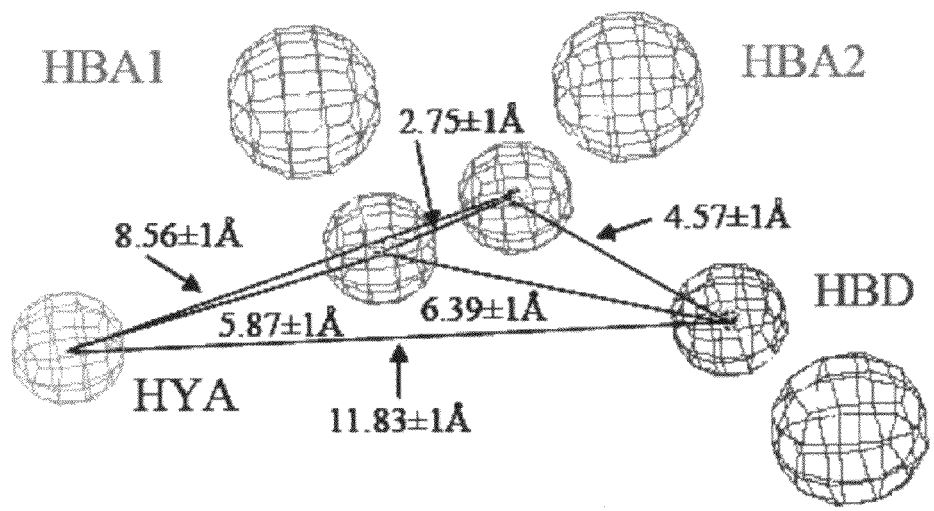
FIG. 5. (A) The best ranked four featured pharmacophore hypothesis (HCT4a.01). Pharmacophore hypotheses (HCT4a.01-10) were generated using conformations of the training set compounds (1-4) similar to the crystallographically determined structure of one of the training set compounds. HCT4a.01 was also used in the database mining to identify novel inhibitors for HIV-1 integrase. (B) S-1360 is mapped on to HCT4a.01. Pharmacopore features are color coded; Hydrophobic Aromatic (HYA)-light blue, H-Bond Acceptor (HBA)-green, H-Bond Donor (HBD)-magenta.
Figure 5:
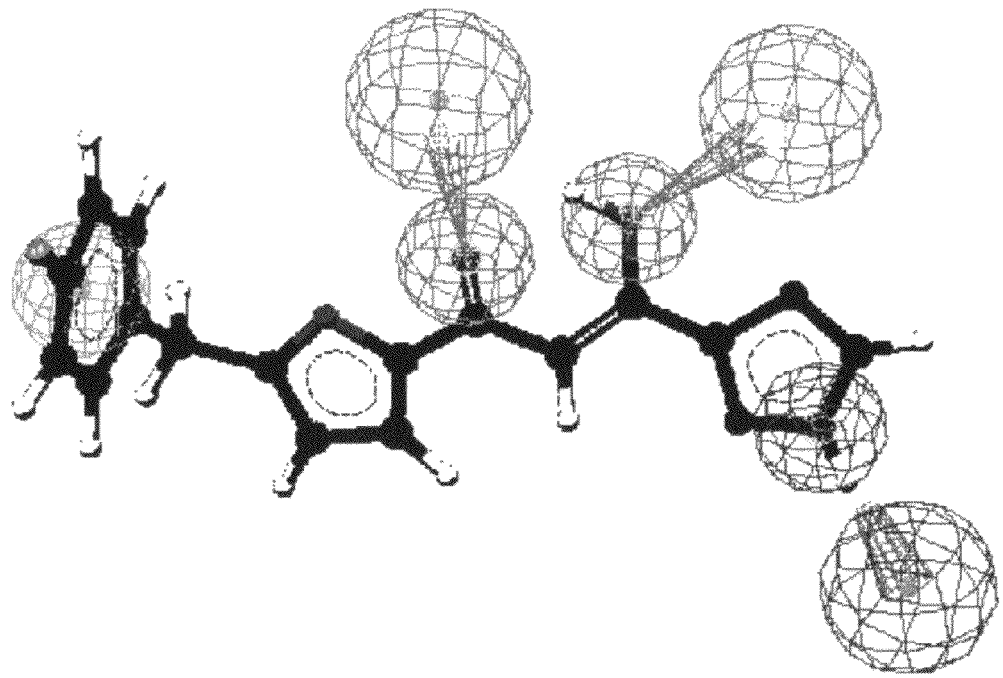
Figure 6:
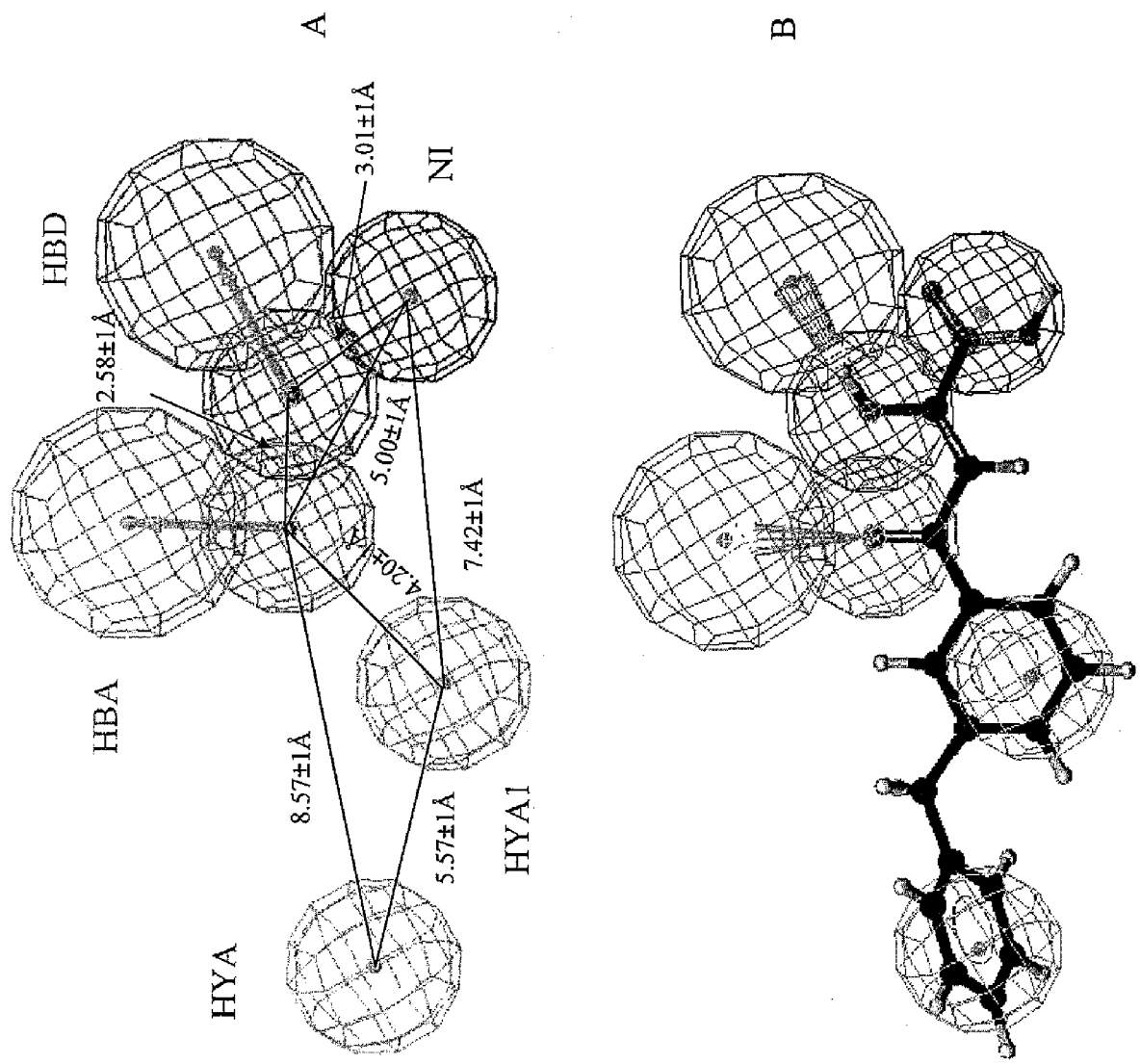
FIG. 6. (A) The best ranked four featured pharmacophore hypothesis (HSCT6AF25.01). All the chemical features found in the training set compounds were used in the pharmacophore hypotheses generation. (B) One of the training set compounds is mapped on to HSCT6AF25.01. Pharmacopore features are color coded; Hydrophobic Aromatic (HYA)-light blue, H-Bond Acceptor (HBA)-green, H-Bond Donor (HBD)-magenta, Negatively Ionizable (NI)— dark blue.
Figure 7:
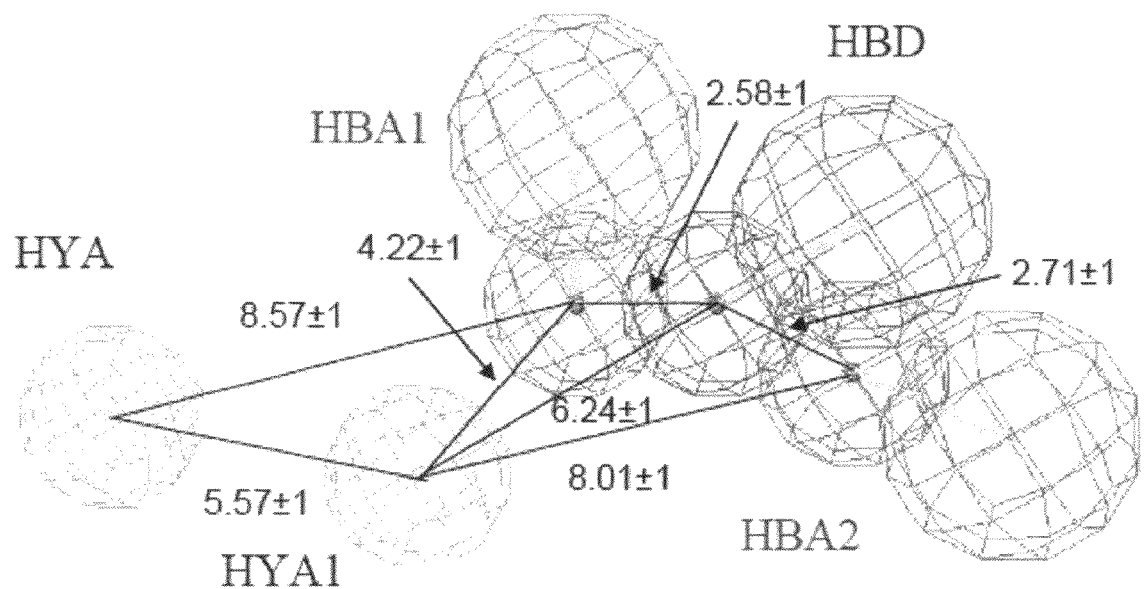
FIG. 7. (A) The best ranked four featured pharmacophore hypothesis (HSCT6NoN25.01). All the chemical features found in the training set compounds except negatively ionizable feature were used in the pharmacophore hypotheses generation. (B) One of the training set compounds is mapped on to HSCT6NoN25.01. Pharmacopore features are color coded; Hydrophobic Aromatic (HYA) light blue, H-Bond Acceptor (HBA)-green, H-Bond Donor (HBD)-magenta.
Figure 7:
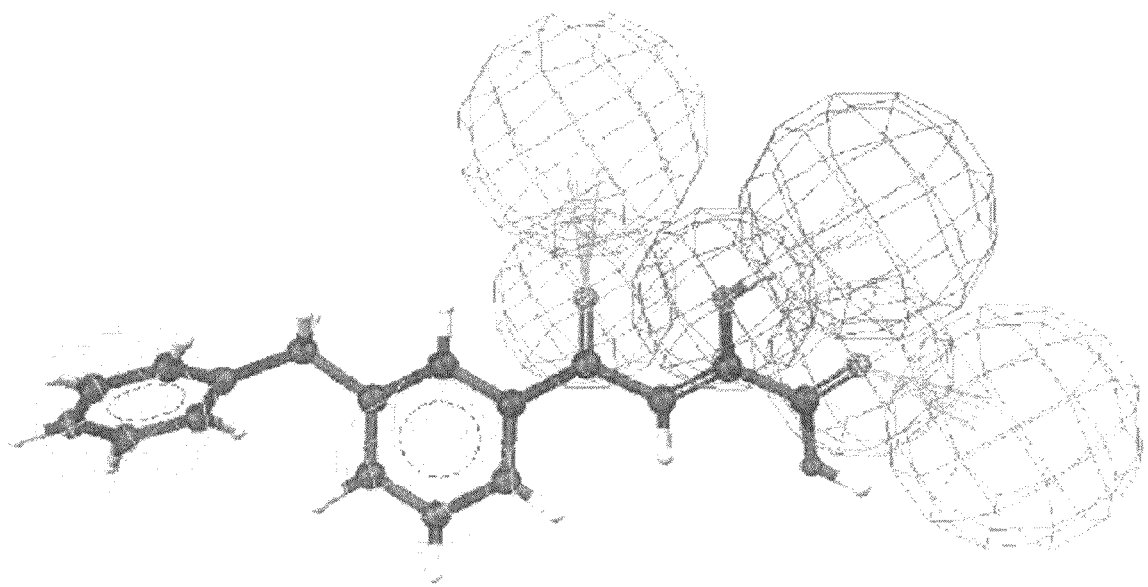

Several common feature pharmacophore models were generated using two sets of known HIV-1 integrase inhibitors (FIGS. 2-3). The top-ranking pharmacophores are expected to identify the hypothetical orientation of the active compounds and the common binding features interacting with the target. All training set inhibitors were somewhat structurally diverse but possessed some . . . common chemical features, and comparable inhibitory potencies. The pharmacophore models were generated using low energy conformation as well as using conformations similar to the crystallographically determined conformation of known integrase inhibitors. On the basis of the structural information from these known inhibitors and the active site of IN, a set of features were selected to be present in the pharmacophore generation experiment. The chemical features considered in the pharmacophore model generation run were H-bond donor (HBD), H-bond acceptor (HBA), Hydrophobic aromatic (HYA), Aromatic ring center (AR), and Negatively ionizable (NT) features. The validated pharmacophore models that were used in the database search are shown in FIGS. 4-7. The most potent integrase inhibitors were mapped onto the best ranked pharmacophore models (FIGS. 4-7). All the pharmacophore models that were generated specific to HIV-1 integrase are given in Tables 1-4 along with feature combinations and ranking scores.

Database Search:

The highest ranked common feature pharmacophore models (FIGS. 4-7) were used as search queries to retrieve compounds with novel chemical structure and desired chemical features from an in-house multi-conformer Catalyst-formatted database consisting of ~5,000,000 compounds. Drug-like properties of the retrieved hits from the database search were calculated using Accord for Excel.

Docking and Virtual Screening:

The subunit B of the core domain X-ray structure of Integrase (PDB 1BIS) in which all the active site amino acid residues were resolved was chosen for our docking and virtual screening purpose. A $Mg^{2+}$ ion was placed in the active site between carboxylate oxygen atoms of amino acid residues D64 and D116 considering the geometry of the $Mg^{2+}$ ion that was present in the subunit A of IN in PDB 1BIS and subunit A in IN-5CITEP complex X-ray structure (PDB 1SQ4). All the water molecules present in protein were removed and proper protonation states were assigned for acidic and basic residues of the protein. Docking was preformed using version 1.2 of the GOLD (Genetic Optimization for Ligand Docking) software package. GOLD is an automated ligand docking program that uses a genetic algorithm to explore the full range of ligand conformational flexibility with partial flexibility of the receptor. The algorithm was tested on a dataset of over 300 complexes extracted from the Brookhaven Protein DataBank. GOLD succeeded in more than 70% cases in reproducing the experimental bound conformation of the ligand. GOLD requires a user defined binding site. It searches for a cavity within the defined area and considers all the solvent accessible atoms in the defined area as active site atoms. A 20 Å radius active site was defined considering the carboxylate oxygen (OD1) atom of residue D64 as the center of the active site. All the compounds retrieved by the pharmacophore models were docked into the active site of IN. On the basis of the GOLD fitness score, for each molecule a bound conformation with high fitness score was considered as the best bound-conformation. All docking runs were carried out using standard default settings with a population size of 100, a maximum number of 100,000 operations, and a mutation and crossover rate of 95. The fitness function that was implemented in GOLD consisted basically of H-bonding, complex energy and ligand internal energy terms.

Materials, Chemicals, and Enzymes:

All compounds were dissolved in DMSO and the stock solutions were stored at −20° C. The γ[$^{32}$P]-ATP was purchased from either Amersham Biosciences or ICN.

Preparation of Oligonucleotide Substrates

The oligonucleotides 21 top, 5'-GTGTGGAAAATCTCTAGCAGT-3' (SEQ ID NO:1) and 21 bot, 5'-ACTGCTAGAGATTTTCCACAC-3' (SEQ ID NO:2) were purchased from Norris Cancer Center Core Facility (University of Southern California) and purified by UV shadowing on polyacrylamide gel. To analyze the extent of 3'-processing and strand transfer using 5'-end labeled substrates, 21 top was 5'-end labeled using T4 polynucleotide kinase (Epicentre, Madison, Wis.) and γ [$^{32}$P]-ATP (Amersham Biosciences or ICN). The kinase was heat-inactivated and 21 bot was added in 1.5-molar excess. The mixture was heated at 95° C., allowed to cool slowly to room temperature, and run through a spin 25 mini-column (USA Scientific) to separate annealed double-stranded oligonucleotide from unincorporated material.

Integrase Assays:

To determine the extent of 3'-processing and strand transfer, wild-type IN was preincubated at a final concentration of 200 nM with the inhibitor in reaction buffer (50 mM NaCl, 1 mM HEPES, pH 7.5, 50 µM EDTA, 50 µM dithiothreitol, 10% glycerol (w/v), 7.5 mM MnCl2, 0.1 mg/ml bovine serum albumin, 10 mM 2-mercaptoethanol, 10% dimethyl sulfoxide, and 25 mM MOPS, pH 7.2) at 30° C. for 30 min. Then, 20 nM of the 5'-end $^{32}$P-labeled linear oligonucleotide substrate was added, and incubation was continued for an additional one hour. Reactions were quenched by the addition of an equal volume (16 µl) of loading dye (98% deionized formamide, 10 mM EDTA, 0.025% xylene cyanol and 0.025% bromophenol blue). An aliquot (5 µl) was electrophoresed on a denaturing 20% polyacrylamide gel (0.09 M tris-borate pH 8.3, 2 mM EDTA, 20% acrylamide, 8M urea).

Gels were dried, exposed in a PhosphorImager cassette, and analyzed using a Typhoon 8610 Variable Mode Imager (Amersham Biosciences) and quantitated using ImageQuant 5.2. Percent inhibition (% I) was calculated using the following equation:

$$\%I = 100 \times [1 - (D-C)/(N-C)]$$

where C, N, and D are the fractions of 21-mer substrate converted to 19-mer (3'-processing product) or strand transfer products for DNA alone, DNA plus IN, and IN plus drug, respectively. The IC$_{50}$ values were determined by plotting the logarithm of drug concentration versus percent inhibition to obtain concentration that produced 50% inhibition.

Anti-HIV Assays in Cultured Cells:

The anti-HIV activity was evaluated in human T cell line CEM-SS infected with HIV-1 as described by Weislow et al. 45 In brief, cells were plated in 96-well plates at 5×10$^3$ cells/well and infected with HW-1RF (MOI=0.3). Serial dilutions of compounds were then immediately added to the cells in a final volume of 200 µl. In each experiment, AZT and dextran sulfate were included as control compounds for anti-HIV activity. The cells were maintained at 37° C. with 5% C02-containing humidified air for 6 days. Cell viability was quantified by absorbance at 450 nm after 4 h incubation with 2,3-bis[2-methoxy-4-nitro-5-sulfophenyl]-5-[(phenylamino)carbonyl]-2H-tetrazolium hydroxide (XTT) at 0.2. mg/ml. Antiviral activity was graded based on the degree of anti-HIV protection as active (80-100% protection), moderate (50-79% protection) and inactive (0-49% protection). Toxicity of the compounds was determined simultaneously on the same plate in uninfected CEM-SS cells.

TABLE 1

Pharmacophore models (ECPHM4) generated using the training set compounds (1-4) shown in FIG. 1 (Conformations used are low energy conformations generated using Catalyst (Accelrys, Inc) program)

| Hypothesis | Features Combinations [a] | Ranking Score |
|---|---|---|
| ECPHM4.01 | HYA, HBD1, HBD2, HBA | 35.02 |
| ECPHM4.02 | HYA, HBD1, HBD2, HBA | 35.02 |
| ECPHM4.03 | HYA, HBD1, HBA, HBA1 | 34.22 |
| ECPHM4.04 | HYA, HBD1, HBA, HBA1 | 34.22 |
| ECPHM4.05 | HYA, HBD1, HBD2, HBA | 34.08 |
| ECPHM4.06 | HYA, HBD1, HBD2, HBA | 34.08 |
| ECPHM4.07 | HYA, HBD1, HBD2, HBA | 33.76 |
| ECPHM4.08 | HYA, HBD1, HBA, HBA1 | 33.41 |
| ECPHM4.09 | HYA, HBD1, HBA, HBA1 | 33.41 |
| ECPHM4.10 | HYA, HBD1, HBA, HBA1 | 33.41 |

[a] HYA—Hydrophobic Aromatic; HBA—H-Bond Acceptor; HBD—H-Bond Donor Feature

TABLE 2

Pharmacophore models (HCT4a) generated using the training set compounds (1-4) shown in FIG. 1 (conformations used are similar to crystallographically determined conformation of one of the training set compounds)

| Hypothesis | Features Combinations [a] | Ranking Score |
|---|---|---|
| HCT4a.01 | HYA, HBD, HBA1, HBA2 | 37.41 |
| HCT4a.02 | HYA, HBD, HBA1, HBA2 | 37.20 |
| HCT4a.03 | HYA ,HBD, HBA1, HBA2 | 37.20 |
| HCT4a.04 | HYA, HBD, HBA1, HBA2 | 37.20 |
| HCT4a.05 | HYA, HBD, HBA1, HBA2 | 36.52 |
| HCT4a.06 | HYA, HBD, HBA1, HBA2 | 36.46 |
| HCT4a.07 | HYA, HBD, HBA1, HBA2 | 36.28 |
| HCT4a.08 | HYA, HBD, HBA1, HBA2 | 35.45 |
| HCT4a.09 | HYA, HBD, HBA1, HBA2 | 35.45 |
| HCT4a.10 | HYA, HBD, HBA1, HBA2 | 35.24 |

[a] HYA—Hydrophobic Aromatic; HBA—H-Bond Acceptor; HBD—H-Bond Donor Feature

TABLE 3

Pharmacophore models generated using the training set compounds (5-10) shown in FIG. 2 (All chemical features found in the training set compounds considered for pharmacophore generation)

| Hypothesis | Features Combinations [a] | Ranking Score |
|---|---|---|
| HSCT6AF25.01 | HYA, HYA1, HBD, HBA, NI | 88.09 |
| HSCT6AF25.02 | HRA, HYA, HBD, HBA, NI | 87.68 |
| HSCT6AF25.03 | HRA, HYA, HBD, HBA, NI | 87.68 |
| HSCT6AF25.04 | HRA, HYA, HBD, HBA, NI | 87.09 |
| HSCT6AF25.05 | HRA, HYA, HBD, HBA, NI | 87.09 |
| HSCT6AF25.06 | HYA, HYA1, HBA, HBA1, NI | 86.89 |
| HSCT6AF25.07 | HRA, HRA1, HBD, HBA, NI | 86.65 |
| HSCT6AF25.08 | HRA, HRA1, HBD, HBA, NI | 86.65 |
| HSCT6AF25.09 | HYA, HYA1, HBA, HBA1, NI | 86.48 |
| HSCT6AF25.10 | HYA, HYA1, HBA, HBA1, NI | 86.48 |

[a] HRA—Ring Aromatic; HYA—Hydrophobic Aromatic; HBA—H-Bond Acceptor; HBD—H-Bond Donor; NI—Negatively Ionizable Feature

TABLE 4

Pharmacophore models generated using the training set compounds (5-10) shown in FIG. 2 (All chemical features found in the training set compounds considered for pharmacophore generation except the negatively ionizable (NI) feature)

| Hypothesis | Features Combinations [a] | Ranking Score |
|---|---|---|
| HSCT6NoNF25.01 | HYA, HYA1, HBD, HBA, HBA1 | 80.97 |
| SCT6NoNF25.02 | HRA, HYA, HBD, HBA, HBA1 | 80.52 |
| SCT6NoNF25.03 | HRA, HYA, HBD, HBA, HBA1 | 80.52 |
| SCT6NoNF25.04 | HYA, HYA1, HBD, HBA, HBA1 | 80.28 |
| SCT6NoNF25.05 | HRA, HYA, HBD, HBA, HBA1 | 80.22 |
| SCT6NoNF25.06 | HRA, HYA, HBD, HBA, HBA1 | 80.22 |
| SCT6NoNF25.07 | HRA, HYA, HBD, HBA, HBA1 | 79.97 |
| SCT6NoNF25.08 | HRA, HYA, HBD, HBA, HBA1 | 79.94 |
| SCT6NoNF25.09 | HYA, HYA1, HBD, HBA, HBA1 | 79.83 |
| SCT6NoNF25.10 | HYA, HYA1, HBA, HBA1, HBA2 | 79.77 |

[a] HRA—Ring Aromatic; HYA—Hydrophobic Aromatic; HBA—H-Bond Acceptor; HBD—H-Bond Donor Feature

TABLE 5

Inhibition of HIV-1 Integrase Catalytic Activities of Representative Compounds Exemplified by Formula 1

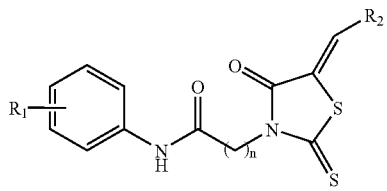

| Example | $R_1$ | $R_2$ | n | 3'-processing IC$_{50}$ (μM) | Strand Transfer IC$_{50}$ (μM) | GOLD Score |
|---|---|---|---|---|---|---|
| X92 | 3-COOH, 4-OH | 4-(OCH$_2$CH$_3$)phenyl | 2 | 17 ± 13 | 11 ± 6 | 52.18 |
| X94 | 3-COOH, 4-OH | benzo[1,3]dioxol-5-yl | 2 | 15 ± 10 | 17 ± 11 | 57.90 |
| X169 | 3-COOH, 4-OH | thiophen-2-yl | 3 | 44 ± 20 | 35 ± 16 | 52.59 |
| X170 | 3-COOH, 4-OH | 4-(CH$_2$CH$_3$)phenyl | 2 | 15 ± 3 | 11 ± 5 | 51.57 |
| X172 | 3-COOH, 4-OH | thiophen-2-yl | 2 | 38 ± 16 | 38 ± 16 | 56.39 |
| X185 | 3-COOH, 4-OH | 2-methyl-2-phenylvinyl | 2 | 36 ± 23 | 23 ± 3 | 57.25 |
| X175 | 3-OH, 4-COOH | thiophen-2-yl | 3 | 32 ± 14 | 25 ± 5 | 54.57 |
| X188 | 3-OH, 4-COOH | benzo[1,3]dioxol-5-yl | 2 | 33 ± 23 | 23 ± 13 | 57.62 |

TABLE 5-continued
Inhibition of HIV-1 Integrase Catalytic Activities of Representative
Compounds Exemplified by Formula 1
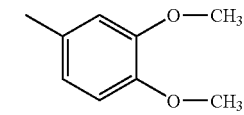
| Example | R₁ | R₂ | n | 3'-processing | Strand Transfer | GOLD Score |
|---|---|---|---|---|---|---|
| X192 | 3-OH, 4-COOH | 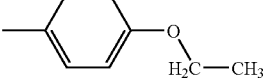 | 2 | 61 ± 34 | 17 ± 4 | 57.46 |
| X95 | 3-COOH | 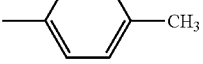 | 2 | 93 ± 12 | >100 | 51.98 |
| X100 | 3-COOH | 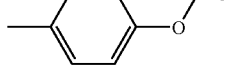 | 2 | 100 | >100 | 56.15 |
| X26 | 3-COOH | 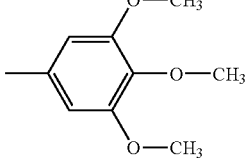 | 2 | >100 | >100 | 53.43 |
| X173 | 4-COOH |  | 2 | 97 ± 6 | 85 ± 15 | 50.05 |
| X176 | 4-COOH |  | 2 | 86 ± 15 | 86 ± 17 | 51.26 |
| X56 | 3-COOH | 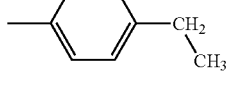 | 2 | >100 | >100 | 55.78 |
| X91 | 3-COOH | 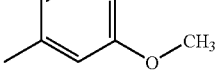 | 1 | >100 | >100 | 55.06 |
| X89 | 3-COOH | 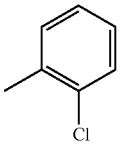 | 1 | >100 | >100 | 52.07 |
| X93 | 3-COOH |  | 1 | >100 | >100 | 58.95 |
(Inhibition of IN Catalytic Activities IC₅₀ (μM))

TABLE 5-continued

Inhibition of HIV-1 Integrase Catalytic Activities of Representative Compounds Exemplified by Formula 1

| Example | $R_1$ | $R_2$ | n | 3'-processing | Strand Transfer | GOLD Score |
|---|---|---|---|---|---|---|
| X97 | 3-COOH | 4-methylphenyl | 1 | 98 ± 4 | >100 | 56.04 |
| X118 | 4-OH | 2-methyl-6-methoxyphenyl | 2 | 99 ± 3 | 100 | 43.93 |
| X177 | 3-OH | 2-methylthiophene | 2 | >100 | >100 | 47.81 |
| X190 | 3-OH | 4-methyl-2,3-dimethoxyphenyl | 2 | >100 | 90 ± 10 | 53.28 |
| X184 | 2-OH, 4-NO$_2$ | 3-methoxy-5-methylphenyl | 1 | >100 | >100 | 49.84 |
| X191 | 2-OH, 5-NO$_2$ | 4-methylphenyl | 1 | 84 ± 24 | 80 ± 18 | 47.49 |
| X193 | 2-OH, 4-NO$_2$ | 2-chloro-6-methylphenyl | 1 | >100 | >100 | 46.44 |
| X194 | 2-OH, 5-NO$_2$ | 2-chloro-6-methylphenyl | 1 | 20 ± 7 | 18 ± 11 | 49.77 |
| X171 | 2-OH, 5-Cl | 3,4,5-trimethoxy-substituted phenyl | 1 | 32 ± 11 | 17 ± 2 | 46.78 |
| X195 | 2-OH, 4-NO$_2$ | 4-methylphenyl | 1 | >100 | >100 | |

TABLE 5-continued

Inhibition of HIV-1 Integrase Catalytic Activities of Representative Compounds Exemplified by Formula 1

[Structure: R1-phenyl-NH-C(=O)-(CH2)n-N(thiazolidine with =S, =O, =CHR2)]

| Example | R₁ | R₂ | n | 3'-processing | Strand Transfer | GOLD Score |
|---|---|---|---|---|---|---|
| X102 | | [structure with HOOC-phenyl-NH-C(=O)-CH2-N-thiazolidine-=C-thiazolidine-N-CH2-C(=O)-NH-phenyl-COOH] | | 59 ± 31 | 75 | 58.64 |
| X103 | | [structure with HO-phenyl-NH-C(=O)-CH2-N-thiazolidine-=C-thiazolidine-N-CH2-C(=O)-NH-phenyl-OH] | | 59 ± 37 | 69 | 51.30 |

TABLE 6

Inhibition of HIV-1 Integrase Catalytic Activities of Representative Compounds Exemplified by Formula 2

| Example | Structure | 3'-processing | Strand Transfer | GOLD Score |
|---|---|---|---|---|
| X200 | [structure: O2N-phenyl-NH-C(=O)-CH2CH2-N-thiazolidinone(=S)-=CH-phenyl-Cl] | >100 | >100 | 46.03 |

TABLE 6-continued

Inhibition of HIV-1 Integrase Catalytic Activities of Representative Compounds Exemplified by Formula 2

| Example | Structure | Inhibition of IN Catalytic Activities IC$_{50}$ (μM) | | GOLD Score |
|---|---|---|---|---|
| | | 3'-processing | Strand Transfer | |
| X124 | 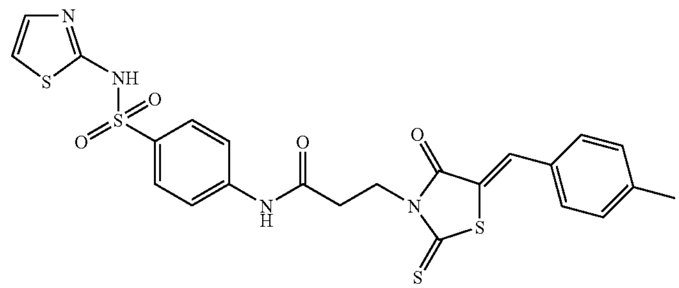 | 83 ± 21 | 44 ± 16 | 50.69 |
| X174 | 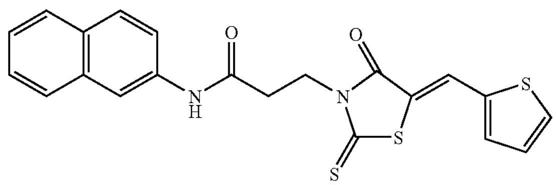 | >100 | >100 | 50.89 |
| X178 | 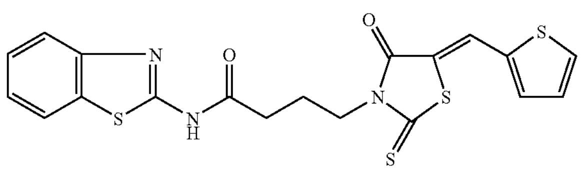 | 98 ± 5 | 100 | 54.21 |
| X187 | 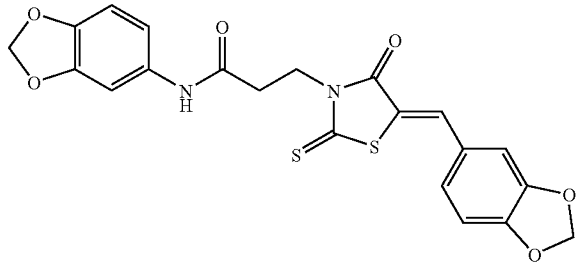 | 97 ± 6 | 93 ± 12 | 56.55 |
| X105 | 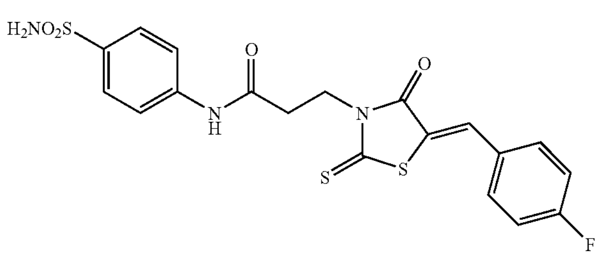 | 88 ± 22 | 84 ± 2 | 59.21 |
| X90 | 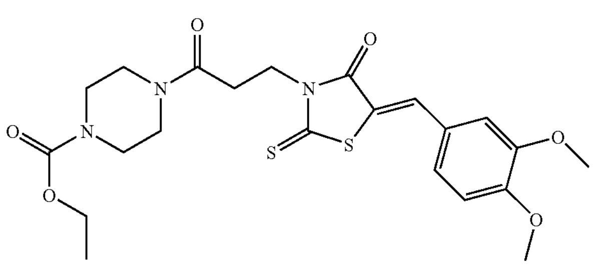 | >100 | >100 | 46.41 |

TABLE 6-continued

Inhibition of HIV-1 Integrase Catalytic Activities of Representative Compounds Exemplified by Formula 2

| Example | Structure | Inhibition of IN Catalytic Activities IC$_{50}$ (μM) | | GOLD Score |
|---|---|---|---|---|
| | | 3'-processing | Strand Transfer | |
| X220 | 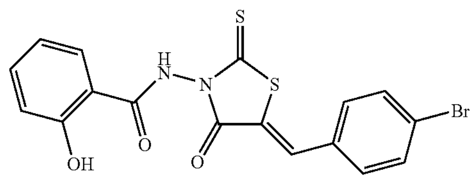 | 52 ± 11 | 27 ± 6 | 47.27 |
| X221 | 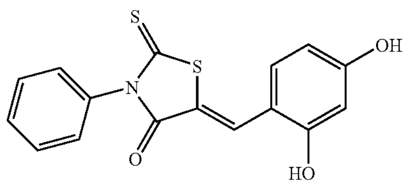 | >100 | >100 | 36.51 |
| X223 | 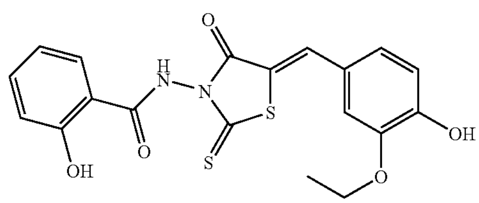 | 70 ± 27 | 38 ± 14 | 46.41 |
| X281 | 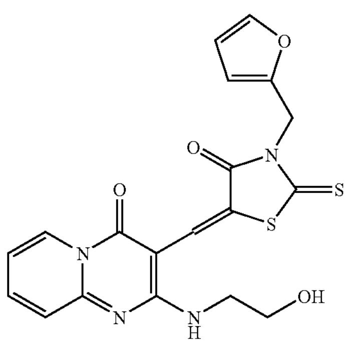 | >100 | 100 | 50.30 |
| OT35 | 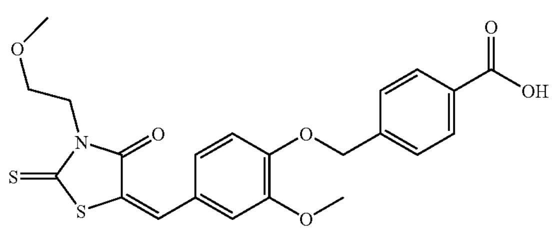 | 41 ± 11 | 38 ± 16 | 51 |
| OT3 | 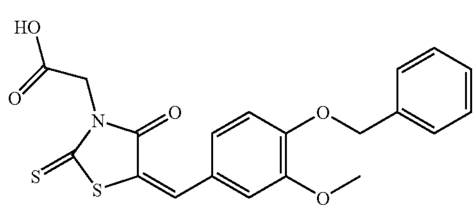 | >100 | 92 ± 7 | 50 |

TABLE 6-continued

Inhibition of HIV-1 Integrase Catalytic Activities of Representative Compounds Exemplified by Formula 2

| Example | Structure | 3'-processing | Strand Transfer | GOLD Score |
|---|---|---|---|---|
| OT4 | 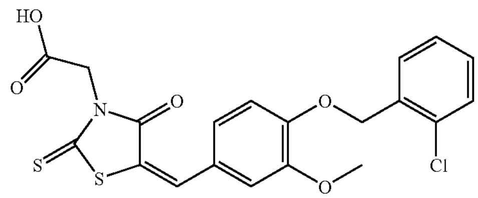 | 48 ± 7 | 22 ± 4 | 53 |
| OT5 | 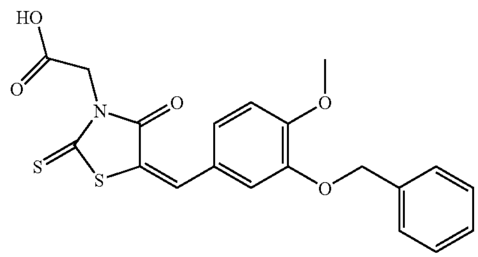 | >>100 | 54 ± 17 | 47 |
| OT6 | 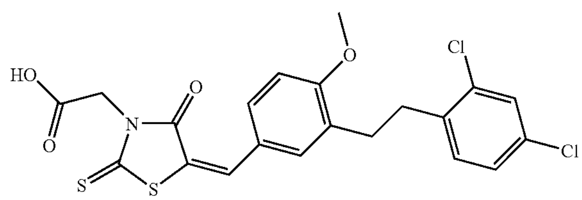 | 17 ± 4 | 13 ± 7 | 52 |
| OT9 | 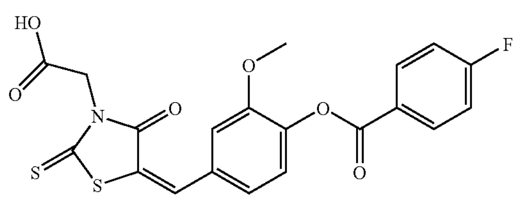 | >100 | 97 ± 5 | 51 |
| OT17 | 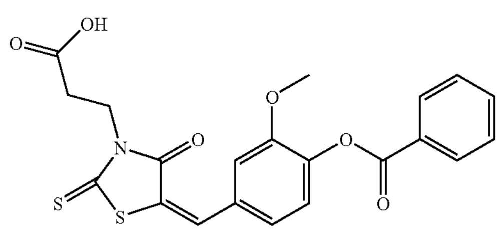 | 42 ± 20 | 27 ± 11 | 51 |
| OT35 | 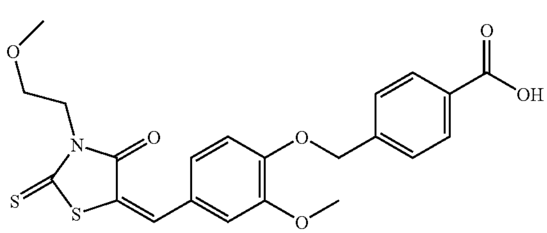 | 41 ± 11 | 38 ± 16 | 51 |

(Inhibition of IN Catalytic Activities IC$_{50}$ (μM))

TABLE 6-continued

Inhibition of HIV-1 Integrase Catalytic Activities of Representative Compounds Exemplified by Formula 2

| Example | Structure | 3'-processing | Strand Transfer | GOLD Score |
|---|---|---|---|---|
| OT37 | 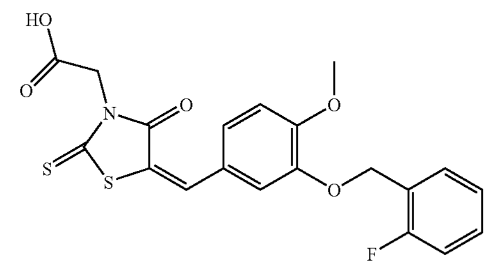 | >100 | 79 ± 8 | 50 |
| RT23 | 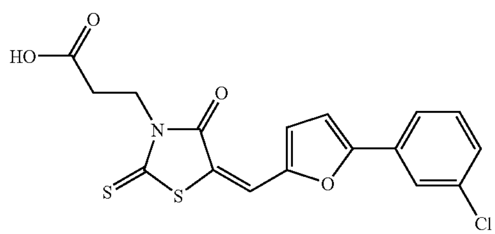 | >100 | 21 | |

TABLE 7

Inhibition of HIV-1 Integrase Catalytic Activities of Representative Compounds Exemplified by Formula 3

| Example | Structure | 3'-processing | Strand Transfer | GOLD Score |
|---|---|---|---|---|
| X71 | 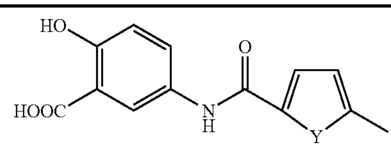 | >100 | >100 | 44.21 |
| X63 | 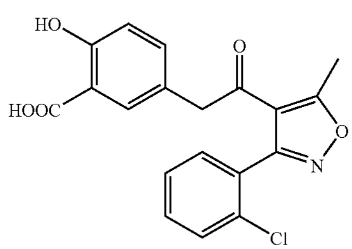 | 100 | 100 | 48.80 |
| X108 | 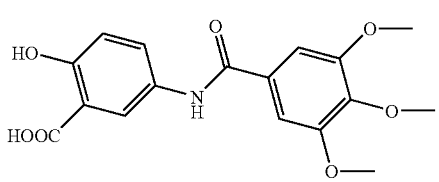 | >100 | >100 | 43.25 |

TABLE 7-continued

Inhibition of HIV-1 Integrase Catalytic Activities of Representative Compounds Exemplified by Formula 3

| Example | Structure | Inhibition of IN Catalytic Activities IC$_{50}$ (μM) | | GOLD Score |
|---|---|---|---|---|
| | | 3'-processing | Strand Transfer | |
| X114 | 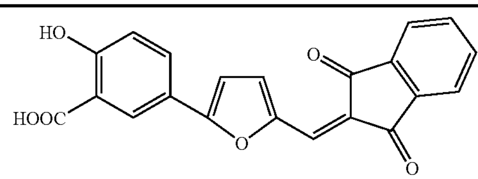 | 40 ± 10 | 43 ± 6 | 54.73 |
| X117 | 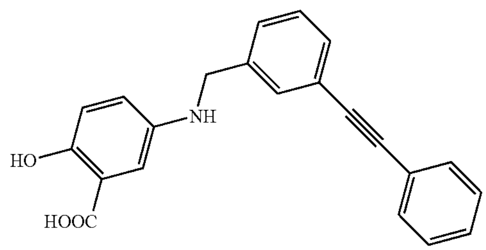 | 61 ± 10 | 32 ± 1 | 50.37 |
| X121 | 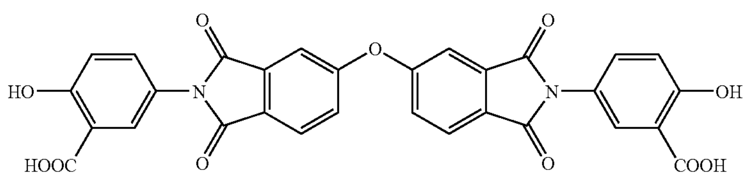 | 13 ± 6 | 12 ± 8 | 54.07 |
| X125 | 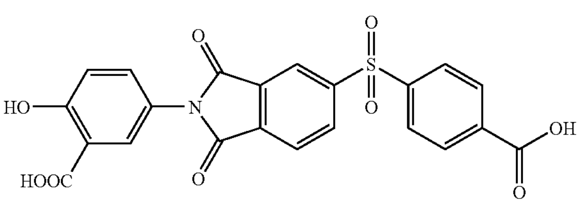 | 66 ± 6 | 44 ± 4 | 41.98 |
| X132 | 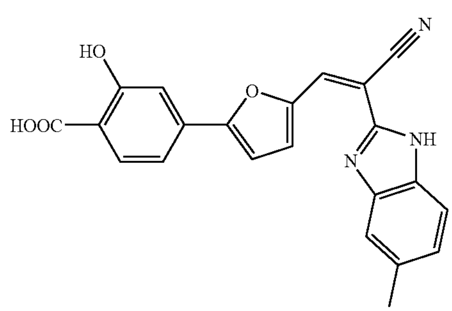 | 16 ± 5 | 8 ± 1 | 52.06 |
| X181 | 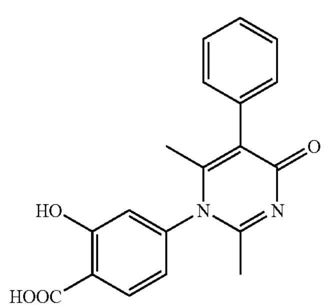 | 96 ± 7 | 73 ± 24 | 36.46 |

TABLE 7-continued

Inhibition of HIV-1 Integrase Catalytic Activities of Representative Compounds Exemplified by Formula 3

| Example | Structure | Inhibition of IN Catalytic Activities IC$_{50}$ (μM) | | GOLD Score |
|---|---|---|---|---|
| | | 3'-processing | Strand Transfer | |
| X196 | 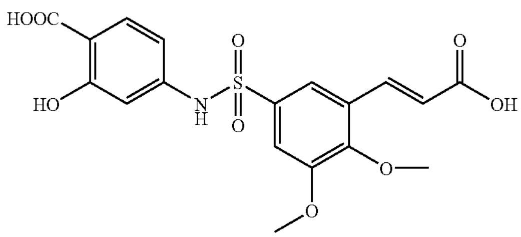 | 78 ± 39 | 75 ± 43 | 47.78 |
| X199 | 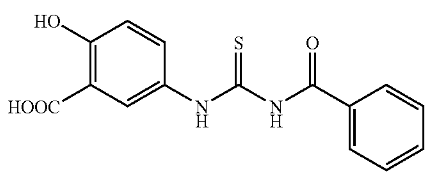 | >100 | >100 | 49.36 |

TABLE 8

HIV-1 Integrase Inhibitory Activities of Representative Compounds Exemplified by Formula 4

| Example | Structure | HIV-1 integrase Inhibitory Activities IC$_{50}$ (μM) | | GOLD Score |
|---|---|---|---|---|
| | | 3'-processing | Strand transfer | |
| X7 | 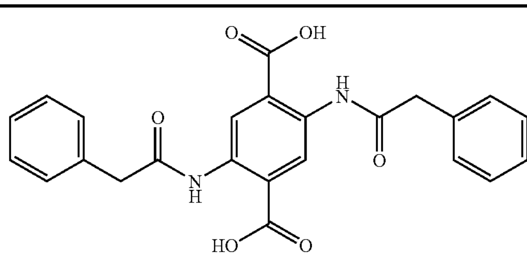 | 9 | 7 | 53 |
| X8 | 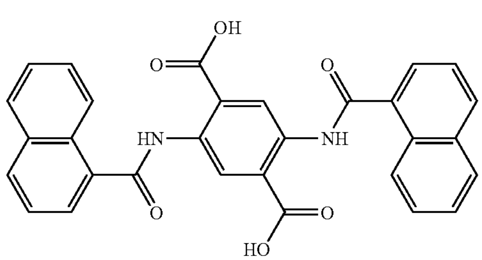 | 28 | 21 | 51 |

TABLE 8-continued

HIV-1 Integrase Inhibitory Activities of Representative Compounds Exemplified by Formula 4

| Example | Structure | HIV-1 integrase Inhibitory Activities IC$_{50}$ (μM) | | GOLD Score |
|---|---|---|---|---|
| | | 3'-processing | Strand transfer | |
| X19 | 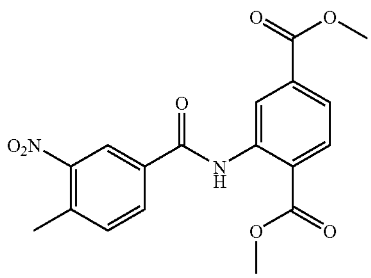 | 92 | 100 | |
| X35 | 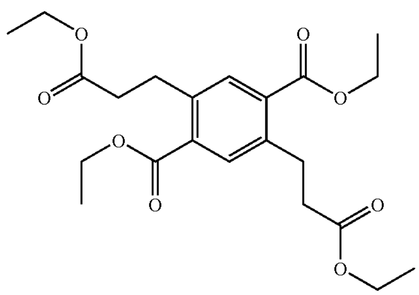 | 100 | 94 | |

TABLE 9

HIV-1 Integrase Inhibitory Activities of Representative Compounds Exemplified by Formula 5

| Example | Structure | HIV-1 integrase Inhibitory Activities IC$_{50}$ (μM) | | GOLD Score |
|---|---|---|---|---|
| | | 3'-processing | Strand transfer | |
| X228 | 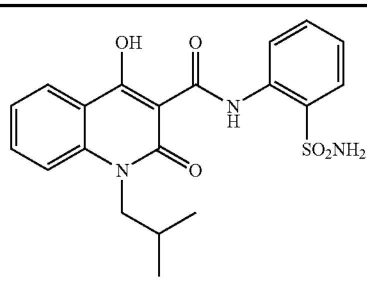 | 40 | 16 | 50 |
| XR8 | 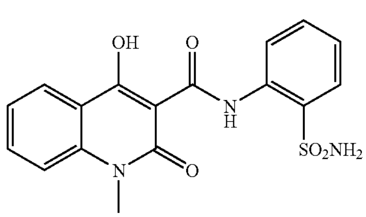 | 50 | 39 | |

TABLE 9-continued

HIV-1 Integrase Inhibitory Activities of Representative Compounds Exemplified by Formula 5

| Example | Structure | HIV-1 integrase Inhibitory Activities IC$_{50}$ (μM) | | GOLD Score |
|---|---|---|---|---|
| | | 3'-processing | Strand transfer | |
| XR7 | 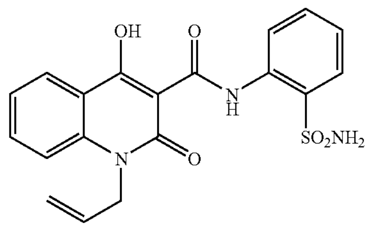 | 83 | 45 | |
| XR14 | 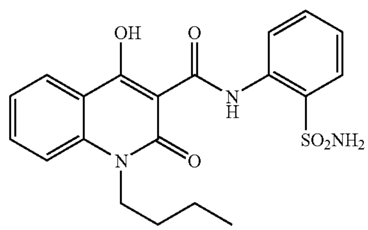 | 15 | 17 | |
| XR13 | 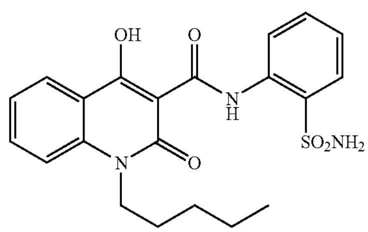 | 11 | 13 | |
| XR10 | 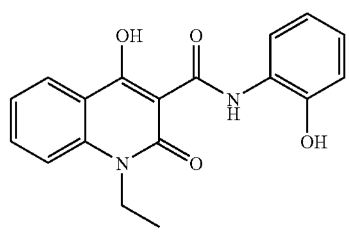 | 72 | 32 | |
| XR6 | 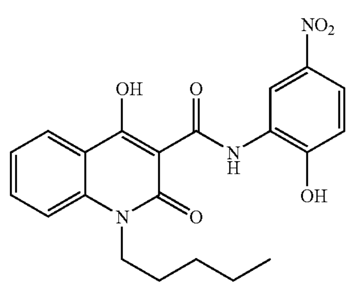 | 9 | 9 | |
| XR15 | 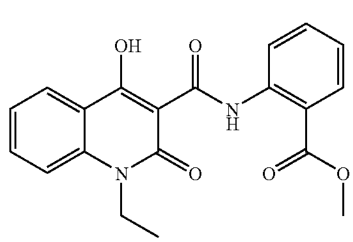 | 100 | 9.5 | |

TABLE 9-continued

HIV-1 Integrase Inhibitory Activities of Representative Compounds Exemplified by Formula 5

| Example | Structure | HIV-1 integrase Inhibitory Activities IC$_{50}$ (μM) 3'-processing | Strand transfer | GOLD Score |
|---|---|---|---|---|
| XR3 | 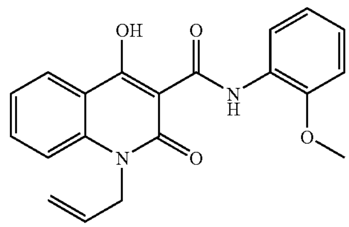 | 100 | 25 | |
| XR5 | 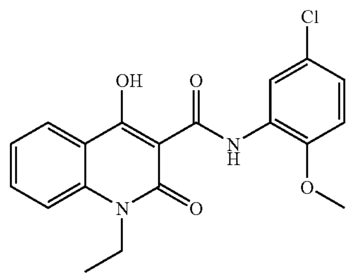 | 74 | 19 | |
| XR12 | 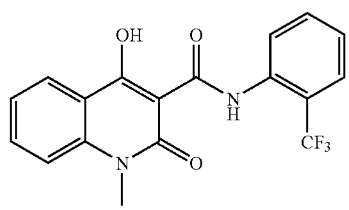 | 81 | 28 | |
| LM11 | 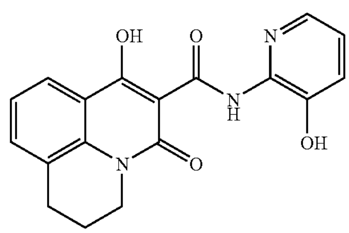 | 56 | 15 | |
| XR44 | 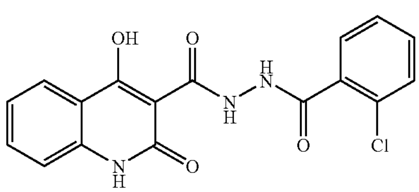 | 28 | 26 | |
| LM33 | 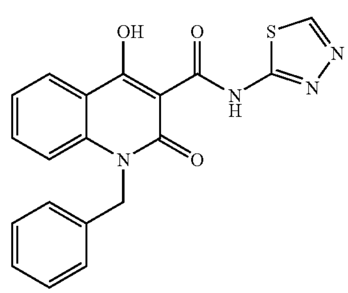 | 100 | 36 | |

TABLE 9-continued

HIV-1 Integrase Inhibitory Activities of Representative Compounds Exemplified by Formula 5

| Example | Structure | HIV-1 integrase Inhibitory Activities IC$_{50}$ (μM) | | GOLD Score |
|---|---|---|---|---|
| | | 3'-processing | Strand transfer | |
| NXR | [4-hydroxy-1-methyl-2-oxo-1,2-dihydroquinoline-3-carboxylic acid] | | | |

TABLE 10

Representative Compounds Exemplified by Formula 6

| Example | Structure | GOLD Score |
|---|---|---|
| NXR1 | [6-methoxy-4-hydroxy-1-isopropyl-2-oxo-1,2-dihydroquinoline-3-carboxylic acid] | 14 |
| NXR2 | [6-phenoxy-4-hydroxy-1-isopropyl-2-oxo-1,2-dihydroquinoline-3-carboxylic acid] | 24 |
| NXR3 | [6-benzyl-4-hydroxy-1-isopropyl-2-oxo-1,2-dihydroquinoline-3-carboxylic acid] | 23 |
| NXR4 | [6-(4-methoxybenzyl)-4-hydroxy-1-isopropyl-2-oxo-1,2-dihydroquinoline-3-carboxylic acid] | 35 |
| NXR5 | [6-(4-fluorobenzyl)-4-hydroxy-1-sec-butyl-2-oxo-1,2-dihydroquinoline-3-carboxylic acid] | 23 |
| NXR6 | [6-(4-fluorobenzyl)-4-hydroxy-1-pentyl-2-oxo-1,2-dihydroquinoline-3-carboxylic acid] | 39 |
| NXR7 | [6-(4-fluorobenzyl)-4-hydroxy-1-(1-hydroxymethylpropyl)-2-oxo-1,2-dihydroquinoline-3-carboxylic acid] | 23 |
| NXR8 | [5-amino-6-(4-fluorobenzyl)-4-hydroxy-1-(1-hydroxymethylpropyl)-2-oxo-1,2-dihydroquinoline-3-carboxylic acid] | 40 |
| NXR9 | [6-(4-fluorobenzyl)-4-hydroxy-1-sec-butyl-2-oxo-1,2-dihydro-1,8-naphthyridine-3-carboxylic acid] | 37 |
| NXR10 | [6-(4-fluorobenzyl)-4-hydroxy-1-(1-hydroxymethylpropyl)-2-oxo-1,2-dihydro-1,5-naphthyridine-3-carboxylic acid] | 21 |

TABLE 10-continued

Representative Compounds Exemplified by Formula 6

| Example | Structure | GOLD Score |
|---|---|---|
| NXR11 | 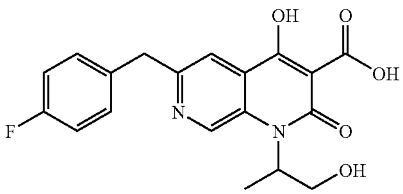 | 21 |
| NXR12 | 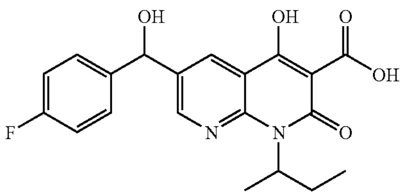 | 37 |
| NXR13 | 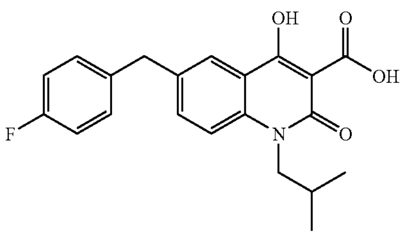 | 34 |
| NXR14 | 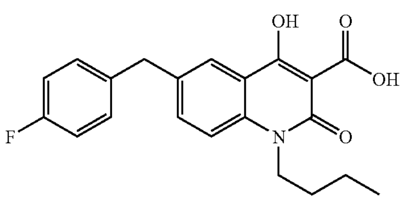 | 36 |

TABLE 11

Representative Compounds Exemplified by Formula 7

| Example | Structure | GOLD Score |
|---|---|---|
| COXR1 | | 33 |
| COXR2 | | 42 |
| COXR3 | | 43 |
| COXR4 | 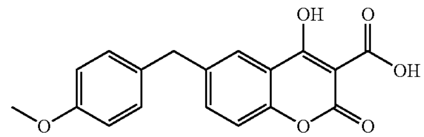 | 49 |
| COXR5 | 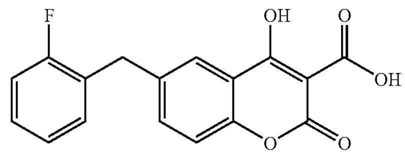 | 43 |
| COXR6 | 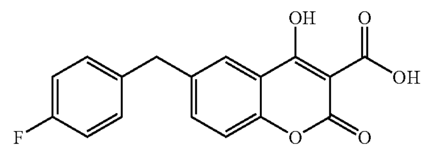 | 41 |
| COXR7 | 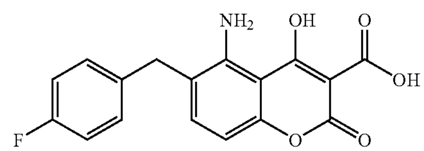 | 37 |
| COXR8 | 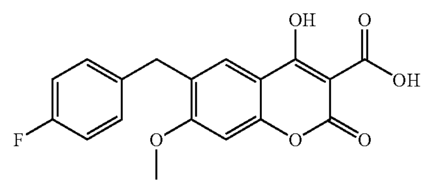 | 45 |
| COXR9 | 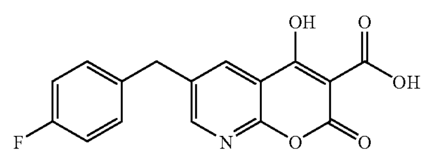 | 44 |
| COXR10 | 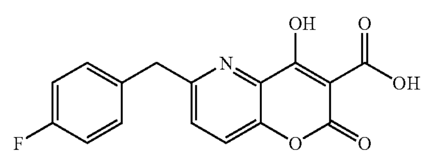 | 46 |
| COXR11 | 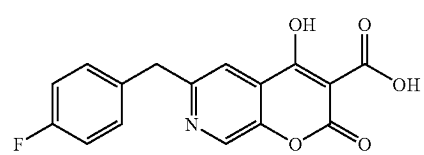 | 42 |
| COXR12 | 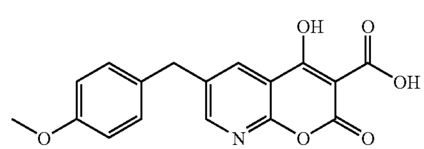 | 47 |

TABLE 11-continued

Representative Compounds Exemplified by Formula 7

| Example | Structure | GOLD Score |
|---|---|---|
| COXR13 | 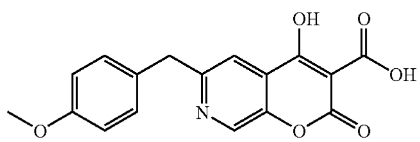 | 49 |
| COXR14 | 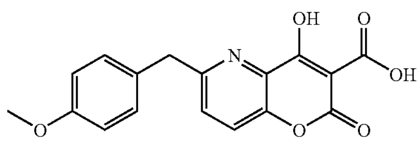 | 52 |
| COXR15 | 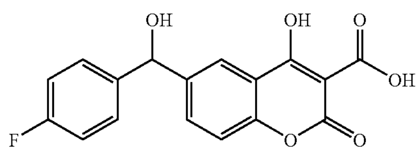 | 41 |
| COXR16 | 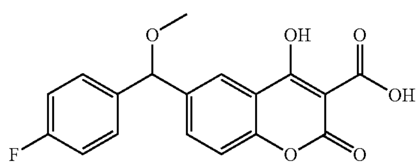 | 45 |

TABLE 12

Representative Compounds Exemplified by Formula 8

| Example | Structure | GOLD Score |
|---|---|---|
| CHOXR1 | | 35 |
| CHOXR2 | | 38 |
| CHOXR3 | | 41 |
| CHOXR4 | | 43 |

TABLE 12-continued

Representative Compounds Exemplified by Formula 8

| Example | Structure | GOLD Score |
|---|---|---|
| CHOXR5 | 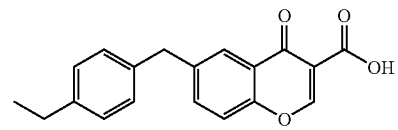 | 44 |
| CHOXR6 | 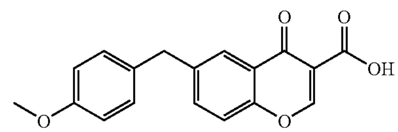 | 44 |
| CHOXR7 | 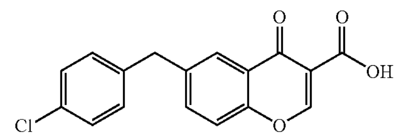 | 41 |
| CHOXR8 | 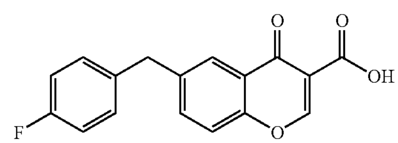 | 39 |
| CHOXR9 | 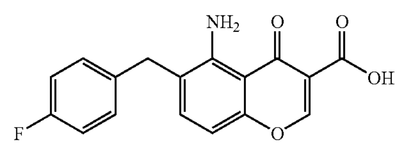 | 40 |
| CHOXR10 | 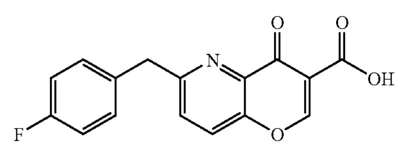 | 43 |
| CHOXR11 | 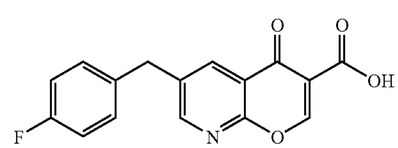 | 42 |
| CHOXR12 | 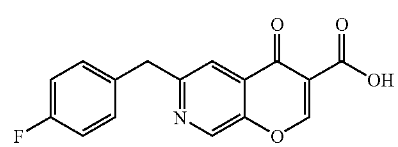 | 44 |
| CHOXR13 | 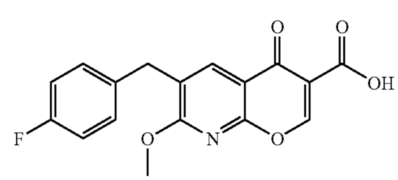 | 42 |
| CHOXR14 | 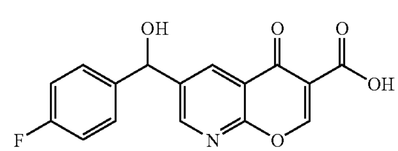 | 39 |

TABLE 12-continued

Representative Compounds Exemplified by Formula 8

| Example | Structure | GOLD Score |
|---------|-----------|------------|
| CHOXR15 | (structure) | 42 |

TABLE 13

Representative Compounds Exemplified by Formula 9

| Example | Structure | GOLD Score |
|---------|-----------|------------|
| MXR1 | (structure) | 33 |
| MXR2 | (structure) | 26 |
| MXR3 | (structure) | 31 |
| MXR4 | (structure) | 29 |
| MXR5 | (structure) | 36 |

TABLE 13-continued

Representative Compounds Exemplified by Formula 9

| Example | Structure | GOLD Score |
|---------|-----------|------------|
| MXR6 | (structure) | 30 |
| MXR7 | (structure) | 33 |
| MXR8 | (structure) | 32 |
| MXR9 | (structure) | 35 |
| MXR10 | (structure) | 29 |
| MXR11 | (structure) | 41 |
| MXR12 | (structure) | 38 |

TABLE 13-continued

Representative Compounds Exemplified by Formula 9

| Example | Structure | GOLD Score |
|---------|-----------|------------|
| MXR13 | 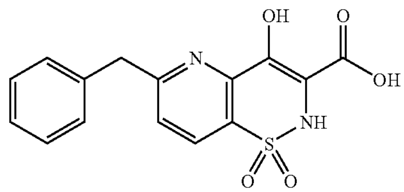 | 53 |
| MXR14 | 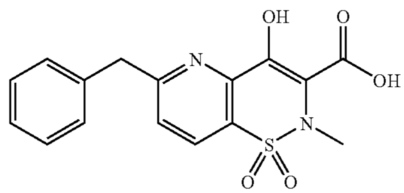 | 48 |
| MXR15 | 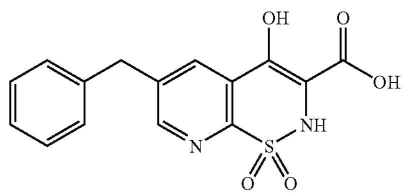 | 48 |
| MXR16 | 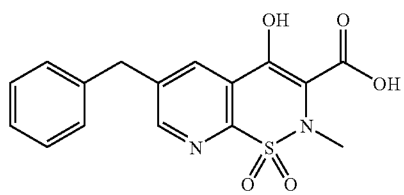 | 43 |
| MXR17 | 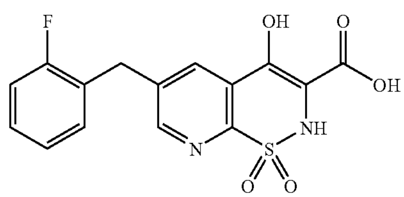 | 48 |
| MXR18 | 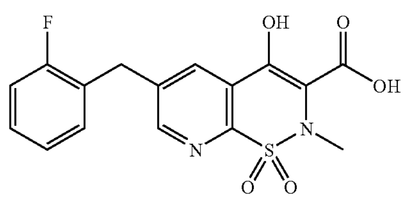 | 42 |
| MXR19 | 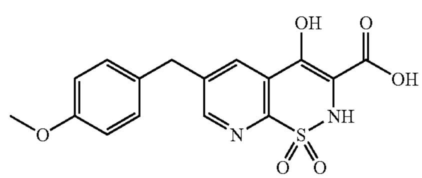 | 42 |
| MXR20 | 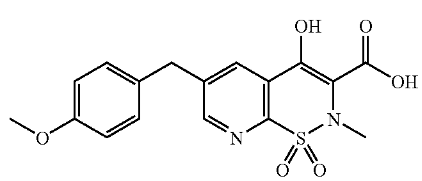 | 42 |
| MXR21 | | 49 |
| MXR22 | | 49 |
| MXR23 | | 35 |
| MXR24 | | 32 |
| MXR25 | | 32 |
| MXR26 | | 30 |

TABLE 14

HIV-1 IN Inhibitory Activities of Representative Compounds Exemplified by Formula 10

| Example | Structure | 3'-processing | Strand transfer | GOLD Score |
|---------|-----------|---------------|-----------------|------------|
| ROM3 | | >12 | 12 | 28 |
| ROM3A1 | | >100 | >100 | 32 |
| ROM3A2 | | 94 | 98 | 28 |
| ROM3A3 | | >100 | >100 | 33 |
| ROM3A4 | | 64 | 59 | 42 |

HIV-1 IN Inhibitory Activities IC$_{50}$ (μM)

TABLE 14-continued

HIV-1 IN Inhibitory Activities of Representative Compounds Exemplified by Formula 10

| Example | Structure | HIV-1 IN Inhibitory Activities IC$_{50}$ (μM) 3'-processing | Strand transfer | GOLD Score |
|---|---|---|---|---|
| ROM3A5 | 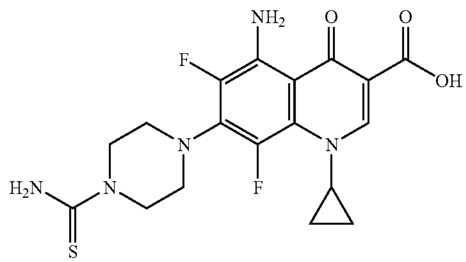 | >100 | >100 | 38 |
| ROM3A7 | 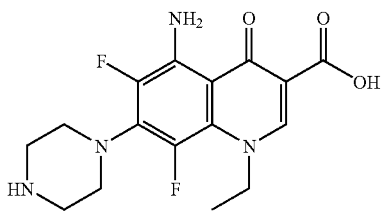 | >100 | 95 | 27 |
| ROM3A6 | 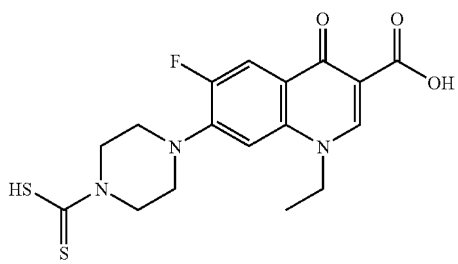 | >100 | >100 | 32 |
| ROM3A8 | 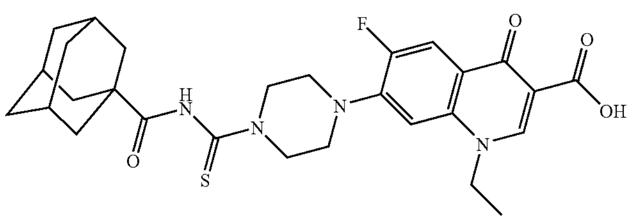 | 78 | 74 | 36 |
| ROM3A9 | 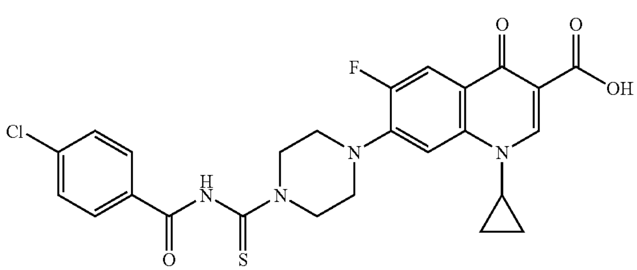 | 80 | 53 | 43 |
| ROM3A10 | 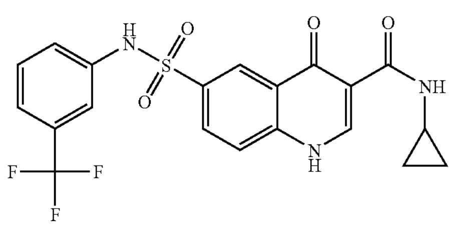 | 93 | 92 | 40 |

TABLE 14-continued

HIV-1 IN Inhibitory Activities of Representative Compounds Exemplified by Formula 10

| Example | Structure | HIV-1 IN Inhibitory Activities IC$_{50}$ (µM) 3'-processing | Strand transfer | GOLD Score |
|---|---|---|---|---|
| ROM3A11 | 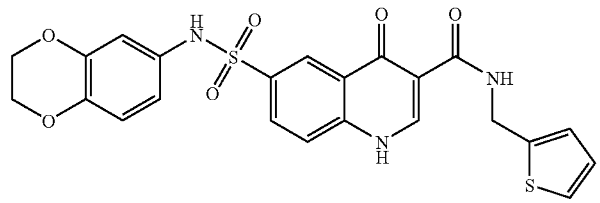 | 91 | 90 | 59 |
| SR9 | 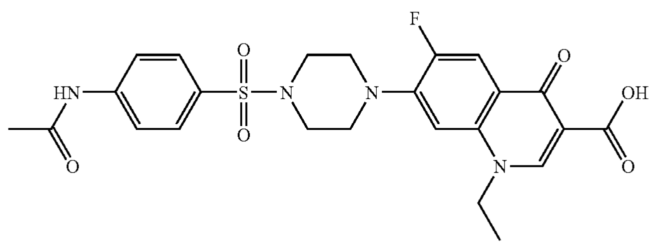 | >100 | >100 | 39 |

TABLE 15

HIV-1 Integrase Inhibitory Activities of Representative Compounds Exemplified by Formula 11

| Example | Structure | HIV-1 IN Inhibitory Activities 3'-processing | Strand transfer |
|---|---|---|---|
| ROM1 | 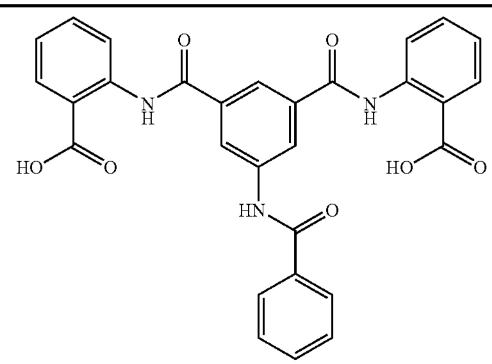 | 78 | 20 |
| ANA1CD | 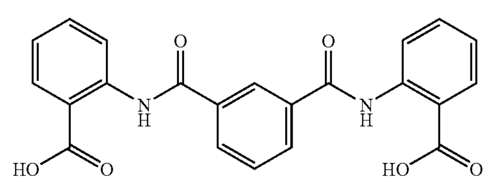 | | |
| ANA2CD | 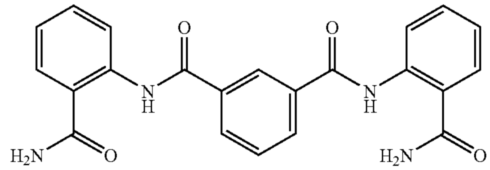 | | |

TABLE 15-continued

HIV-1 Integrase Inhibitory Activities of Representative Compounds
Exemplified by Formula 11

| Example | Structure | HIV-1 IN Inhibitory Activities | |
|---|---|---|---|
| | | 3'-processing | Strand transfer |
| ANA3CD | 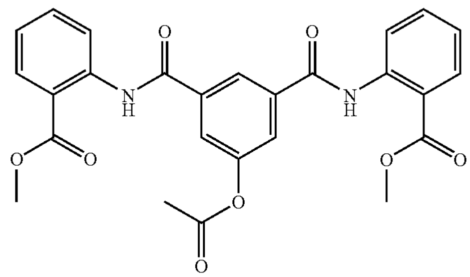 | | |
| ANA4CD | 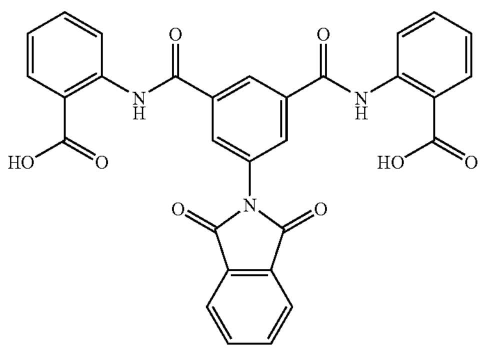 | | |
| ANA5CD | 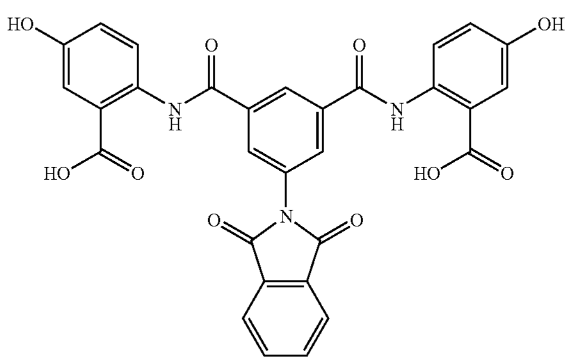 | | |
| ANA6-AS | 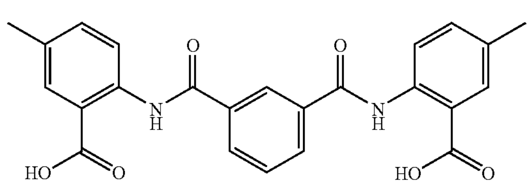 | | |

TABLE 16

HIV-1 Integrase Inhibitory Activities of Representative Compounds Exemplified by Formula 12

| Example | Structure | HIV-1 IN Inhibitory Activities IC$_{50}$ (μM) | | GOLD Score |
|---|---|---|---|---|
| | | 3'-processing | Strand transfer | |
| AV15 | | 9 | 4 | 34 |
| AV30 | | 10 | 4 | |
| X114 | | 40 | 43 | 45 |
| SA1 | | 59 | 9 | 45 |
| NST20 | | 100 | 68 | 55 |

TABLE 16-continued

HIV-1 Integrase Inhibitory Activities of Representative Compounds Exemplified by Formula 12

| Example | Structure | HIV-1 IN Inhibitory Activities IC$_{50}$ (µM) | | GOLD Score |
|---|---|---|---|---|
| | | 3'-processing | Strand transfer | |
| NAV1 | 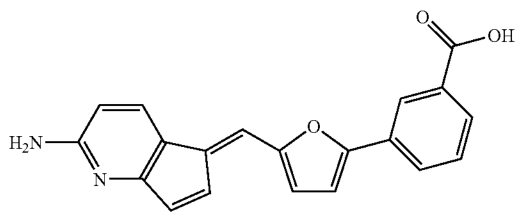 | | | 48 |
| NAV2 | 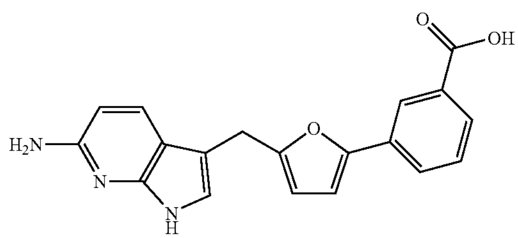 | | | 56 |
| NAV3 | 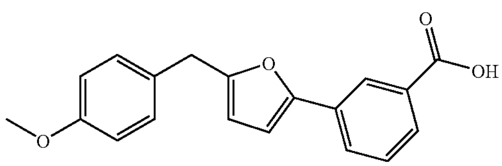 | | | 45 |
| NAV4 | 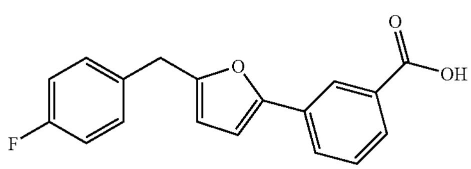 | | | 40 |
| NAV5 | 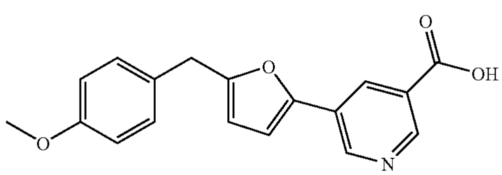 | | | 42 |
| NAV6 | 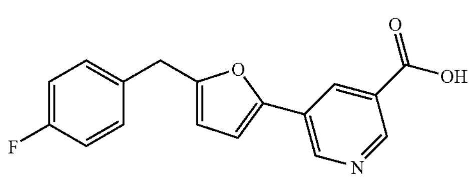 | | | 41 |
| NAV7 | 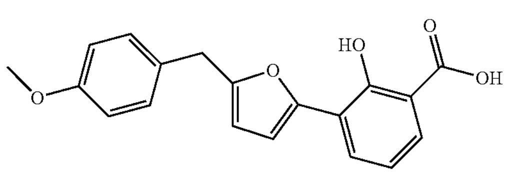 | | | 50 |

TABLE 16-continued

HIV-1 Integrase Inhibitory Activities of Representative Compounds Exemplified by Formula 12

| Example | Structure | HIV-1 IN Inhibitory Activities IC$_{50}$ (μM) | | GOLD Score |
|---|---|---|---|---|
| | | 3'-processing | Strand transfer | |
| NAV8 | 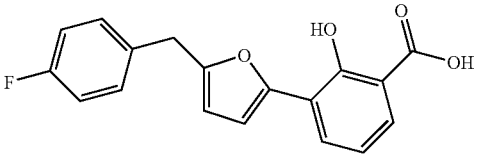 | | | 50 |
| NAV9 | 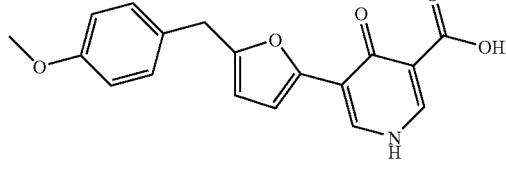 | | | 45 |
| NAV10 | 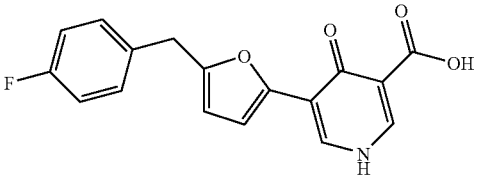 | | | 42 |
| NAV11 | 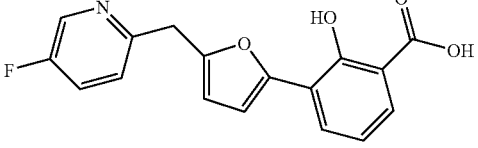 | | | 48 |
| NAV12 | 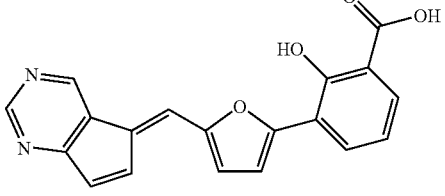 | | | 48 |

TABLE 17

HIV-1 Integrase Inhibitory Activities of Representative Compounds Exemplified by Formula 13

| Example | Structure | HIV-1 IN Inhibitory Activities | | GOLD Score |
|---|---|---|---|---|
| | | 3'-processing | Strand transfer | |
| X155 | 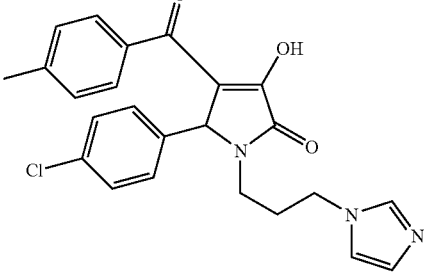 | 93 | 67 | 51 |

TABLE 17-continued

HIV-1 Integrase Inhibitory Activities of Representative Compounds Exemplified by Formula 13

| Example | Structure | HIV-1 IN Inhibitory Activities | | GOLD Score |
|---|---|---|---|---|
| | | 3'-processing | Strand transfer | |
| X81 | | 84 | 69 | |
| X36 | | >100 | >100 | |
| T38 | | 25 | 20 | |
| MMC8 | | >1000 | 395 | |

TABLE 18

Inhibition of HIV-1 Integrase Catalytic Activities of Representative Compounds Exemplified by Formula 14

| Example | Structure | Inhibition of IN catalytic activities, IC$_{50}$ (μM) | |
| --- | --- | --- | --- |
| | | 3'-processing | Strand transfer |
| RT35 | | 90 | 19 |
| RT42 | | >100 | >100 |

TABLE 19

HIV-1 Integrase Inhibitory Activities of Representative Compounds Exemplified by Formula 15

| Example | Structure | HIV-1IN Inhibitory Activities | | GOLD Score |
| --- | --- | --- | --- | --- |
| | | 3'-processing | Strand transfer | |
| X88 | | >100 | 79 | 61 |

TABLE 20

HIV-1 Integrase Inhibitory Activities of Representative Compounds Exemplified by Formula 16

| Example | Structure | HIV-1IN Inhibitory Activities | | GOLD Score |
|---|---|---|---|---|
| | | 3'-processing | Strand transfer | |
| X111 | [structure] | 88 | 68 | 55 |

TABLE 21

HIV-1 Integrase Inhibitoiy Activities of Representative Compounds Exemplified by Formula 17

| Example | Structure | HIV-1IN Inhibitory Activities | | GOLD Score |
|---|---|---|---|---|
| | | 3'-processing | Strand transfer | |
| X115 | [structure] | 42 | 28 | 50 |

TABLE 22

HIV-1 Integrase Inhibitory Activities of Representative Compounds Exemplified by Formula 18

| Example | Structure | HIV-1IN Inhibitory Activities | | GOLD Score |
|---|---|---|---|---|
| | | 3'-processing | Strand transfer | |
| X134 | [structure] | >100 | 90 | 51 |

TABLE 23

HIV-1 Integrase Inhibitory Activities of Representative Compounds Exemplified by Formula 19

| Example | Structure | HIV-1IN Inhibitory Activities | | GOLD |
|---|---|---|---|---|
| | | 3'-processing | Strand transfer | Score |
| X143 | (6-methoxycoumarin-3-yl thiazole hydrazone with 2-hydroxybenzylidene) | 30 | 10 | 53 |
| X144 | (6-methoxycoumarin-3-yl thiazole hydrazone with furan-2-ylmethylene) | 78 | 29 | |

TABLE 24

HIV-1 Integrase Inhibitory Activities of Representative Compounds Exemplified by Formula 20

| Example | Structure | HIV-1IN Inhibitory Activities | |
|---|---|---|---|
| | | 3'-processing | Strand transfer |
| X148 | (2-carboxyphenyl benzamide with 3-nitrophenyl sulfonamide) | 89 | 90 |

TABLE 25

HIV-1 Integrase Inhibitory Activities of Representative Compounds Exemplified by Formula 21

| Example | Structure | HIV-1IN Inhibitory Activities | | GOLD |
|---|---|---|---|---|
| | | 3'-processing | Strand transfer | Score |
| X159 | (4-chlorocinnamamide-phenyl-furan-2-carboxamide) | 90 | 91 | 47 |

TABLE 26

HIV-1 Integrase Inhibitory Activities of Representative Compounds Exemplified by Formula 22

| Example | Structure | HIV-1IN Inhibitory Activities | | GOLD Score |
|---|---|---|---|---|
| | | 3'-processing | Strand transfer | |
| X160 | (structure) | 16 | 17 | 46.08 |

TABLE 27

HIV-1 Integrase Inhibitory Activities of Representative Compounds Exemplified by Formula 23

| Example | Structure | HIV-1IN Inhibitory Activities | | GOLD Score |
|---|---|---|---|---|
| | | 3'-processing | Strand transfer | |
| X182 | (structure) | 88 | 56 | 52 |

TABLE 28

HIV-1 Integrase Inhibitory Activities of Representative Compounds Exemplified by Formula 24

| Example | Structure | HIV-1IN Inhibitory Activities | | GOLD Score |
|---|---|---|---|---|
| | | 3'-processing | Strand transfer | |
| X205 | (structure) | 57 | 28 | 52 |

TABLE 29

HIV-1 Integrase Inhibitory Activities of Representative Compounds Exemplified by Formula 25

| Example | Structure | HIV-1IN Inhibitory Activities | | GOLD Score |
|---|---|---|---|---|
| | | 3'-processing | Strand transfer | |
| X208 | [structure] | 97 | 61 | 43 |

TABLE 30

HIV-1 Integrase Inhibitory Activities of Representative Compounds Exemplified by Formula 26

| Example | Structure | HIV-1IN Inhibitory Activities | | GOLD Score |
|---|---|---|---|---|
| | | 3'-processing | Strand transfer | |
| X218 | [structure] | 76 | 56 | 40 |

TABLE 31

HIV-1 Integrase Inhibitory Activities of Representative Compounds Exemplified by Formula 27

| Example | Structure | HIV-1IN Inhibitory Activities | | GOLD Score |
|---|---|---|---|---|
| | | 3'-processing | Strand transfer | |
| X219 | [structure] | 89 | 31 | 52 |

TABLE 32

HIV-1 Integrase Inhibitory Activities of Representative Compounds Exemplified by Formula 28

| Example | Structure | HIV-1 IN Inhibitory Activities | | GOLD Score |
|---|---|---|---|---|
| | | 3'-processing | Strand transfer | |
| X234 | 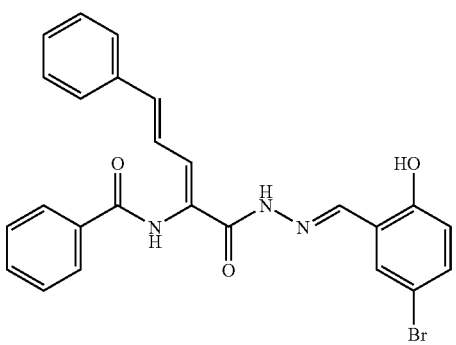 | 90 | 23 | 55 |
| X231 | 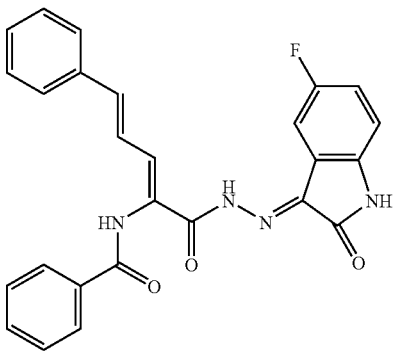 | 60 | 38 | 42 |

TABLE 33

HIV-1 Integrase Inhibitory Activities of Representative Compounds Exemplified by Formula 29

| Example | Structure | HIV-1 IN Inhibitory Activities | | GOLD Score |
|---|---|---|---|---|
| | | 3'-processing | Strand transfer | |
| X244 | 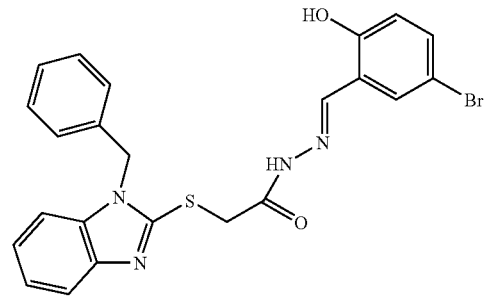 | 88 | 68 | 55 |

TABLE 34
HIV-1 Integrase Inhibitory Activities of Representative Compounds Exemplified by Formula 30
| Example | Structure | HIV-1IN Inhibitory Activities | |
|---|---|---|---|
| | | 3'-processing | Strand transfer |
| X255 | 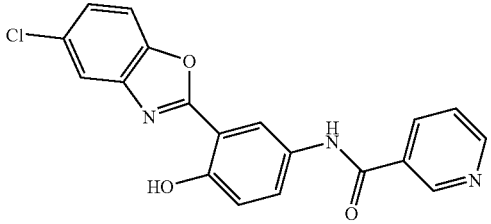 | 61 | 10 |
| XR16 | 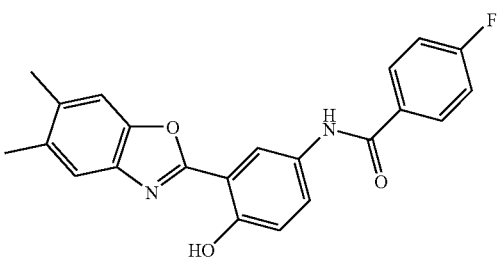 | <100 | <100 |
| XR17 | 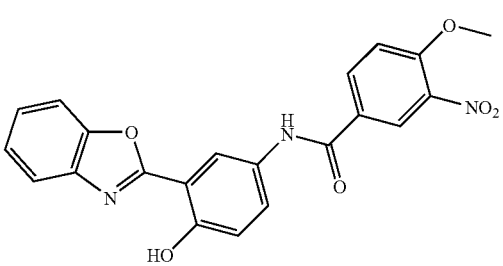 | 6 | 7 |
| XR18 | 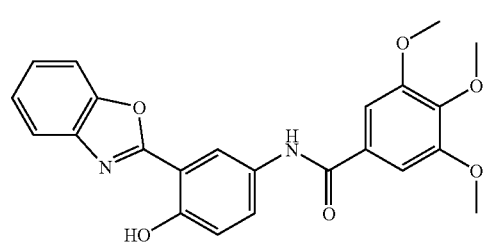 | <100 | <100 |
| XR19 | 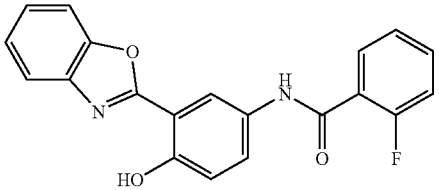 | <100 | <100 |
| XR21 | 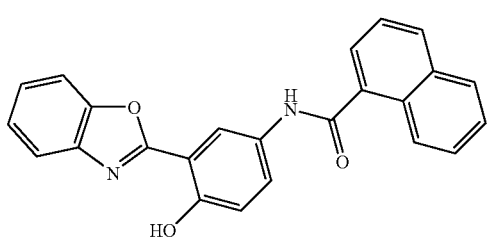 | 14 | 6 |

TABLE 34-continued

HIV-1 Integrase Inhibitory Activities of Representative Compounds Exemplified by Formula 30

| Example | Structure | HIV-1IN Inhibitory Activities | |
|---|---|---|---|
| | | 3'-processing | Strand transfer |
| XR22 | | <100 | <100 |
| X257 | | 99 | 80 |

TABLE 35

HIV-1 Integrase Inhibitory Activities of Representative Compounds Exemplified by Formula 31

| Example | Structure | HIV-1IN Inhibitory Activities | | GOLD |
|---|---|---|---|---|
| | | 3'-processing | Strand transfer | Score |
| X272 | | 34 | 24 | 59 |

TABLE 36

HIV-1 Integrase Inhibitory Activities of Representative Compounds Exemplified by Formula 32

| Example | Structure | HIV-1IN Inhibitory Activities | | GOLD |
|---|---|---|---|---|
| | | 3'-processing | Strand transfer | Score |
| X278 | | 89 | 38 | 49 |

TABLE 37

HIV-1 Integrase Inhibitory Activities of Representative Compounds Exemplified by Formula 33

| Example | Structure | HIV-1 IN Inhibitory Activities | | GOLD Score |
|---|---|---|---|---|
| | | 3'-processing | Strand transfer | |
| X279 | | 95 | 59 | 61 |

TABLE 38

HIV-1 Integrase Inhibitory Activities of Representative Compounds Exemplified by Formula 34

| Example | Structure | HIV-1 IN Inhibitory Activities | | GOLD Score |
|---|---|---|---|---|
| | | 3'-processing | Strand transfer | |
| X280 | | >1000 | 85 | 54 |

TABLE 39

Inhibition of HIV-1 Integrase Catalytic Activities and GOLD Score of Representative Compounds Exemplified by Formula 35

| Example | Structure | Inhibition of IN catalytic activities, $IC_{50}$ (µM) | | GOLD Score |
|---|---|---|---|---|
| | | 3'-processing | Strand transfer | |
| OT51 | | 36 ± 29 | 14 ± 4 | 56 |

TABLE 40

Inhibition of HIV-1 Integrase Catalytic Activities and GOLD Score of Representative Compounds Exemplified by Formula 36

| Example | Structure | Inhibition of IN catalytic activities, IC$_{50}$ (μM) | | GOLD Score |
|---|---|---|---|---|
| | | 3'-processing | Strand transfer | |
| OT27 | 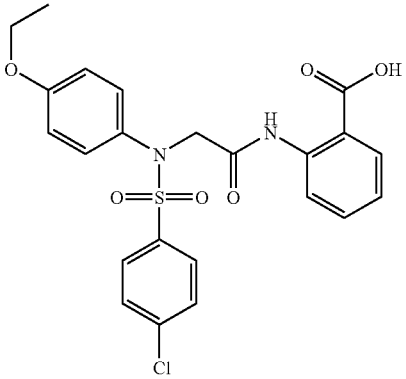 | 69 ± 15 | 47 ± 22 | 38 |
| OT24 | 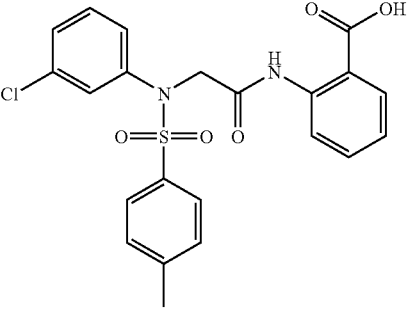 | 98 ± 5 | 71 ± 23 | 36 |

TABLE 41

Inhibition of HIV-1 Integrase Catalytic Activities and GOLD Score of Representative Compounds Exemplified by Formula 37

| Example | Structure | Inhibition of IN catalytic activities, IC$_{50}$ (μM) | | GOLD Score |
|---|---|---|---|---|
| | | 3'-processing | Strand transfer | |
| OT33 | 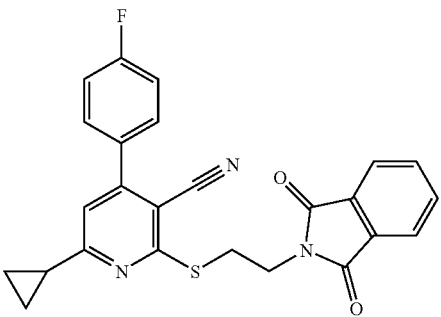 | >>100 | 95 ± 11 | 64 |

TABLE 42

Inhibition of HIV-1 Integrase Catalytic Activities and GOLD Score of Representative Compounds Exemplified by Formula 38

| Example | Structure | Inhibition of IN catalytic activities, $IC_{50}$ (μM) | | GOLD Score |
|---|---|---|---|---|
| | | 3'-processing | Strand transfer | |
| OT8 | | 31 ± 16 | 14 ± 4 | 41 |

TABLE 43

Inhibition of HIV-1 Integrase Catalytic Activities and GOLD Score of Representative Compounds Exemplified by Formula 39

| Example | Structure | Inhibition of IN catalytic activities, $IC_{50}$ (μM) | | GOLD Score |
|---|---|---|---|---|
| | | 3'-processing | Strand transfer | |
| OT32 | | 72 ± 8 | 57 ± 22 | 47 |
| SR44 | | 32 | | 16 |

TABLE 44

Inhibition of HIV-1 Integrase Catalytic Activities and GOLD Score of Representative Compounds Exemplified by Formula 40

| Example | Structure | Inhibition of IN catalytic activities, $IC_{50}$ (μM) | | GOLD Score |
|---|---|---|---|---|
| | | 3'-processing | Strand transfer | |
| OT2 | 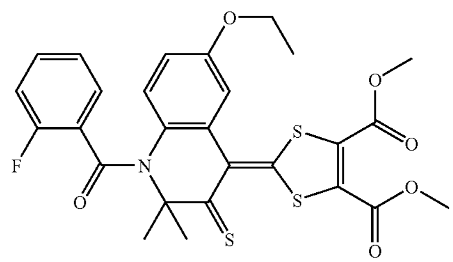 | >100 | 95 ± 9 | 36 |
| RT25 | 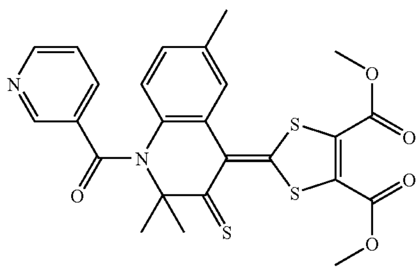 | >100 | 100 | |

TABLE 45

Inhibition of HIV-1 Integrase Catalytic Activities of Representative Compounds Exemplified by Formula 41

| Example | Structure | Inhibition of IN catalytic activities, $IC_{50}$ (μM) | |
|---|---|---|---|
| | | 3'-processing | Strand transfer |
| RT3 | 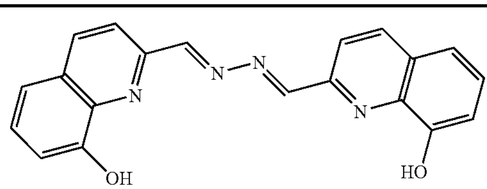 | 45 | 69 |
| RT29 | 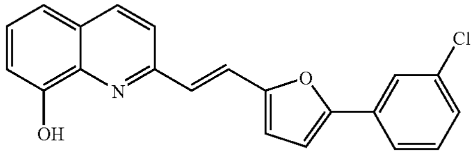 | 30 | 70 |
| RT31 | 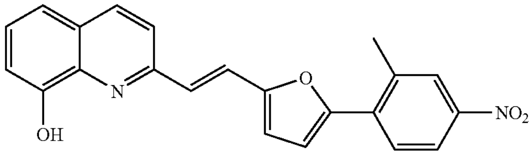 | 57 | >100 |

TABLE 45-continued

Inhibition of HIV-1 Integrase Catalytic Activities of
Representative Compounds Exemplified by Formula 41

| Example | Structure | Inhibition of IN catalytic activities, $IC_{50}$ ($\mu$M) | |
|---|---|---|---|
| | | 3'-processing | Strand transfer |
| RT30 | *[structure: fluorophenyl-(pyridin-2-ylamino)methyl-substituted 8-hydroxy-2-methylquinoline]* | >100 | >100 |

Pharmacophore Models: Several common feature pharmacophore models were generated using a set of known HIV-1 integrase inhibitors. The top-ranking pharmacophores are expected to identify the hypothetical orientation of the active compounds and the common binding features interacting with the target. All training set inhibitors were somewhat structurally diverse but possessed some common chemical features, and comparable inhibitory potencies. The pharmacophore models were generated using low energy conformation as well as using conformations similar to the crystallographically determined conformation of known integrase inhibitors. On the basis of the structural information from these known inhibitors and the active site of the HIV-1 integrase, a set of features were selected to be present in the pharmacophore generation experiment. The chemical features considered in the pharmacophore model generation run were H-bond donor (HBD), H-bond acceptor (HBA), Hydrophobic aromatic (HRA), Aromatic ring center (AR), and Negatively ionizable (NI) features. The most potent known HIV-1 integrase inhibitor (GS-9137 (5)) is mapped onto the best ranked pharmacophore model. All the pharmacophore models that were generated specific to HIV-1 integrase are given in Table 46 along with feature combinations and ranking scores.

Database Search: The highest ranked common feature pharmacophore model 1 was used as search query to retrieve compounds with novel chemical structure and desired chemical features from an in-house multi-conformer Catalyst-formatted database consisting of ~5,000,000 compounds. Drug-like properties of the retrieved hits from the database search were calculated using Accord for Excel.

Docking and Virtual Screening: The subunit B of the core domain X-ray structure of Integrase (PDB 1BIS) in which all the active site amino acid residues were resolved was chosen for our docking and virtual screening purpose. A $Mg^{2+}$ ion was placed in the active site between carboxylate oxygen atoms of amino acid residues D64 and D116 considering the geometry of the $Mg^{2+}$ ion that was present in the subunit A of IN in PDB 1BIS and subunit A in IN-5CITEP complex X-ray structure (PDB 1SQ4). All the water molecules present in protein were removed and proper protonation states were assigned for acidic and basic residues of the protein. Docking was performed using version 1.2 of the GOLD (Genetic Optimization for Ligand Docking) software package. GOLD is an automated ligand docking program that uses a genetic algorithm to explore the full range of ligand conformational flexibility with partial flexibility of the receptor. The algorithm was tested on a dataset of over 300 complexes extracted from the Brookhaven Protein DataBank. GOLD succeeded in more than 70% cases in reproducing the experimental bound conformation of the ligand. GOLD requires a user defined binding site. It searches for a cavity within the defined area and considers all the solvent accessible atoms in the defined area as active site atoms. A 20 A radius active site was defined considering the carboxylate oxygen (OD1) atom of residue D64 as the center of the active site. All the compounds retrieved by the pharmacophore models were docked into the active site of IN. On the basis of the GOLD fitness score, for each molecule a bound conformation with high fitness score was considered as the best bound-conformation. All docking runs were carried out using standard default settings with a population size of 100, a maximum number of 100,000 operations, and a mutation and crossover rate of 95. The fitness function that was implemented in GOLD consisted basically of H-bonding, complex energy and ligand internal energy terms.

Materials, Chemicals, and Enzymes: All compounds were dissolved in DMSO and the stock solutions were stored at −20° C. The [$^{32}$P]-ATP was purchased from either Amersham Biosciences or ICN.

Preparation of Oligonucleotide. Substrates: The oligonucleotides 21 top, 5'-GTGTGGAAAATCTCTAGCAGT-3' (SEQ ID NO:1) and 21 bot, 5'-ACTGCTAGAGATTTTCCACAC-3' (SEQ ID NO:2) were purchased from Norris Cancer Center Core Facility (University of Southern California) and purified by UV shadowing on polyacrylamide gel. To analyze the extent of 3'-processing and strand transfer using 5'-end labeled substrates, 21 top was 5'-end labeled using T4 polynucleotide kinase (Epicentre, Madison, Wis.) and γ [$^{32}$P]-ATP (Amersham Biosciences OT ICN). The kinase was heat-inactivated and 21 bot was added in 1.5-molar excess. The mixture was heated at 95° C., allowed to cool slowly to room temperature, and run through a spin 25 mini-column (USA Scientific) to separate annealed double-stranded oligonucleotide from unincorporated material.

Integrase Assays: To determine the extent of 3-processing and strand transfer, wild-type IN was preincubated at a final concentration of 200 nM with the inhibitor in reaction buffer (50 mM NaCl, 1 mM HEPES, pH 7.5, 50 µM EDTA, 50 µM dithiothreitol, 10% glycerol (w/v), 7.5 mM MnC12, 0.1 mg/ml bovine serum albumin, 10 mM 2-mercaptoethanol, 10% dimethyl sulfoxide, and 25 µM MOPS, pH 7.2) at 30° C. for 30 min. Then, 20 nM of the 5'-end $^{32}$P-labeled linear oligonucleotide substrate was added, and incubation was continued for an additional one hour. Reactions were quenched by the addition of an equal volume (16 μl) of loading dye (98% deionized formamide, 10 mM EDTA, 0.025% xylene cyanol and 0.025% bromophenol blue). An aliquot (5 μl) was electrophoresed on a denaturing 20% polyacrylamide gel (0.09 M tris-borate pH 8.3, 2 mM EDTA, 20% acrylamide, 8M urea).

Gels were dried, exposed in a Phosphorlinager cassette, and analyzed using a Typhoon 8610 Variable Mode Imager (Amersham Biosciences) and quantitated using ImageQuant 5.2. Percent inhibition (% 1) was calculated using the following equation:

$$\%I = 100 \times [1-(D-C)/(N-C)]$$

where C, N, and D are the fractions of 21-mer substrate converted to 19-mer (3-processing product) or strand transfer products for DNA alone, DNA plus IN, and IN plus drug, respectively. The 1050 values were determined by plotting the logarithm of drug concentration versus percent inhibition to obtain concentration that produced 50% inhibition.

Anti-HIV Assays in Cultured Cells: The anti-HIV activity was evaluated in human T cell line CEM-SS infected with HIV-1 as described by Weislow et al. 45 In brief, cells were plated in 96-well plates at $5 \times 10^3$ cells/well and infected with HIV-1RF (MOI=0.3). Serial dilutions of compounds were then immediately added to the cells in a final volume of 200 μl. In each experiment, AZT and dextran sulfate were included as control compounds for anti-HIV activity. The cells were maintained at 37° C. with 5% C02-containing humidified air for 6 days. Cell viability was quantified by absorbance at 450 nm after 4 h incubation with 2,3-bis[2-methoxy-4-nitro-5-sulfophenyl]-5-[(phenylamino)carbonyl]-2H-tetrazolium hydroxide (XTT) at 0.2 mg/ml. Antiviral activity was graded based on the degree of anti-HIV protection as active (80-100% protection), moderate (50-79% protection) and inactive (0-49% protection). Toxicity of the compounds was determined simultaneously on the same plate in uninfected CEM-SS cells.

TABLE 46

Pharmacophore models generated using the training set compounds (1-5) (All chemical features found in the training set compounds considered for pharmacophore generation except the H-bond donor feature)

| Hypothesis | Features Combinations [a] | Ranking Score |
|---|---|---|
| HT5NoDF.01 | HRA1, HRA2, HBA, NI | 53.40 |
| HT5NoDF.02 | RA1, HRA1, HBA, NI | 53.09 |
| HT5NoDF.03 | RA1, HRA1, HBA, NI | 53.09 |
| HT5NoDF.04 | RA1, HRA1, HBA, NI | 53.07 |
| HT5NoDF.05 | RA1, HRA1, HBA, NI | 53.07 |
| HT5NoDF.06 | RA1, RA2, HBA, NI | 52.71 |
| HT5NoDF.07 | RA1, RA2, HBA, NI | 52.71 |
| HT5NoDF.08 | RA1, RA2, HBA, NI | 52.71 |
| HT5NoDF.09 | RA1, RA2, HBA, NI | 52.71 |
| HT5NoDF.10 | HRA1, HRA2, HBA, NI | 51.73 |

[a] HRA1-2:—Hydrophobic Aromatic; HBA:—H-Bond Acceptor; RA1-2:—Ring Aromatic; NI—Negatively Ionizable Feature

TABLE 47

HIV-1 Integrase Inhibitory Activities of Representative Compounds Exemplified by Formula 1

| Compound | Structure | IN inhibition activity | |
|---|---|---|---|
| | | 3'-processing | Strand transfer |
| AV15 | 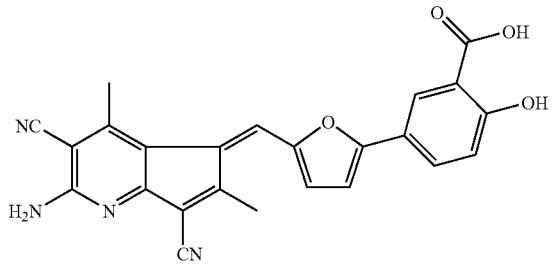 | 9 ± 2 | 4 ± 0.5 |
| AV15A11 | 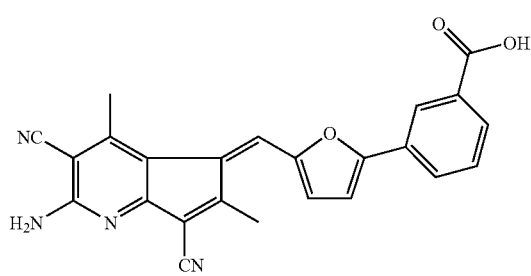 | 24 ± 16 | 20 ± 13 |

TABLE 47-continued

HIV-1 Integrase Inhibitory Activities of Representative Compounds Exemplified by Formula 1

| Compound | Structure | IN inhibition activity | |
|---|---|---|---|
| | | 3'-processing | Strand transfer |
| AV15A13 | 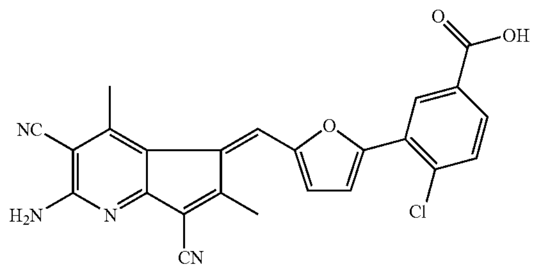 | | |
| AV15A44 | 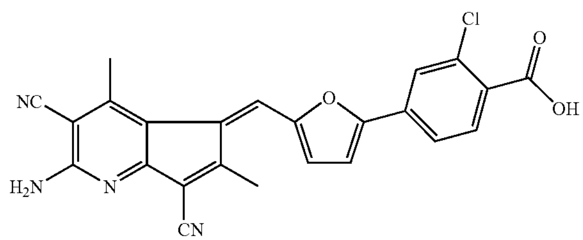 | >100 | 68 ± 22 |
| AV15A45 | 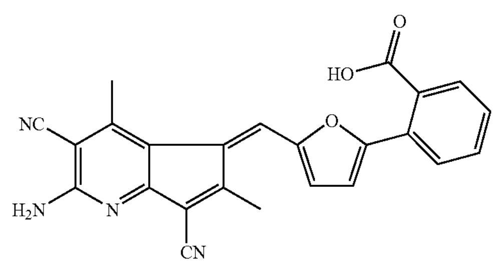 | 91 ± 16 | 39 |
| AV15A48 | 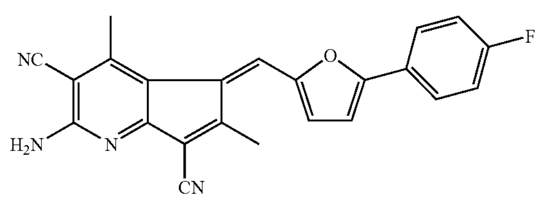 | >100 | >100 |
| AV15A54 | 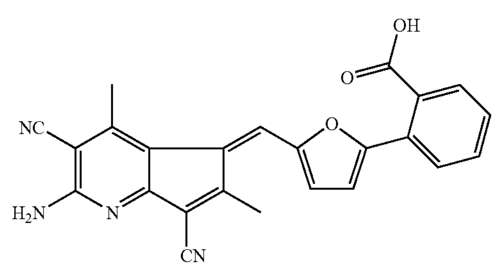 | >100 | >100 |
| AV15A1 | 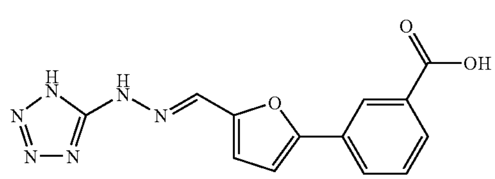 | >>100 | 96 ± 6 |

TABLE 47-continued

HIV-1 Integrase Inhibitory Activities of Representative Compounds Exemplified by Formula 1

| Compound | Structure | IN inhibition activity | |
|---|---|---|---|
| | | 3'-processing | Strand transfer |
| AV15A3 | 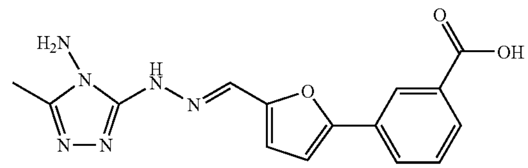 | ? | ? |
| AV15A37 | 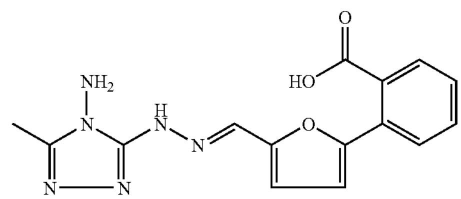 | >100 | >100 |
| AV15A43 | 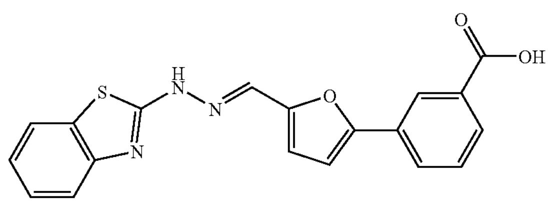 | 63 ± 7 | 24 ± 11 |
| AV15A27 | 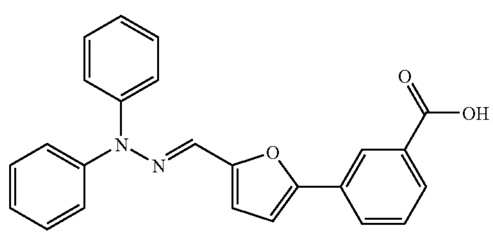 | 42 ± 24 | 26 ± 12 |
| AV15A16 | 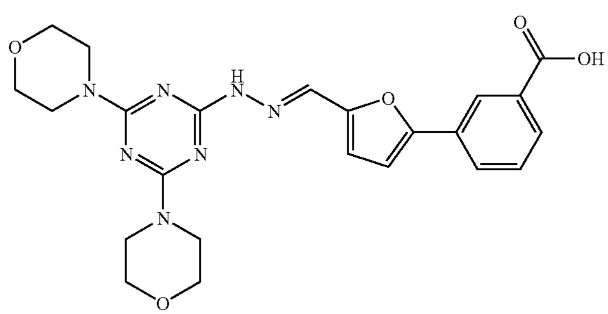 | >100 | >100 |
| AV15A26 | 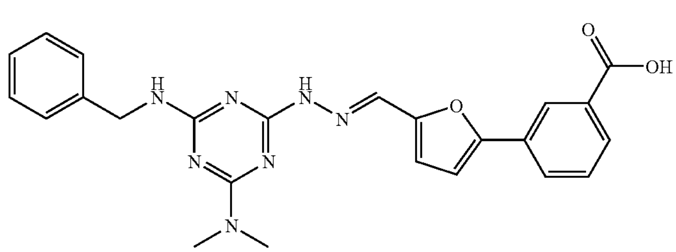 | >>100 | 88 |

TABLE 47-continued
HIV-1 Integrase Inhibitory Activities of Representative Compounds Exemplified by Formula 1
| Compound | Structure | IN inhibition activity | |
|---|---|---|---|
| | | 3'-processing | Strand transfer |
| AV15A28 | 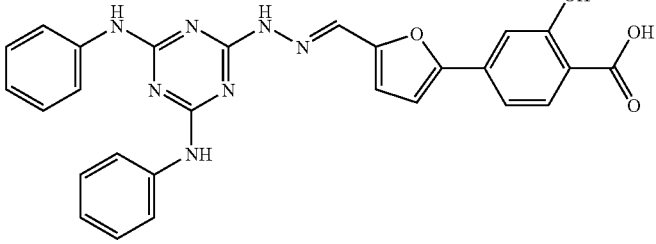 | >100 | >100 |
| AV15A39 | 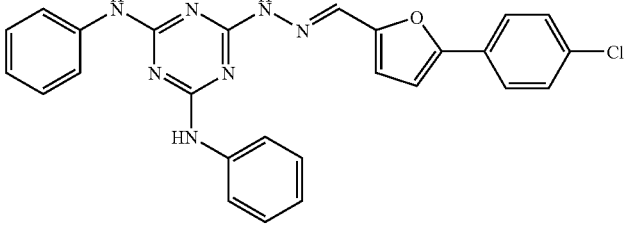 | >100 | >100 |
| AV15A42 | 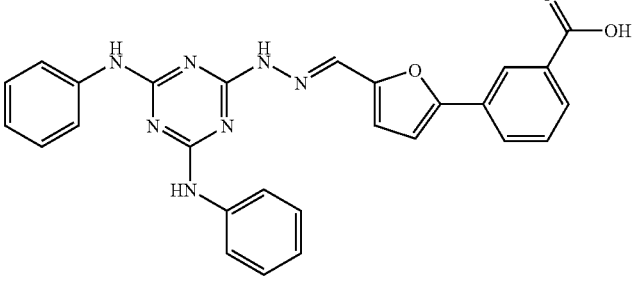 | 89 ± 19 | ? |
| AV15A4 | 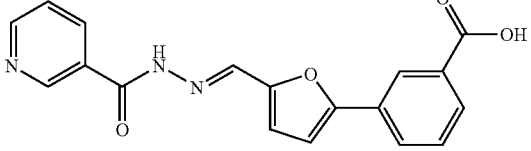 | >>100 | 96 ± 6 |
| SA1 | 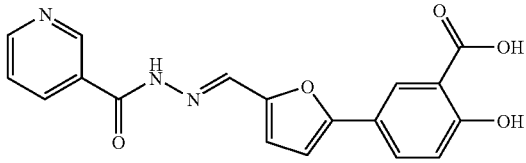 | 59 ± 1 | 9 ± 5 |
| AV15A40 | 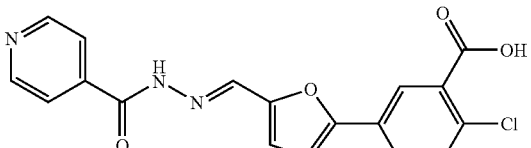 | 90 ± 18 | 46 ± 23 |

TABLE 47-continued

HIV-1 Integrase Inhibitory Activities of Representative Compounds Exemplified by Formula 1

| Compound | Structure | IN inhibition activity | |
|---|---|---|---|
| | | 3'-processing | Strand transfer |
| AV15A41 | | >100 | >100 |
| AV15A36 | | >100 | 56 ± 22 |
| AV15A38 | | >100 | 49 ± 12 |
| AV15A29 | | >100 | 100 |
| AV15A5 | | >>100 | 88 ± 21 |
| AV15A20 | | >>100 | 95 |
| AV15A47 | | >100 | >100 |

TABLE 47-continued
HIV-1 Integrase Inhibitory Activities of Representative Compounds Exemplified by Formula 1
| Compound | Structure | IN inhibition activity | |
|---|---|---|---|
| | | 3'-processing | Strand transfer |
| AV15A35 | 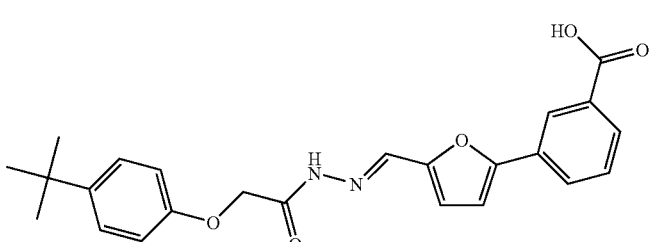 | >>100 | 86 |
| AV15A6 | 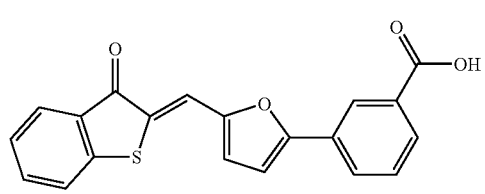 | 76 | 24 |
| AV15A2 | 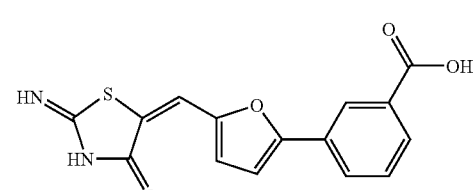 | >>100 | 90 ± 17 |
| T36 | 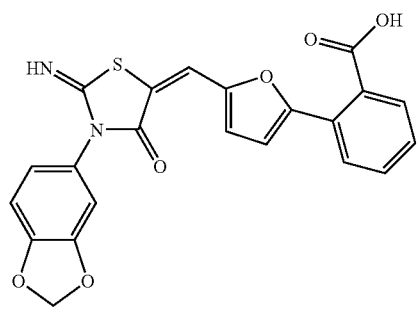 | 12 ± 6 | 6.5 ± 1 |
| X114 | 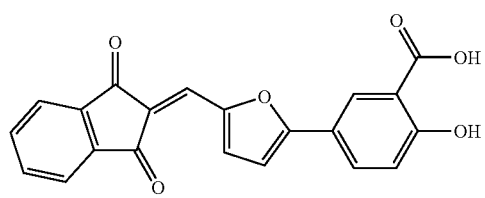 | 40 ± 10 | 43 ± 6 |
| AV15A22 | 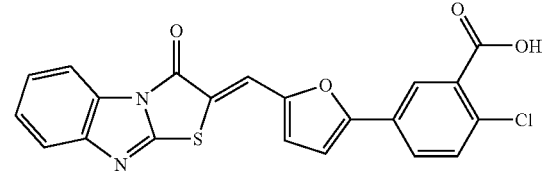 | 23 ± 3 | 15 ± 4 |

TABLE 47-continued

HIV-1 Integrase Inhibitory Activities of Representative Compounds Exemplified by Formula 1

| Compound | Structure | IN inhibition activity | |
|---|---|---|---|
| | | 3'-processing | Strand transfer |
| AV15A32 | | >100 | >100 |
| AV15A12 | | 74 ± 32 | 50 ± 25 |
| AV15A23 | | 89 ± 20 | 62 ± 7 |
| AV15A25 | | >100 | >100 |
| AV15A7 | | >>100 | 17, 100 |
| AV15A9 | | 25 ± 10 | 14 ± 4 |

TABLE 47-continued

HIV-1 Integrase Inhibitory Activities of Representative Compounds
Exemplified by Formula 1

| Compound | Structure | IN inhibition activity | |
|---|---|---|---|
| | | 3'-processing | Strand transfer |
| AV15A10 | 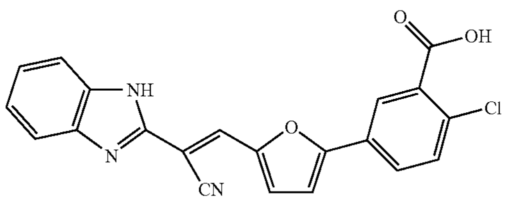 | 76 | 30 |
| AV15A31 | 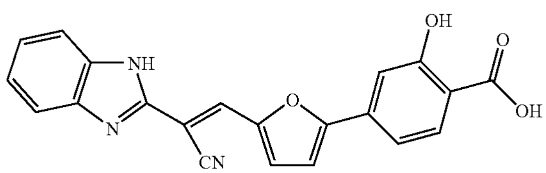 | 34 | 24 |
| AV15A46 | 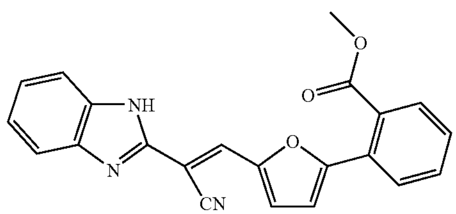 | >100 | >100 |
| AV15A52 | 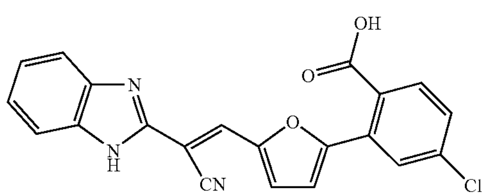 | 100 | 51 |
| AV15A55 | 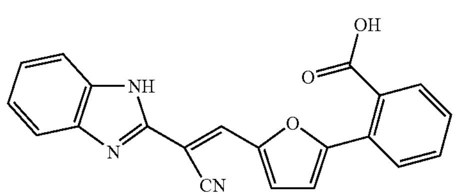 | | |
| AV15A14 | 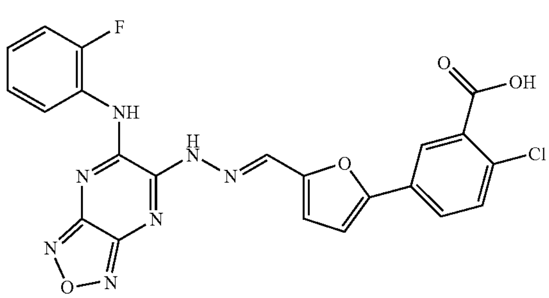 | 16 ± 8 | 13 ± 5 |

TABLE 47-continued

HIV-1 Integrase Inhibitory Activities of Representative Compounds Exemplified by Formula 1

| Compound | Structure | IN inhibition activity | |
|---|---|---|---|
| | | 3'-processing | Strand transfer |
| AV15A15 | | 12 ± 6 | 6.5 ± 1 |
| AV30 | | 10 ± 3 | 4 ± 1 |
| AV15A21 | | 10 ± 5 | 7 ± 2 |
| AV15A24 | | 5 ± 3 | 3.4 ± 2 |
| AV15A33 | | >>100 | |

TABLE 47-continued

HIV-1 Integrase Inhibitory Activities of Representative Compounds Exemplified by Formula 1

| Compound | Structure | IN inhibition activity | |
|---|---|---|---|
| | | 3'-processing | Strand transfer |
| AV15A18 | 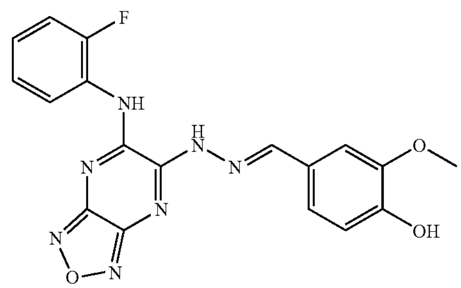 | 30 ± 12 | 17 ± 5 |
| AV15A19 | 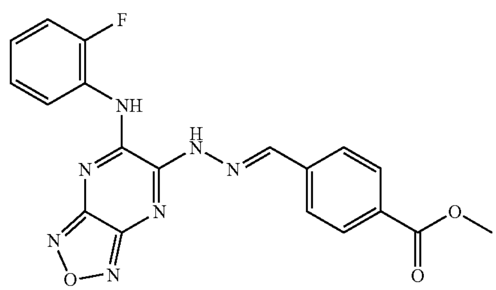 | >>100 | >>100 |

TABLE 48

HIV-1 Integrase Inhibitory Activities of Representative Compounds Exemplified by Formula 41

| Example | Structure | GOLD Score |
|---|---|---|
| NAV1 | 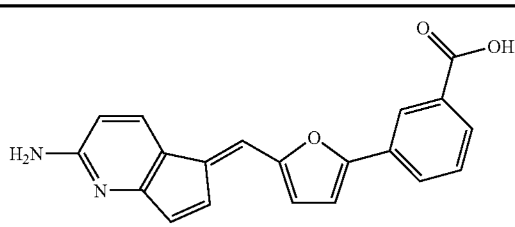 | 48 |
| NAV2 | 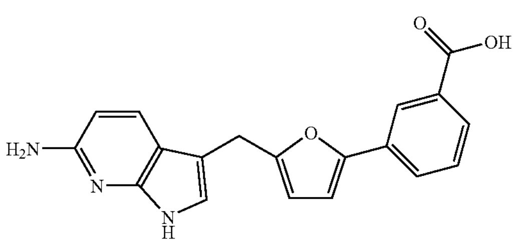 | 56 |
| NAV3 | 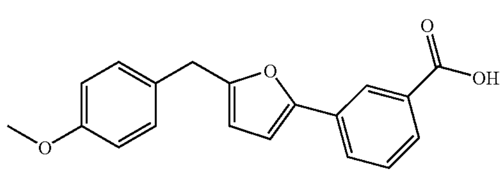 | 45 |

TABLE 48-continued

HIV-1 Integrase Inhibitory Activities of Representative Compounds Exemplified by Formula 41

| Example | Structure | GOLD Score |
|---|---|---|
| NAV4 | 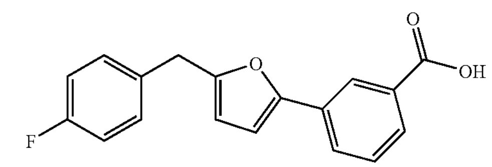 | 40 |
| NAV5 | 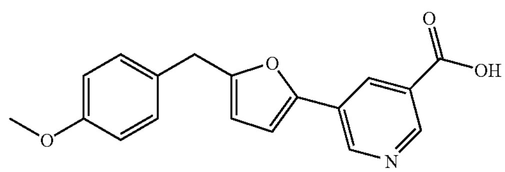 | 42 |
| NAV6 | 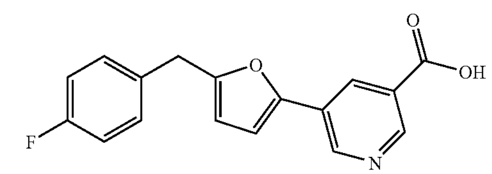 | 41 |
| NAV7 | 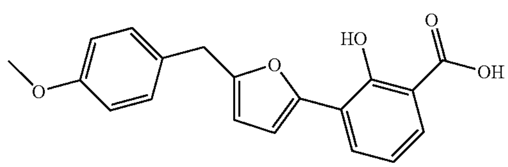 | 50 |
| NAV8 | 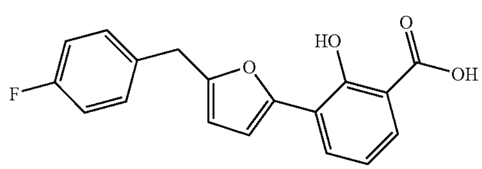 | 50 |
| NAV9 | 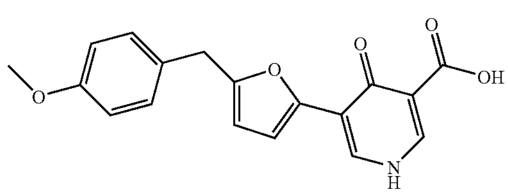 | 45 |
| NAV10 | 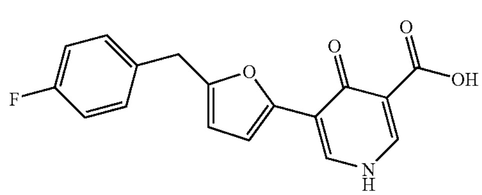 | 42 |
| NAV11 | 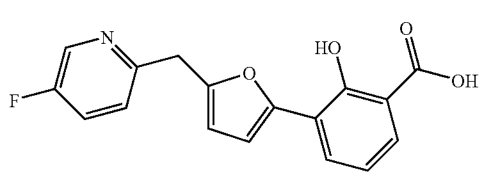 | 48 |

TABLE 48-continued

HIV-1 Integrase Inhibitory Activities of Representative Compounds Exemplified by Formula 41

| Example | Structure | GOLD Score |
|---|---|---|
| NAV12 | 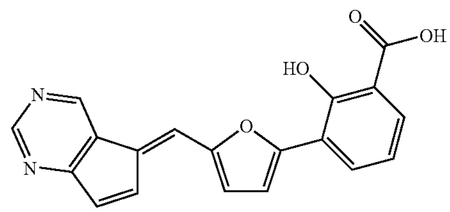 | 48 |

TABLE 49

HIV-1 Integrase Inhibitory Activities of Representative Compounds Exemplified by Formula 42

| Compound | Structure | IN inhibition activity | | GOLD Score |
|---|---|---|---|---|
| | | 3'-processing | Strand transfer | |
| M28 (X155) | | 93 ± 12 | 67 ± 28 | |
| X81 | | 84 ± 23 | 69 ± 36 | |
| T38 | | 25 | 20 | |

TABLE 49-continued

HIV-1 Integrase Inhibitory Activities of Representative Compounds
Exemplified by Formula 42

| Compound | Structure | IN inhibition activity | | GOLD Score |
|---|---|---|---|---|
| | | 3'-processing | Strand transfer | |
| AS16 | 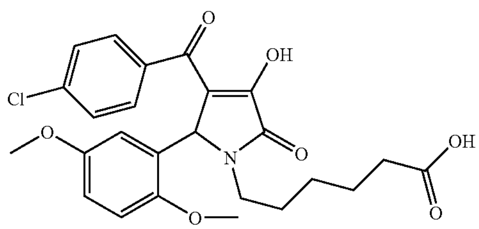 | 88 | 40 ± 5 | |
| AS143 | 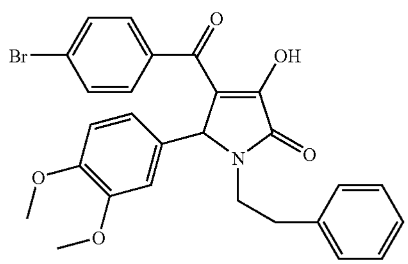 | 60 ± 3 | 42 ± 10 | |
| AS134 | 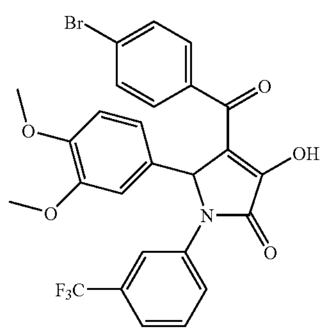 | 47 ± 7 | 26 ± 9 | |
| AS139 BAS 02234865 | 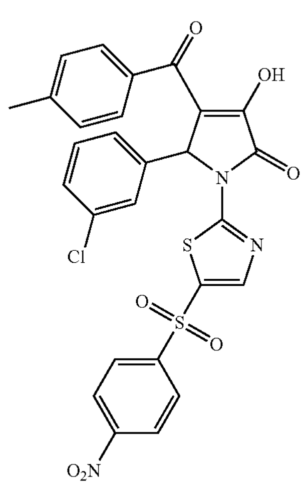 | 27 ± 10 | 8 ± 2 | 60.30 |

TABLE 49-continued

HIV-1 Integrase Inhibitory Activities of Representative Compounds
Exemplified by Formula 42

| Compound | Structure | IN inhibition activity | | GOLD Score |
|---|---|---|---|---|
| | | 3'-processing | Strand transfer | |
| AS161 | 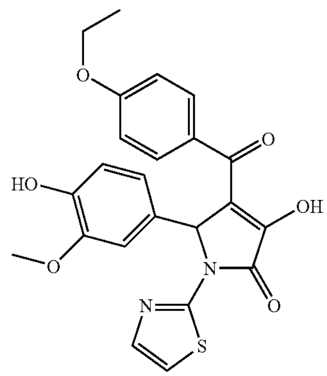 | 57 ± 27 | 30 ± 7 | |
| AS171 | 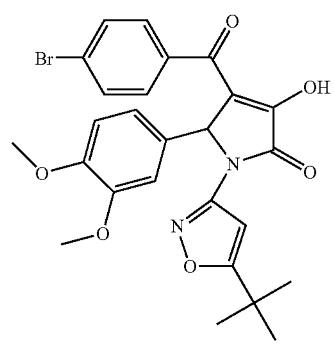 | 45 ± 8 | 43 ± 26 | |
| M28A2 | 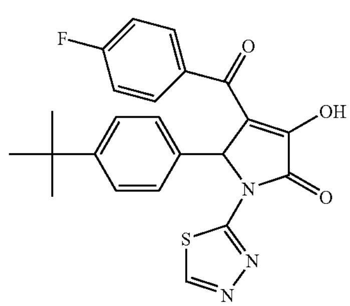 | 64 ± 28 | 43 ± 8 | |
| M28A6 | 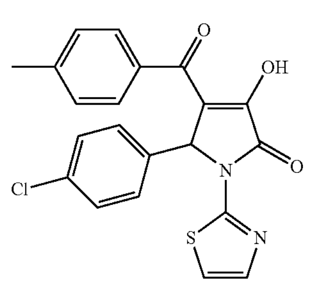 | 56 ± 10 | 39 ± 3 | |

TABLE 49-continued

HIV-1 Integrase Inhibitory Activities of Representative Compounds
Exemplified by Formula 42

| Compound | Structure | IN inhibition activity | | GOLD Score |
|---|---|---|---|---|
| | | 3'-processing | Strand transfer | |
| M28A7 | | >100 | 78 ± 10 | |
| M28A11 | | >100 | 90 ± 17 | |
| M28A10 | | 44 ± 4 | 21 ± 4 | |
| M28A18 | | >100 | 33 ± 25 | |

TABLE 49-continued

HIV-1 Integrase Inhibitory Activities of Representative Compounds Exemplified by Formula 42

| Compound | Structure | IN inhibition activity | | GOLD Score |
|---|---|---|---|---|
| | | 3'-processing | Strand transfer | |
| M28A8 | 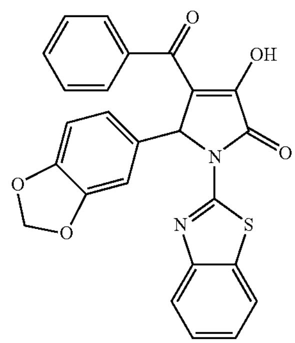 | 57 ± 10 | 21 ± 10 | |
| M28A21 | 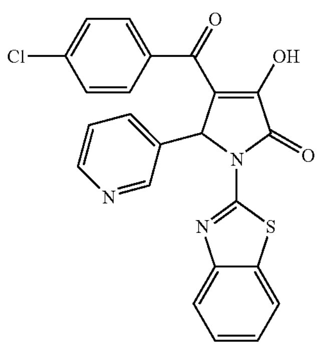 | >100 | 90 ± 10 | |
| M28A22 | 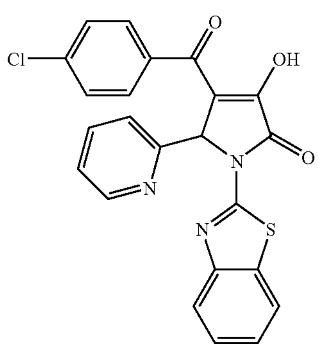 | >100 | 83 ± 12 | |
| AS139noNO2 | 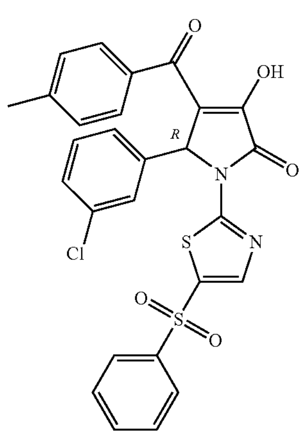 | | | 63.29 |

TABLE 49-continued
HIV-1 Integrase Inhibitory Activities of Representative Compounds Exemplified by Formula 42
| Compound | Structure | IN inhibition activity | | GOLD Score |
|---|---|---|---|---|
| | | 3'-processing | Strand transfer | |
| AS139SnoNO2 | 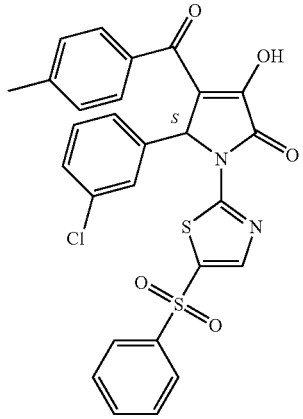 | | | 72.21 |
| AS139S1 | 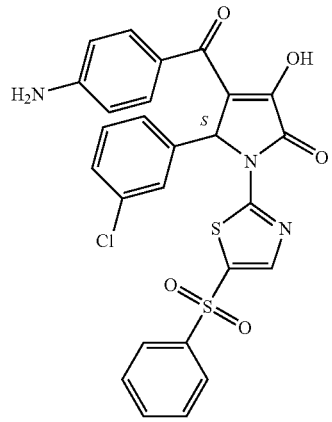 | | | 71.08 |
| AS139S2 | 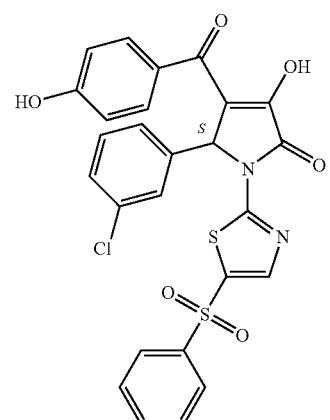 | | | 69.26 |

TABLE 49-continued

HIV-1 Integrase Inhibitory Activities of Representative Compounds
Exemplified by Formula 42

| Compound | Structure | IN inhibition activity | | GOLD Score |
|---|---|---|---|---|
| | | 3'-processing | Strand transfer | |
| AS139S3 | | | | 69.86 |
| AS139S3NH2 | | | | 72.38 |
| AS139S4 | | | | 69.61 |

TABLE 49-continued
HIV-1 Integrase Inhibitory Activities of Representative Compounds
Exemplified by Formula 42
| Compound | Structure | IN inhibition activity | | GOLD Score |
|---|---|---|---|---|
| | | 3'-processing | Strand transfer | |
| AS139S4NH2 | 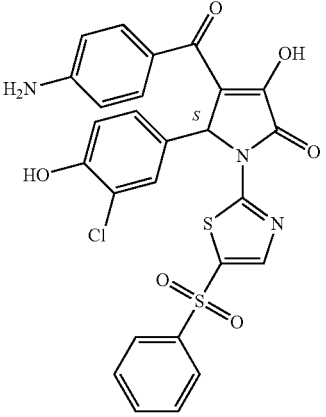 | | | 71.09 |
| AS139S5 | 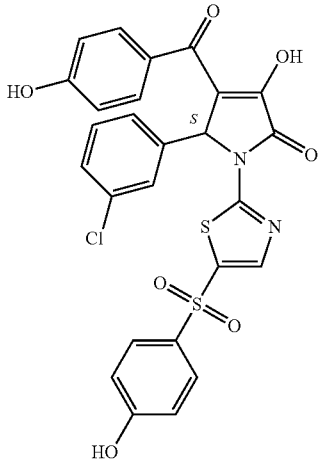 | | | 68.80 |
| AS139S5NH2 | 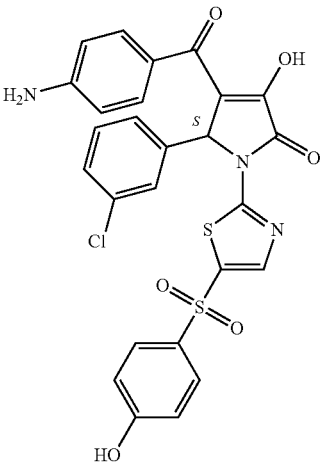 | | | 67.50 |

TABLE 49-continued
HIV-1 Integrase Inhibitory Activities of Representative Compounds
Exemplified by Formula 42
| Compound | Structure | IN inhibition activity | | GOLD Score |
|---|---|---|---|---|
| | | 3'-processing | Strand transfer | |
| AS139S6 | 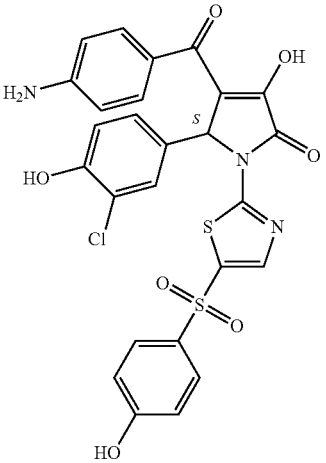 | | | 68.18 |
| AS139S6OH | 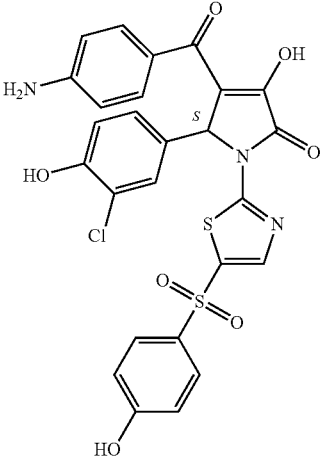 | | | 66.03 |
| AS139S3A2 | 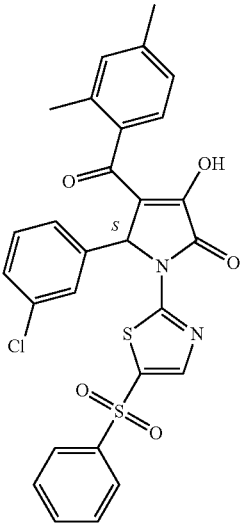 | | | 73.18 |

TABLE 49-continued
HIV-1 Integrase Inhibitory Activities of Representative Compounds Exemplified by Formula 42
| Compound | Structure | IN inhibition activity | | GOLD Score |
|---|---|---|---|---|
| | | 3'-processing | Strand transfer | |
| AS139S3A3 | 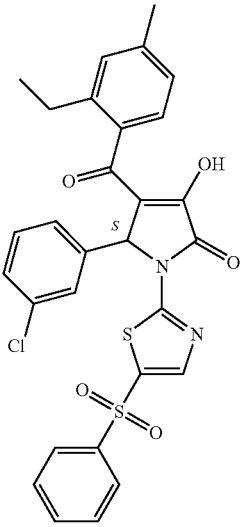 | | | 73.96 |
| AS139S3A4 | 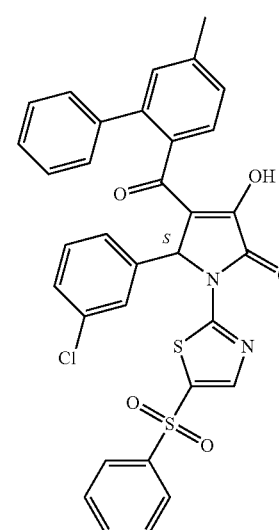 | | | 75.27 |

TABLE 49-continued
HIV-1 Integrase Inhibitory Activities of Representative Compounds Exemplified by Formula 42
| Compound | Structure | IN inhibition activity | | GOLD Score |
|---|---|---|---|---|
| | | 3'-processing | Strand transfer | |
| AS139S3A5 | 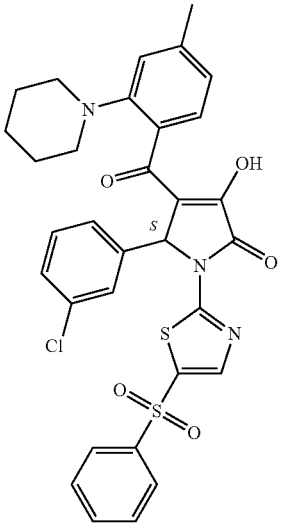 | | | 78.52 |
| AS139S3A5A | 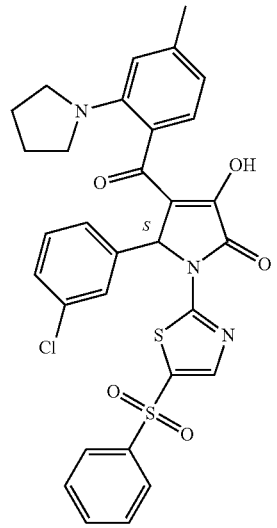 | | | 73.56 |

TABLE 49-continued
HIV-1 Integrase Inhibitory Activities of Representative Compounds
Exemplified by Formula 42
| Compound | Structure | IN inhibition activity | | GOLD Score |
|---|---|---|---|---|
| | | 3'-processing | Strand transfer | |
| AS139S3A1 | 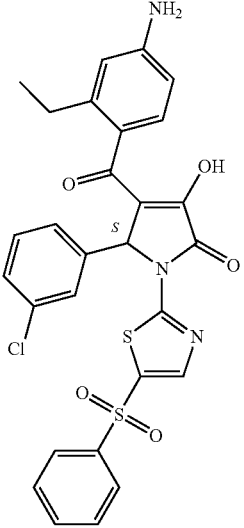 | | | 74.28 |
| AS139S3A6 | 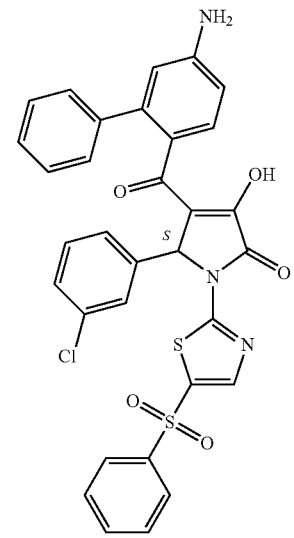 | | | 72.60 |

TABLE 49-continued
HIV-1 Integrase Inhibitory Activities of Representative Compounds Exemplified by Formula 42
| Compound | Structure | IN inhibition activity | | GOLD Score |
|---|---|---|---|---|
| | | 3'-processing | Strand transfer | |
| AS139S3A7 | 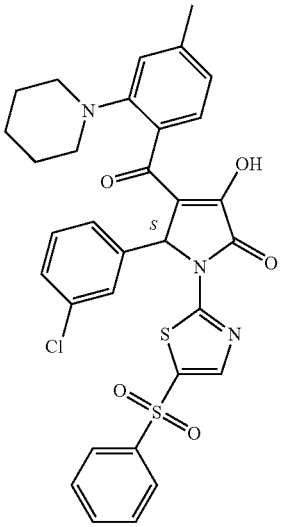 | | | 72.41 |
| AS139S3A8 | 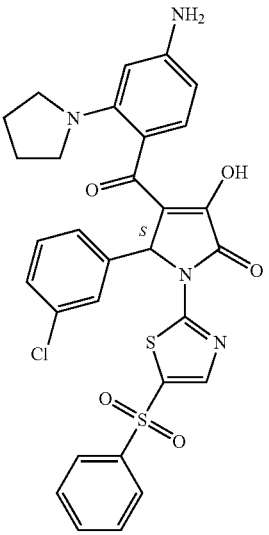 | | | 70 |

TABLE 49-continued

HIV-1 Integrase Inhibitory Activities of Representative Compounds
Exemplified by Formula 42

| Compound | Structure | IN inhibition activity | | GOLD Score |
|---|---|---|---|---|
| | | 3'-processing | Strand transfer | |
| AS139S7 | | | | 72.78 |
| AS139S7NH2 | | | | 70.99 |

TABLE 49-continued

HIV-1 Integrase Inhibitory Activities of Representative Compounds Exemplified by Formula 42

| Compound | Structure | IN inhibition activity | | GOLD Score |
|---|---|---|---|---|
| | | 3'-processing | Strand transfer | |
| AS139S7 | | | | 70.55 |
| AS139S7ME | | | | 69.11 |

TABLE 50

HIV-1 Integrase Inhibitory Activities of Representative Compounds Exemplified by Formula 43

| Compound | Structure | IN inhibition activity | |
|---|---|---|---|
| | | 3'-processing | Strand transfer |
| AS9 | | 5 ± 2 | 3 ± 1 |

TABLE 50-continued

HIV-1 Integrase Inhibitory Activities of Representative Compounds Exemplified by Formula 43

| Compound | Structure | IN inhibition activity 3'-processing | Strand transfer |
|---|---|---|---|
| AS90 | | 21 ± 6 | 9 ± 7 |
| AS120 | | 23 ± 6 | 12 ± 8 |
| AS230 | | 9 ± 1 | 8 ± 4 |
| AS9A1 | | 64 ± 4 | 58 ± 2 |
| AS9A2 | | 18 ± 1 | 17 ± 1 |

TABLE 50-continued

HIV-1 Integrase Inhibitory Activities of Representative Compounds Exemplified by Formula 43

| Compound | Structure | IN inhibition activity 3'-processing | Strand transfer |
|---|---|---|---|
| AS9A3 | 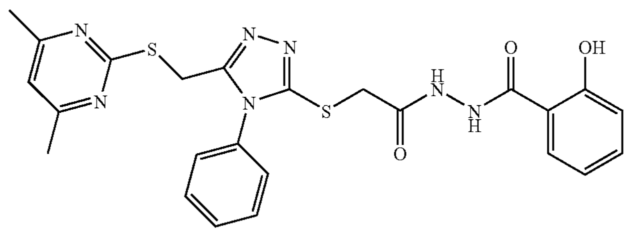 | 51 ± 5 | 27 ± 8 |
| AS9A4 | 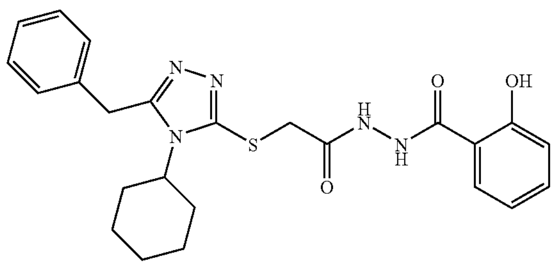 | 21 ± 2 | 17 ± 1 |
| AS9A5 | 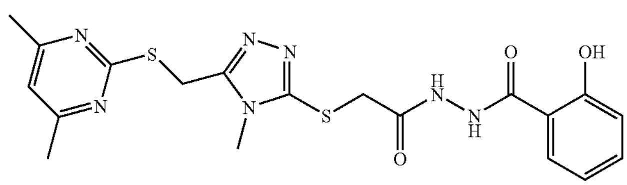 | <100 | <100 |
| AS9A6 | 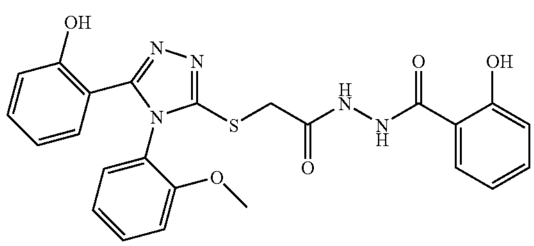 | 8 ± 1 | 6 ± 1 |
| AS9A7 | 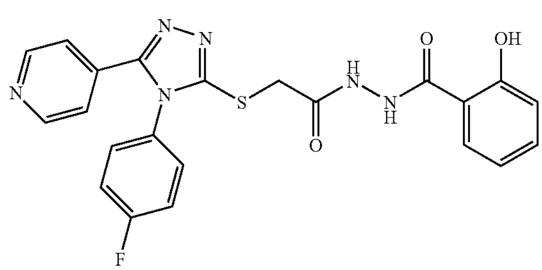 | 49 ± 1 | 31 ± 2 |
| AS9A8 | 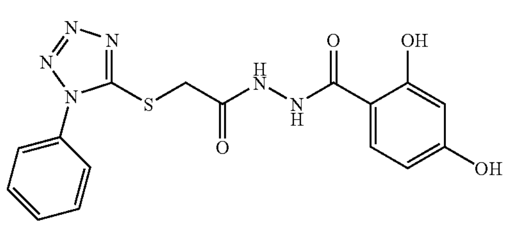 | 68 ± 3 | 61 ± 6 |

TABLE 50-continued

HIV-1 Integrase Inhibitory Activities of Representative Compounds Exemplified by Formula 43

| Compound | Structure | IN inhibition activity | |
| --- | --- | --- | --- |
| | | 3'-processing | Strand transfer |
| AS9A9 | 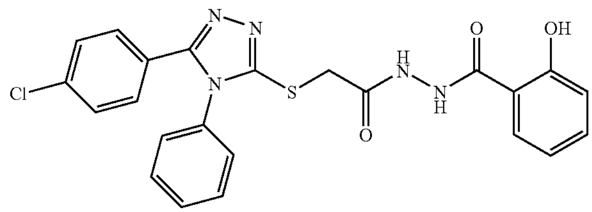 | 11 ± 3 | 5 ± 1 |
| AS9A10 | 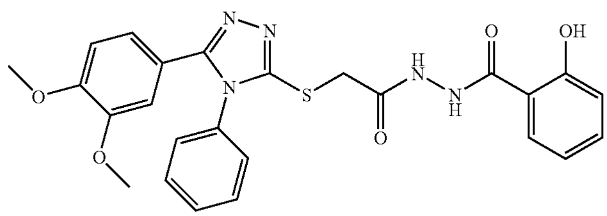 | 22 ± 1 | 21 ± 1 |
| AS9A11 | 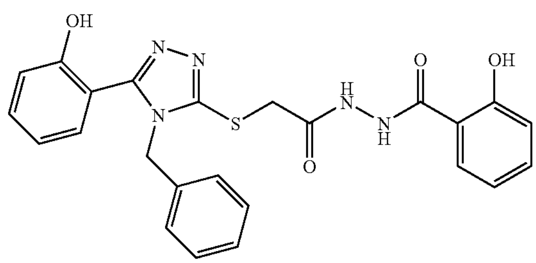 | 15 ± 3 | 9 ± 2 |
| MC41 | 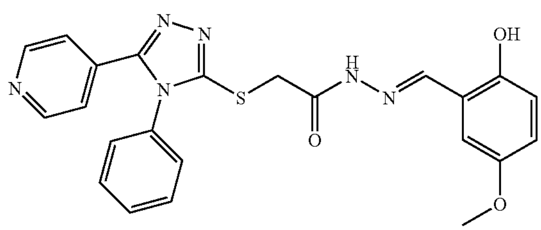 | >>100 | >>100 |
| X244 | 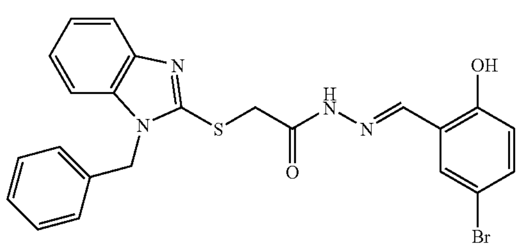 | 60 ± 11 | 51 ± 3 |
| GLD38 | 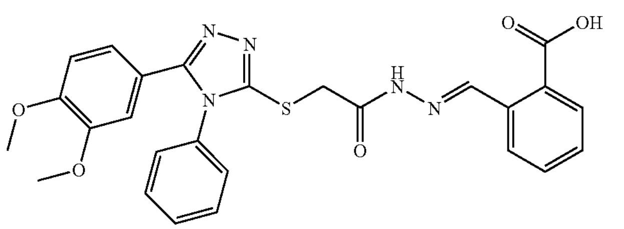 | >100 | >100 |

TABLE 50-continued

HIV-1 Integrase Inhibitory Activities of Representative Compounds Exemplified by Formula 43

| Compound | Structure | IN inhibition activity | |
|---|---|---|---|
| | | 3'-processing | Strand transfer |
| GLD39 | | >100 | >100 |
| OT10 | | >100 | >100 |
| HD39 | | >100 | >100 |
| MPD6 | | >100 | >100 |
| LX6 | | >100 | >100 |
| LX7 | | >100 | >100 |

TABLE 51

HIV-1 Integrase Inhibitory Activities of Representative Compounds Exemplified by Formula 44

| Compound | Structure | IN inhibition activity | | Pharmacophore Fit Value |
|---|---|---|---|---|
| | | 3'-processing | Strand transfer | |
| GLD2 | *(structure: 5,6-di(furan-2-yl)-1,2,4-triazin-3-ylthio acetic acid)* | 18 ± 4 | 5 ± 3 | 2.3 |
| GLD2A2 | *(structure: 4-(4-chlorophenyl)-3-cyano-6-phenyl-2-(carboxymethylthio)pyridine)* | 98 ± 10 | 60 ± 12 | |
| GLD2A4 | *(structure: 4-trifluoromethyl-6-phenylpyrimidin-2-ylthio acetic acid)* | >100 | >100 | |
| GLD2A10 | *(structure: 4-trifluoromethyl-6-(thiophen-2-yl)pyrimidin-2-ylthio acetic acid)* | >100 | >100 | |
| GLD2A3 | *(structure: 4,6-diaminopyrimidin-2-ylthio acetic acid)* | >100 | >100 | |
| GLD2A18 | *(structure: 6-morpholino-2-anilino-1,3,5-triazin-4-ylthio acetic acid)* | >100 | >100 | |

TABLE 52

HIV-1 Integrase Inhibitory Activities of Representative Compounds Exemplified by Formula 45

| Compound | Structure | 3'-processing | Strand transfer | Pharmacophore Fit Value |
|---|---|---|---|---|
| GLD44 | (structure) | 14 ± 6 | 5 ± 4 | 1.7 |
| GLD45 | (structure) | 82 ± 13 | 43 ± 12 | 1.7 |

TABLE 53

HIV-1 Integrase Inhibitory Activities of Structurally Diverse Compounds

| Compound | Structure | 3'-processing | Strand transfer | Pharmacophore Fit Value |
|---|---|---|---|---|
| GLD19 | (structure) | >100 | 52 ± 8 | 1.7 |
| GLD20 | (structure) | >100 | 46 ± 12 | 2.9 |
| GLD25 | (structure) | 42 ± 10 | 18 ± 3 | 3.5 |
| GLD28 | (structure) | 48 ± 19 | 23 ± 4 | 3.1 |

TABLE 53-continued

HIV-1 Integrase Inhibitory Activities of Structurally Diverse Compounds

| Compound | Structure | IN inhibition activity | | Pharmacophore Fit Value |
|---|---|---|---|---|
| | | 3'-processing | Strand transfer | |
| GLD31 | | 92 ± 17 | 66 ± 17 | 3 |
| GLD32 | | >100 | 34 ± 7 | 3.8 |
| GLD59 | | 63 ± 22 | 17 ± 2 | 1.53 |

TABLE 54

HIV-1 Integrase Inhibitory Activities of Representative Compounds Exemplified by Formula 46

| Compound | Structure | IN inhibition activity | | Pharmacophore Fit Value |
|---|---|---|---|---|
| | | 3'-processing | Strand transfer | |
| GLD12 | | 14 ± 7 | 5 ± 3 | 3.1 |
| GLD12A2 | | 5 ± 2 | 4 ± 2 | 2.31 |

TABLE 54-continued

HIV-1 Integrase Inhibitory Activities of Representative Compounds Exemplified by Formula 46

| Compound | Structure | IN inhibition activity | | Pharmacophore Fit Value |
|---|---|---|---|---|
| | | 3'-processing | Strand transfer | |
| GLD12A4 | 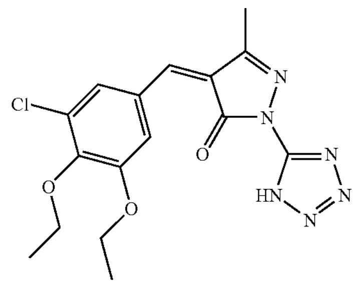 | 7 ± 6 | 4 ± 2 | 2.44 |
| GLD12A3 | 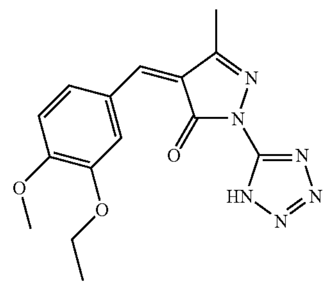 | 75 ± 28 | 59 ± 13 | 2.31 |
| GLD12A5 | 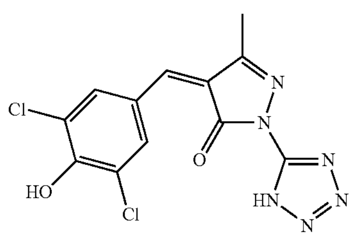 | 11 ± 3 | 13 ± 11 | 2.30 |
| GLD12A1 | 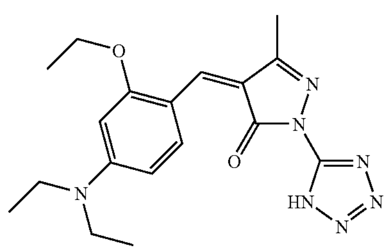 | 61 ± 8 | 65 ± 8 | 2.30 |
| GLD12D1 | 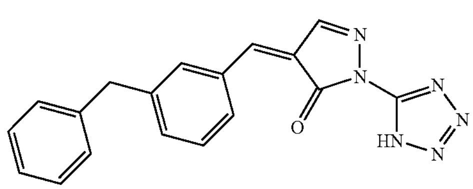 | | | GOLD Score 50.05 |
| GLD12D2 | 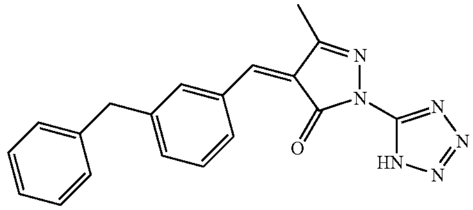 | | | 48.03 |

TABLE 54-continued

HIV-1 Integrase Inhibitory Activities of Representative Compounds Exemplified by Formula 46

| Compound | Structure | IN inhibition activity 3'-processing | Strand transfer | Pharmacophore Fit Value |
|---|---|---|---|---|
| GLD12D3 | 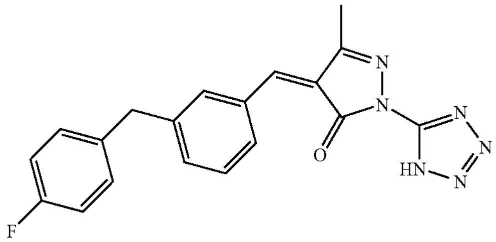 | | | 48.40 |
| GLD12D4 | 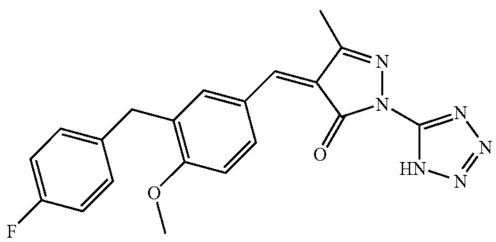 | | | 50.13 |
| GLD12D5 | 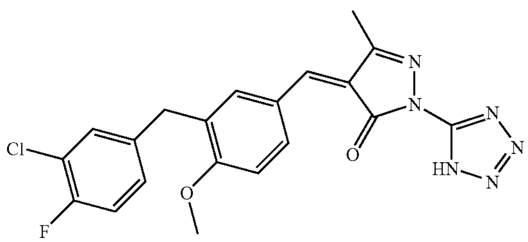 | | | 49.27 |
| GLD12D6 | 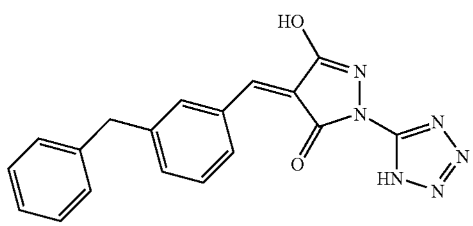 | | | 46.59 |
| GLD12D7 | 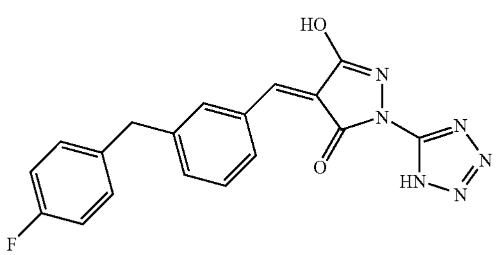 | | | 49.55 |
| GLD12D8 | 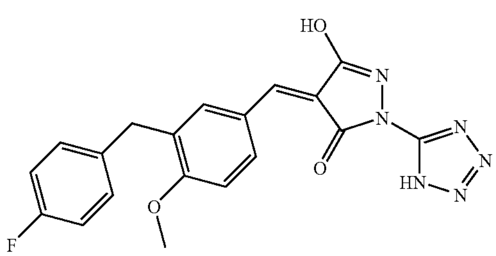 | | | 48.00 |

TABLE 54-continued
HIV-1 Integrase Inhibitory Activities of Representative Compounds Exemplified by Formula 46
| Compound | Structure | IN inhibition activity 3'-processing | Strand transfer | Pharmacophore Fit Value |
|---|---|---|---|---|
| GLD12D9 | 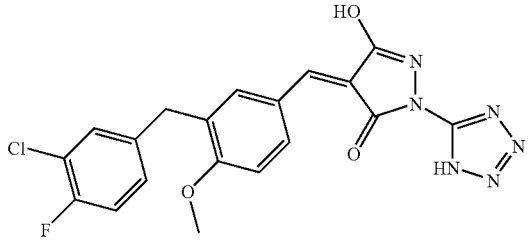 | | | 50.64 |
| GLD12D10 | 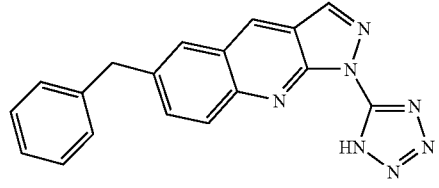 | | | 42.40 |
| GLD12D11 | 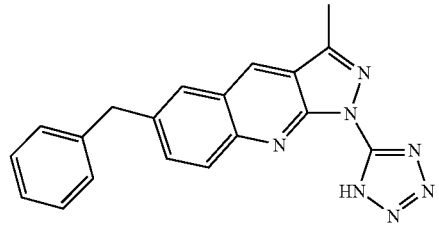 | | | 41.65 |
| GLD12D12 | 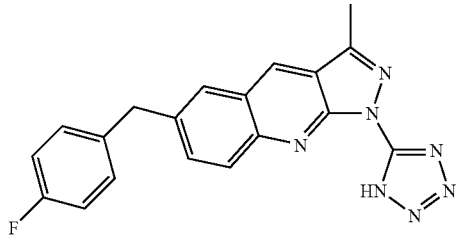 | | | 41.37 |
| GLD12D13 | 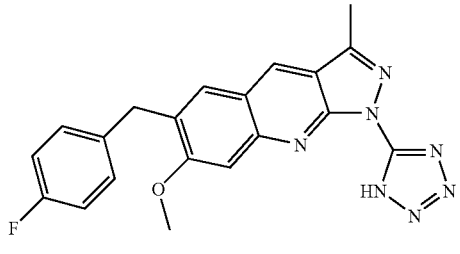 | | | 47.57 |
| GLD12D14 | 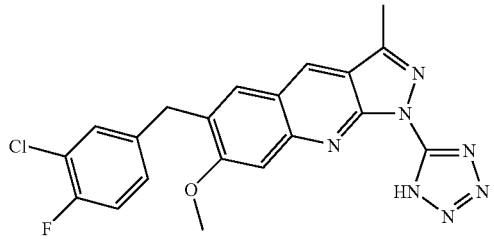 | | | 50.30 |

179                                                                 180

TABLE 54-continued

HIV-1 Integrase Inhibitory Activities of Representative Compounds Exemplified by Formula 46

| Compound | Structure | 3'-processing | Strand transfer | Pharmacophore Fit Value |
|---|---|---|---|---|
| GLD12D15 | 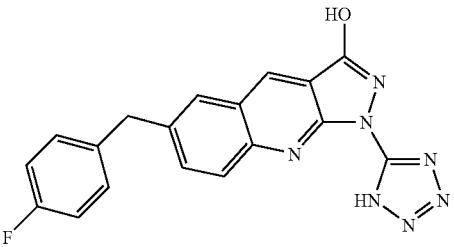 | | | |
| GLD12D16 | 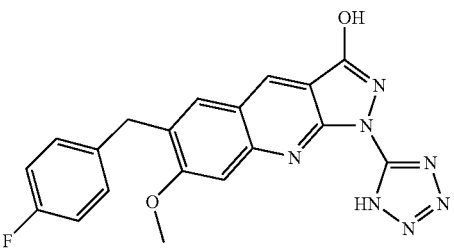 | | | |
| GLD12D17 | 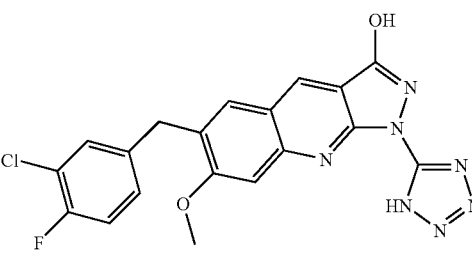 | | | |

TABLE 55

HIV-1 Integrase Inhibitory Activities and Pharmacophore Fit Values of Compounds Designed Based on the GLD12 Scaffold

| Compound | Structure | Pharmacophore Fit Value |
|---|---|---|
| GLD12DA | 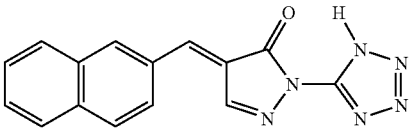 | 2.46 |
| GLD12D1F | 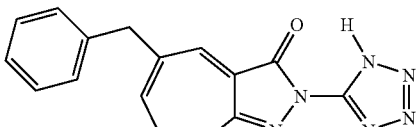 | 3.86 |
| GLD12D1FA | 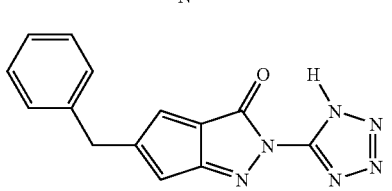 | 3.23 |

TABLE 55-continued

HIV-1 Integrase Inhibitory Activities and Pharmacophore Fit Values
of Compounds Designed Based on the GLD12 Scaffold

| Compound | Structure | Pharmacophore Fit Value |
|---|---|---|
| GLD12D1FB | 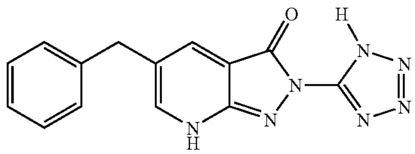 | 2.50 |
| GLD12D1FD | 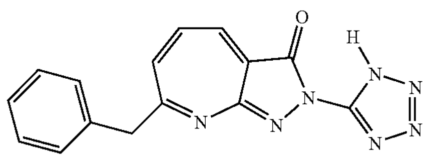 | 2.01 |
| GLD12D1FE | 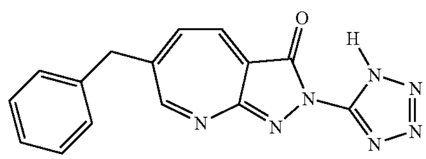 | 3.75 |
| GLD12D1FF | 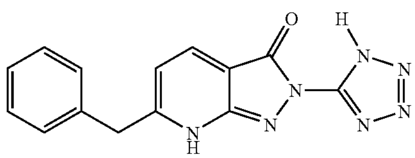 | 3.69 |
| GLD12D1FG | 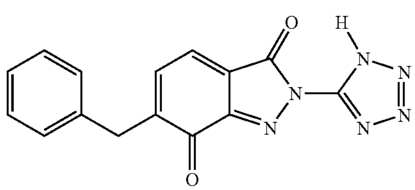 | |
| GLD12D1FH | 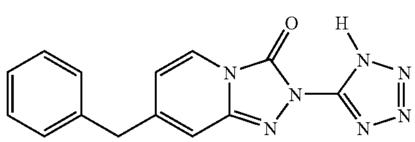 | 2.74 |
| GLD12D1FI | 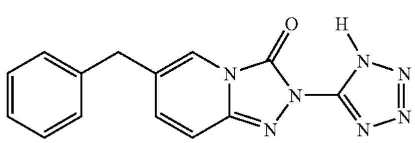 | 3.88 |
| GLD12D1FIA | 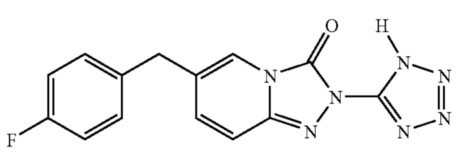 | 3.88 |
| GLD12D1FIB | 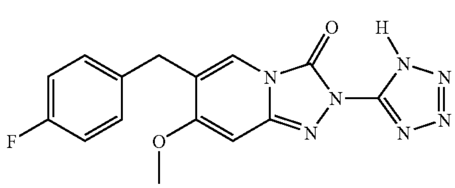 | 3.88 |

TABLE 55-continued

HIV-1 Integrase Inhibitory Activities and Pharmacophore Fit Values
of Compounds Designed Based on the GLD12 Scaffold

| Compound | Structure | Pharmacophore Fit Value |
|---|---|---|
| GLD12DNM1 | 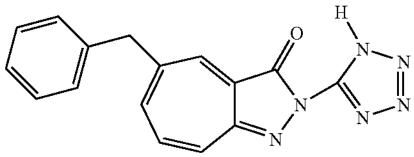 | |
| GLD12DNM2 | 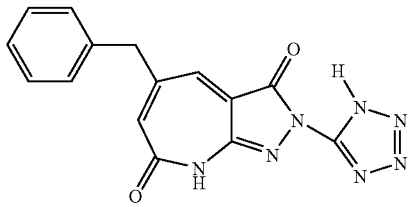 | |

TABLE 56

Representative Compounds Exemplified by Formula 47

| Compound | Structure |
|---|---|
| 3FS1 | 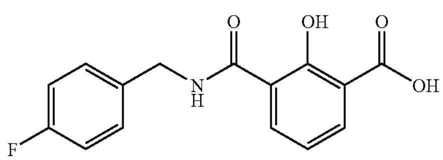 |
| 3FS2 | 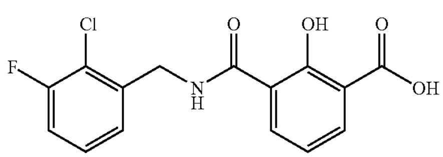 |
| 3FS3 | 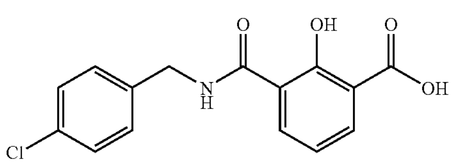 |
| 3FS4 | 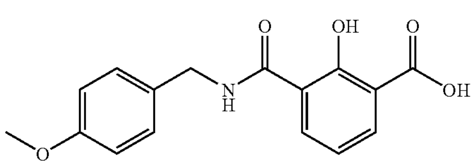 |
| 3FS5 | 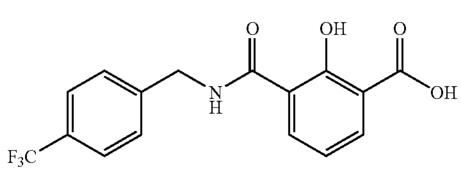 |
| 3FS6 | |
| 3FS7 | |
| 3FS8 | |
| 3FS9 | |
| 3FS10 | |

TABLE 57

Representative Compounds Exemplified by Formula 48

| Compound | Structure |
|---|---|
| 3FSN1 | *(structure)* |
| 3FSN2 | *(structure)* |
| 3FSN3 | *(structure)* |
| 3FSN4 | *(structure)* |
| 3FSN5 | *(structure)* |
| 3FSN6 | *(structure)* |
| 3FSN7 | *(structure)* |

REFERENCES

Deng et at (2007) Biorganic & Medicinal Chemistry 15:4985-5002.

Dayam et al. (2008) J. Med. Chem., 51, 1136-1144.

All publications cited herein are incorporated by reference in their entirety. While the foregoing has been described in considerable detail and in terms of preferred embodiments, these are not to be construed as limitations on the disclosure. Modifications and changes that are within the purview of those skilled in the art are intended to fall within the scope of the invention.

---

What is claimed is:

1. A method of inhibiting HIV-1 integrase, comprising contacting a composition comprising

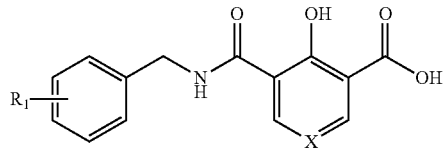

(Formula 48)

wherein $R_1$ is selected from the group consisting of hydrogen, halogen, hydroxyl, sulfhydryl, alkoxy, carboxyl, carbonyl, nitro, cyano, amino, amide, sulfonyl, sulfonamide, nitro, substituted aliphatic, heteroaliphatic, aryl, and heteroaryl, wherein X is selected from the group consisting of CH or N, or a pharmaceutically acceptable salt thereof with an HIV-1 integrase, thereby inhibiting the activity of the HIV-1 integrase.

2. The method of claim 1, wherein X is N.

3. The method of claim 2, wherein $R_1$ is H.

4. The method of claim 1, wherein the composition further comprises a carrier.

5. A method of inhibiting HIV-1 integrase, comprising contacting a composition comprising

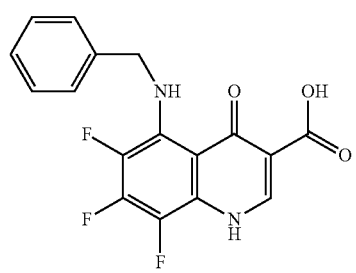

ROM3 or a pharmaceutically acceptable salt thereof, with an HIV-1 integrase, thereby inhibiting the activity of the HIV-1 integrase.

* * * * *